US011761012B2

(12) United States Patent
Settles et al.

(10) Patent No.: US 11,761,012 B2
(45) Date of Patent: Sep. 19, 2023

(54) MITIGATION OF MAIZE HEAT STRESS WITH RECOMBINANT 6-PHOSPHOGLUCONATE DEHYDROGENASE

(71) Applicant: UNIVERSITY OF FLORIDA RESEARCH FOUNDATION, INC., Gainesville, FL (US)

(72) Inventors: Andrew Mark Settles, Gainesville, FL (US); Camila Ribeiro, Winter Haven, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 100 days.

(21) Appl. No.: 16/761,451

(22) PCT Filed: Nov. 5, 2018

(86) PCT No.: PCT/US2018/059274
§ 371 (c)(1),
(2) Date: May 4, 2020

(87) PCT Pub. No.: WO2019/090265
PCT Pub. Date: May 9, 2019

(65) Prior Publication Data
US 2020/0392527 A1    Dec. 17, 2020

Related U.S. Application Data

(60) Provisional application No. 62/581,070, filed on Nov. 3, 2017.

(51) Int. Cl.
*C12N 15/82*    (2006.01)
*C07K 14/415*    (2006.01)
*C12N 9/04*    (2006.01)

(52) U.S. Cl.
CPC ........ *C12N 15/8273* (2013.01); *C07K 14/415* (2013.01); *C12N 9/0006* (2013.01); *C07K 2319/08* (2013.01); *C12N 2800/10* (2013.01); *C12Y 101/01* (2013.01)

(58) Field of Classification Search
None
See application file for complete search history.

(56) References Cited

U.S. PATENT DOCUMENTS

| | | | |
|---|---|---|---|
| 2005/0216967 A1* | 9/2005 | Heim | C12N 15/8216 800/278 |
| 2005/0278803 A1* | 12/2005 | Sewalt | A23L 7/148 800/278 |
| 2008/0050506 A1 | 2/2008 | Manjunath et al. | |
| 2012/0304336 A1 | 11/2012 | Bourett et al. | |

OTHER PUBLICATIONS

UniProt Accession P04713, dated Aug. 13, 1987. (Year: 1987).*
Andriotis, Vasilios M. E. et al., "The plastidial pentose phosphate pathway is essential for postglobular embryo development in *Arabidopsis*", PNAS; Jul. 23, 2019; vol. 116, No. 30, pp. 15297-15306.
Averill, Rachel H. et al., "Co-operation between cytosolic and plastidic oxidative pentose phosphate pathways revealed by 6-phosphogluconate dehydrogenase-deficient genotypes of maize", The Plant Journal, 1998, vol. 14, No. 4, pp. 449-457.
Bahaji, Abdellatif et al., "Starch biosynthesis, its regulation and biotechnological approaches to improve crop yields", Biotechnology Advances, 2014, vol. 32, pp. 87-106.
Bailey-Serres, Julia et al., "Expression and Distribution of Cytosolic 6-Phosphogluconate Dehydrogenase Isozymes in Maize", Biochemical Genetics, 1992, vol. 30, Nos. 5/6, pp. 233-246.
Bailey-Serres, Julia et al., "Purification and Characterization of Cytosolic 6-Phosphogluconate Dehydrogenase Isozymes from Maize", Plant Physiol., 1992, vol. 100, pp. 1580-1583.
Boehlein, Susan K et al., "Effects of long-term exposure to elevated temperature on *Zea mays* endosperm development during grain fill", The Plant Journal, 2019, vol. 99, pp. 23-40.
Debnam, Phillip M. et al., "Subcellular distribution of enzymes of the oxidative pentose phosphate pathway in root and leaf tissues", Journal of Experimental Botany,1999, vol. 50, No. 340, pp. 1653-1661.
Dolferus, Rudy et al., "Abiotic stress and control of grain number in cereals", Plant Science, 2011, vol. 181, pp. 331-341.
Doll, Nicolas M. et al., "Transcriptomics at Maize Embryo/Endosperm Interfaces Identifies a Transcriptionally Distinct Endosperm Subdomain Adjacent to the Embryo Scutellum", The Plant Cell, 2020, vol. 32, pp. 833-852.
Gong, Fangping et al., "Making better maize plants for sustainable grain production in a changing climate", Frontiers in Plant Science, 2015, vol. 6, article 835, 6 pages.
Hannah, Curtis L. et al., "A brittle-2 transgene increases maize yield by acting in maternal tissues to increase seed number", Plant Direct, 2017, pp. 1-9.
He, Weiwei et al., "Crystal structure of *Saccharomyces cerevisiae* 6-phosphogluconate dehydrogenase Gnd", BMC Structural Biology, 2007, vol. 7, No. 38, 9 pages.
Hölscher, Christian et al., "Defects in Peroxisomal 6-Phosphogluconate Dehydrogenase Isoform PGD2 Prevent Gametophytic Interaction in *Arabidopsis thaliana*", Plant Physiol., 2016, vol. 171, No. (1), pp. 192-205.

(Continued)

*Primary Examiner* — Charles Logsdon
(74) *Attorney, Agent, or Firm* — Timothy H. Van Dyke; WOLTER, VAN DYKE, DAVIS, PLLC

(57) ABSTRACT

The disclosure relates to modification of a heat resistant cytoplasmic heat stable 6-phosphogluconate dehydrogenase (6PGDH) enzyme by fusing the cytoplasmic 6PGDH enzyme in frame to a plastid-targeting sequence. This modification allows the import of the cytoplasmic 6PGDH enzyme into plastids of a plant cell. Polynucleotides encoding and expressing the modified cytoplasmic 6PGDH enzymes are provided. The disclosure further provides transgenic plants and seeds containing the disclosed polynucleotides and expressing the modified cytoplasmic 6PGDH enzymes during development. The invention further relates to methods for developing a transgenic plant that has increased heat resistance and yield during heat stress.

9 Claims, 44 Drawing Sheets

(56) References Cited

OTHER PUBLICATIONS

Hou, Fu-Yun et al., "The 6-phosphogluconate Dehydrogenase Genes Are Responsive to Abiotic Stresses in Rice", Journal of Integrative Plant Biology, 2007, vol. 49, No. 5, pp. 655-663.

Klosgen, Ralf Bernd et al., "The amyloplast-targeting transit peptide of the waxy protein of maize also mediates protein transport in vitro into chloroplasts", Mol Gen Genet, 1989, vol. 217, pp. 155-161.

Kruger, Nicholas J. et al., "The oxidative pentose phosphate pathway: structure and organisation", Current Opinion in Plant Biology 2003, vol. 6, pp. 236-246.

Raza, Ali et al., "Impact of Climate Change on Crops Adaptation and Strategies to Tackle Its Outcome: A Review" Plants, 2019, vol. 8, No. 34, 29 pages.

Ribeiro, Camila et al., "Engineering 6-phosphogluconate dehydrogenase to improve heat tolerance in maize seed development", PNAS, May 20, 2020, 9 pages.

Ribeiro, Camila, "Engineering 6-Phosphogluconate Dehydrogenase to Improve Heat Stability of Starch Accumulation in Maize Seed Development", A Dissertation Presented to the Graduate School of the University of Florida in Partial Fulfillment of the Requirements for the Degree of Doctor of Philosophy, 2017, 125 pages.

Sakulsingharoj, Chotipa et al., "Engineering starch biosynthesis for increasing rice seed weight: the role of the cytoplasmic ADP-glucose pyrophosphorylase", Plant Science, 2004, vol. 167, pp. 1323-1333.

Settles, A Mark et al., "Sequence-indexed mutations in maize using the UniformMu transposon-tagging population", BMC Genomics, 2007, vol. 8, 12 pages.

Smidansky, Eric D et al., "Expression of a modiWed ADP-glucose pyrophosphorylase large subunit in wheat seeds stimulates photosynthesis and carbon metabolism", Planta, 2007, vol. 225, pp. 965-976.

Smidansky, Eric D et al., "Seed yield and plant biomass increases in rice are conferred by deregulation of endosperm ADP-glucose pyrophosphorylase", Planta, 2003, vol. 216, pp. 656-664.

Smidansky, Eric D et al., "Enhanced ADP-glucose pyrophosphorylase activity in wheat endosperm increases seed yield", PNAS, Feb. 5, 2002, vol. 99, No. 3, pp. 1724-1729.

Spielbauer, Gertraud et al., "Robustness of central carbohydrate metabolism in developing maize kernels", Phytochemistry, 2006, vol. 67, pp. 1460-1475.

Spielbauer, Gertraud et al., "Chloroplast-localized 6-phosphogluconate dehydrogenase is critical for maize endosperm starch accumulation", Journal of Experimental Botany, 2013, vol. 64, No. 8, pp. 2231-2242.

Stuber, C.W. et al., Inheritance, Intracellular Localization, and Genetic Variation of Phosphoglucomutase Isozymes in Maize (*Zea mays* L.), Biochemical Genetics, 1983, vol. 21, No. 7/8, pp. 667-689.

Tanksley, Steven D. et al., "Genetics, Subcellular Localization, and Molecular Characterization of 6-Phosphogluconate Dehydrogenase Isozymes in Tomato", Biochemical Genetics, 1986, vol. 23, No. 5/6, pp. 441-454.

PCT/US2018/059274, The International Search Report and the Written Opinion, dated Mar. 11, 2019, 10 pages.

\* cited by examiner

- Endosperm zein promoter sequences (27kDa promoter sequence(s)); NOS terminator sequence;
Full vector sequence bellow:

FIG. 7A pIPK27-MCSBAR

```
       LB
   1   GGCAGGATAA ATTCAATTGT AAATGGCTTC ATGTCCGGGA AATCTACATG GATCAGCAAT GAGTATGATG GTCAATATGG AGAAAAAGAA AGAGTAATTA
       CCGTCCTATA TAAGTTAACA TTTACCGAAG TACAGGCCCT TTAGATGTAC CTAGTCGTTA CTCATACTAC CAGTTATACC TCTTTTTCTT TCTCATTAAT

101   CCAATTTTTT TTCAATCAAA AAATGTAGAT GTCCGCAGCG TTATTATAAA ATGAAAGTAC ATTTTGATAA AACGACAAAT TACGATCCGT CGTATTTATA
       GGTTAAAAAA AAGTTAGTT TTTACATCTA CAGGCGTCGC AATAATATTT TACTTTCATG TAAAACTATT TTGCTGTTTA ATGCTAGGCA GCATAAATAT

201   GGCGAAGCA ATAAACAAAT TATTCTAATT CGGAAATCTT TATTCTACATT CACGTCCAAT TGGGGCTTA GATGAGAAAC TTCACGATCG
       CCGCTTTCGT TATTTGTTTA ATAAGATTAA GCCTTTAGAA ATAAAGCTGC ACAGATGTAA ACCCCCGAAT CTACTCCTTG AAGTGCTAGC

301   GCTCTAGTAG TCTGCAGTGC AGCCGTGACCC GGTCGTGCCC CTCGTCTAGAG ATAATGAGCA TTGCATGTCT AAGTTATAAA AAATTACCAC ATATTTTTTT
       CGAGATCATC AGACGTCACG TCGGCACTGGG CCAGCACGGG GAGAGATCTC TATTACTCGT AACGTACAGA TTCAATATTT TTTAATGGTG TATAAAAAAA

ZmUq Promoter
 401   TGTCACACTT GTTGAAGTG CAGTTTATCT ATCTTTATAC ATATATTTAA ACTTTACTCT ACGAATAATA TAATCTATAG TACTACAATA ATATCAGTGT
       ACAGTGTGAA CAACTTCAC GTCAAATAGA TAGAAATATG TATATATAATT TGAAATGAGA TGCTTAATTAT ATTAGATATC ATGATGTTAT TATAGTCACA ZmUq Promoter
 501   TTTAGAGAAT CATAAATAAT GTTGACTAAA CATGGACTAA AGGACAATTG AGTATTTGA CAACAGGACT CTACAGTTTT ATCTTTTTAG TGTGCATGTG
       AAATCTCTTA GTATATTTA CAACTGATTT GTACCAGATT TCCGTGTAAC TCATAAAAACT GTTGTCCTGA GATGTCAAAA TAGAAAAATC ACACGTACAC End LB seq               ZmUq Promoter
 601   TTCTCCTTTT TTTTTGCAAA TAGCTTTTAC TTCATCCATT TTATTAAGTAC ATCCATTTAG GGTTTAGGGT TAATGGTTT TATAGACTAA
       ARGAGGAAA AAAACGTTT ATCGAAGTGG ATATATTATG AAGTAGGTAA AATAATCATG TAGGTAAATC CCAAATCCCA ATTACCAAAA ATATCTGATT ZmUq Promoter
 701   TTTTTTAGT ACATCTATTT TAATTCTATTT TAGCCTCTAA ATTAAGAAAA CTAAAACTCT ATTTTAGTTT TTTATTTAA TAATTTAGAT ATAAAATAGA
       AAAAAAATCA TGTAGATAAA ATAAGATAAA ATCGGAGATT ATGGACTTA GATTTTGAGA TAAAATCAAA AAAATAAATT ATTAAATCTA TATTTTATCT ZmUq Promoter
 801   ATAAAATAAA GTGACTAAGT CATGGACTAA ATTAAACAAA TACCCTTTAA GAAATTAAAA AACTAAGGA AACATTTTTC TGTTTCGAG TAGATAATGC CAGCCTGTTA
       TATTTTATTT CACTGATTTT ATGGAAATT CTTTAATTGT TTGATTCCT TTGATTCCT TTGTAAAAAG AACAAAGCTC ATCTATTACG GTCGGACAAT ZmUq Promoter
 901   AACGCCGTCG ATCGACGAGT CCGGCTCCACC GTTGGACTTG CTCCCGTGTC GGCATTCAGA AATTGCGTGG CGGAGCGGCA GACGTGAGCC GGCACGGCAG
       TTGCGGCAGC TAGCTGCTCA GATTCGTGT GGTTGGCCTCT TTGGTCGTCG CAGCGCAGG GCTAGGGTCT TTAACGCACC CGCTAGAGA CCGTGCCGTC ZmUq Promoter
1001   CTGGACCCGT CTCGAGAGTT CCGCTCCACC GTTGGACTTG CTCCCGTGTC GGCATTCAGA AATTGCGTGG CGGAGCGGCA GACGTGAGCC GGCACGGCAG
       GACCTGGGGA GAGCTCTCAA GGCGAGGTGG CAACCTGAAC GAGGCGACAG CCGTAGGTCT TTAACGCACC GCCTCGCCGT CTGCACTCGG CCGTGCCGTC
```

```
                                                 BsrGI             MluI         BamHI
                                                                   ~~~~AvrII   ~~~~NruI
3301 TCTTAAGAAA CTTTAATGCC AAATGTTGAA ACGATCGGGG AAATTCGAGT CATCACCACT TTGGACAAAC TTGTGATGAC ACGGGTCCTA GGGGATCCTC
     AGAATTCTTT GAAATTACGG TTTACAACTT TGCTAGCCCC TTTAAGCTCA GTAGTGGTGA AACCATGTTTG AACACTACTG TGCCCAGGAT CCCCTAGGAG
           Tnos
     NruI    SalI
     ~~~~ SacI ~~~~HindIII
3401 GCGAGAGCTC GTGGGTTCTT CTGCGCTCTG GAGTAGATAA AGCTAATGGT CTGAAGACCC AGTGGTGGTG ATGGAGAAGT GCACAGGCAT
     CGCTCTCGAG CACCCAAGAA GACGCGAGAC CTCATCTATT TCGATTACCA GACTTCTGGG TCACCACCAC TACCTCTTCA CGTGTCCGTA
                                                                                                -27Kpriprimer
                                               -- 5' UTR --
3501 GCGAGCGTTA TTTATAGCTT TGATTAATTA ACACAATTTC TTGTGTTCTT ATGCCACCGA GACGGCTGTA GGCAGCTTCA TGGTTCTTG CCAATGTAT
     CGCTCGCAAT AAATATCGAA ACTAATTAAT TGTGTTAAAG AACACAAGAA TACGGTGGCT CTGCCGACAT CCGTCGAAGT ACCAAGAAC GGTTACATA
                                       27 kDa Promoter
3601 ATGACTCGTC ACTCTCTTTA CGTAGCACGT CGAATGGTTCA TCTGGAATCA TTCTGTACTT CTGCGTGGCT CAGTTTGTT GCCTTGTACA GGTTGTTGAT
     TACTGAGCAG TGAGAGAAAT GCATCGTGCA GCTTACCAAGT AGACCTTAGT AAGACATGAA GACGCACCGA GTCAAAACAA CGGAAGATGT CCAACAA
                                       27 kDa Promoter                                                end RB seq
3701 CTACGTAAAA CGAATTAGAT TTAGCTTGAC ATATGGCTTT TTTTTGTTG TAAATTTACT TTACACGTCA AGGATTTTG TCCTGTTCCG GCCTATTTA
     GATGCATTTT GCTTAATCTA AATCGAACTG TATACCGAAA AAAAAACAAC ATTTAAATGA AATGTGCAGT TCCTAAAAAC AGGACAAGGC CGGATAAAAT
                                       27 kDa Promoter
3801 TTTTTCATGA AACGATCTTT GTAATGCAAT ATGAGTTGTT TGTAATGTCT TGTGAGCTGT AAGCATGTAT TTCGTACTCG CATGACTCA
     AAAAAGTACT TTGCTAGAAA CATTACGTTA TACTCAACAA ACATTCGACA ACACTCGACA TTCGTACACA TAGTCTACTC ATACTAGAGC CGTACTGAGT
                                       27 kDa Promoter
3901 CCGTGTTTCT TTGCACACAG AGAGGATTTG TCTTAATGTT TCTTACCCAA CAACATTTAA GGACTTATTC GGTTGCACCT GGATCGAAGG GGATCGGAAG
     GGCACAAAGA AACGTGTGTC TCTCCTAAAC AGAATTACAA AGAATGGGTT ATGGGAACTG CCTGTAAATT CCAACGTGGA CCTAGCCTCC CCTAGCCTTC
                                       27 kDa Promoter
4001 AACAAATTCT TGGAGCTTTA CATGCCAAATC TATTTAATTT TGCTGTTCTT CAACATTTAA CGTTTCCAAC CCCTTTCGAT CCAGACGTAA GCGAACAAGT TATTTATTTG
     TTGTTTAAGA ACCTCGAAAT GTACGGTTAC GTACCAACAA AGCACAAGGA GTTGTAAATT CAACAAGTTG GGGAAAGCTA GGTCTGCATT CGCTTGTTCA ATAATAAAC
                                       27 kDa Promoter
4101 AAATCGATTA AATCTCCCTC TATTTAATTT TGACTAGGAA GAGATTTAAT CGTTTCCAAC CTCTAAATTA GCAAAGGTTG GCAAAGCTA CGGCTGTCATT CGCTTGTTCA ATAATAAAC
     TTTAGCTAAT TTAGAGGGAG ATAATTAAA ACTGATCCTT CTCTAAATTA GCAAAGGTTG CCAAAGGTTG
                                       27 kDa Promoter
4201 GATACCTCTT ATTCATCTTA ATACACACAT GGTATTAAGT TGCCACTAGT CGTATGCCTG TGCATTGCCA ACGTGATCA ACGTAACGAT CGGTTTATAT TATATATATA TATATATATA
     CTATGGAGAA TAAGTAGAAT TATGTGTGTA CCATAATTCA ACGGTGATCA GCATACGGAC ACGTAACGAT GCCAATATA CTAACCAAC ACACTTATAC ATATATATAT ATATATATAT
                                       27 kDa Promoter
4301 TATATATATA TATATATATA ATATATATAT ATACTATTTA TATGATAAAT TTGTTTTAA TAAAACATAT GTTTCTATT GATTAGGTTG TGTGAATATG AGCCAACAAC CAAGTCCAAG GTTCCAAGTC
     ATATATATAT ATATATATAT TATATATATA TATGATAAAT AACAAAATT ATTGTATA CAAAAGATAA CTAACCAAC ACACTTATAC TCGGTTGTTG GTTCCAGGTC
```

FIG. 7E

```
                    BsrGI
4401 AACACTTATA CATAAATTCA CCTTATTATA TACNTAAACT CTCTTATTAT AGTAGTAAGA GAAGAGATTA TAAGAGTGCG GGTTGATTAT AAAGAAATGT
     TTGTGAATAT GTATTAAAGT GGAATAAAAC ANGTATTTGA GAGAATAATA TCATCATTCT CTTCTCTAAT ATTCATCACGC CCAACTAATA TTTCTTTACA
                                                27 kDa Promoter                                    RB
                     StuI
4501 AGGAGTTTTT TAATAATATT GACAGGCTT AAGGGCCAGA TCTTGGGCCC GGTACCCGAT CAGATTGTCG TTTCCCGCCT TCGGTTTAAA CTATCAGTGT
     TCCTCAAAAA ATTATTATAA CTGTCCGAA TTCCCGGTCT AGAACCCGGG CCATGGGCTA GTCTAACAGC AAAGGGCGGA AGCCAAATTT GATAGTCACA
       27 kDa Promoter                                                                                 RB RB                                                    ←-start RB seq
4601 TTGACAGGAT ATATTGCGGC GTAAACCTAA GAGAAAGAG CGTTTATTAG AATAATCGAA TATTTAAAG GGGCTGAAAA GGTTTATCCG TTCGTCCATT
     AACTGTCCTA TATAAGCGCC CATTTGGATT CTCTTTCTC GCAAATAATC TTAGCCT ATAAATTTTC CCCGACTTTT CCAAATAGGC AAGCAGGTAA 4701 TGTATGTGCA TGCCAACCAC AGGGTTCCCC TCGGGAGTGC TTGGCATTCC GTGCGATAAT GACTTCTGTT CAACCACCCA AACGTCGGAA AGCCTGACGA
     ACATACACGT ACGGTTGGTG TCCCAAGGGG AGCCCTCACG AACCGTAAGG CACGCTATTA CTGAAGACAA GTTGGTGGGT TTGCAGCCTT TCGGACTGCT 4801 CGGAGCCAGCA TTCCAAAAAG ATCCCTTGGC TCGTCTCGGT CGGCTAGAAG GTCGAGTGGG CTGCTGTGGC TTGATCCTC AACGCGGTCG CGGACGTAGC
     GCCTCGTCGT AAGGTTTTTC TAGGGAACCG AGCAGACCCA GCCGATCTTC CAGCTCACCC GACGACACCG AACTAGGGAG TTGGCGCAGC GCCTGCATCG 4901 GCAGCGCCGA AAAATCCTCG ATCGCAAATC CGACGCTGTC GAAAAGCGTG ATCGCTTGT CGCCTTCG GCCGACGTCC TGGCCAGTCA TCACGCGCCA
     CGTCGCGGCT TTTTAGGAGC TAGCGTTTAG GCTGCGACAG GCTTTCGCAC TAGACGAACA GCGAAAAGC CGGCTGCAGG ACCGGTCAGT AGTGCGCGGT 5001 AAGTTCCGTC ACAGGATGAT CTGGCGGGAG TTGCTGGATC TCGCCTTCAA TCCGGGTCTG TGGCGGGAAC ACCGCCCTTG TCCACGAAAA TATCCGAACG CAGCAAGATA
     TTCAAGGCAG TGTCCTACTA GACCGCCCTC AACGACCTAG AGCGGAAGTT AGCCCAGAC ACCGCCCAAG AGGTGCTTTT ATAGGCTTGC GTCGTTCTAT 5101 TCGCGGTGCA TCTTCGTCTT GCCTGGGCAG TCGCGCCGA CGCCGTTGAT GTGGACGGCG AAAAGGATCT AGGTGAAGAT CCTTTTTGAT AATCTCATGA
     AGCGCCACGT AGAGCCAGAA CGGACCCGTC AGCGCGGCT GCGGCAACTA CACCTGCCGC TTTTCCTAGA TCCACTTCTA GGAAAAACTA TTAGAGTACT 5201 CCAAAATCCC TTAACGTGAG TTTTCGTTCC ACTGAGCGTC AGACCCCGTA GAAAAGATCA CTTTTCTAGT TTCCTAGAAG TTGAGATCTT TTTTTTCTGC GCGTAACTG
     GGTTTTAGGG AATTGCACTC AAAAGCAAGG TGACTCGCAG TCTGGGGCAT CTTTCTAGT AAAAAGAGCC CGCATTAGAC 5301 CTGCTTGCAA ACAAAAAAAC CACCGCTACC AGCGGTGGTT TGTTTGCCGG ATCGAAGAGCT TTTCCGAAGG TAACTGGCTT CAGCAGAGCG
     GACGAACGTT TGTTTTTTTG GTGGCGATGG TCGCCACCAA ACAAACGGCC TAGTTCTCGA TGGTTGAGAA ATTGACCGAA GTCGTCTCGC 5401 CAGATACCAA ATACGTTCT TATGCACAAGA TCTAGTGTAG CGGTAGTTAG CCGACCACTT CAAGAACTCT GTAGCACCGC CTACATACCT CGCTCTGCTA ATCCTGTTAC
     GTCTATGGTT TATGCAAGA AGATCACAAC AGATCACATA GGCATCAATC GGCAACCAA GTTCTTGAGA CATCGTGGCG GATGATGGA TAGGACAATG 5501 CAGTGGCTGC TGCCAGTGGC GATAAGTCGT GTCTTACCGG GTTGGACTCA CTGAGATACC TACCGGATAA GCGCAGCGG TCGGGCTGAA CGGGGGGTTC
     GTCACCGACG ACGGTCACCG CTATTCAGCA CAGAATGGCC CAACTGAGT GACTCTATGG ATGGCCTATT CCGCTCGCC AGCCCGACTT GCCCCCAAG 5601 GTGCACACAG CCCAGCTGG AGCGAACGAC CTACACCGAA CTGAGATACC TACAGCGTGA GCTATGAGAA AGCGCCACGC TTCCCGAAGG GAGAAAGGCG
     CACGTGTGTC GGGTCGACC TCGCTTGCTG GATGTGGCTT GACTCTATGG ATGTCGCACT CGATACTCTT TCGCGGTGCG AAGGGCTTCC CTCTTTCCGC 5701 GACAGGTATC CGGTAAGCGG CAGGGTCGGA ACAGGAGAGC GCACGAGGGA GCTTCCAGGG GGAAACGCCT GGTATCTTTA TAGTCCTGTC GGGTTTCGCC
     CTGTCCATAG GCCATTGCC GTCCCAGCCT TGTCCTCTCG CGTGCTCCCT CGAAGGTCCC CCTTTGCGGA CCATAGAAAT ATCAGGACAG CCCAAAGCGG
```

FIG. 7F

```
5301 ACCTCTGACT TGAGCGTCGA TTTTTGTGAT GCTCGTCAGG GGGGCGGAGC CTATGGAAAA CGGCGGCCTTT TTACGGTTCC TGGCCTTTTG
     TGGAGACTGA ACTCGCAGCT AAAAACACTA CGAGCAGTCC CCCCGCCTCG GATACCTTTT GCCGGTCGTT AATGCCAAGG ACCGGAAAAC

5901 CTGGCCTTTT GCTCACATGT TCTTTCCTGC GTTATCCCCT GATTCTGTGG ATAACCGATT ACCGCCCTTG AGTGAGCTGA TACCGCTGC  CGGAGCCGAA
     GACCGGAAAA CGAGTGTACA AGAAAGGACG CAATAGGGGA CTAAGACACC TATTGGCTAA TGGCGGGAAAC TCACTCGACT ATGGCGAGCG GCGTCGGCTT

6001 CGACCGAGCG CAGGGAGTCA GTGAGCGAGG AAGCGGAAGA GCGCCTGAGT CGGTATTTTC TCCTTACGCA TCTGTGCGGT ATTTCACACC GCATATGGTG
     GCTGGCTCGC GTCCCTCAGT CACTCGCTCC TTCGCCTTCT CGCGGACTAC GCCATAAAAG AGGAATGCGT AGACACGCCA TAAAGTGTGG CGTATACCAC

6101 CACTCTCAGT ACAATCTGCT CTGATGCCGC ATAGTTAAGC CAGTATACAC TCCGCTATCG CTACGTGACT GGGTCATGGC TGCGCCCCGA CACCCGCCAA
     GTGAGAGTCA TGTTAGACGA GACTACGGCG TATCAATTCG GTCATATGTG AGGCGATAGC GATGCACTGA CCCAGTACCG ACGCGGGGCT GTGGGCGGTT

6201 CACCCGCTGA CGGGCCTGTC TGCTCCCGGC ATCCGCTTAC AGACAAGCTG TGACCGTCTC CGGAGCTGC  ATGTGTCAGA GGTTTTCACC
     GTGGGCGACT GCCCGGACAT ACGAGGGCCG TAGGCGAATG TCTGTTCGAC ACTGGCAGAG GCCCTCGACG TACACAGTCT CCAAAAGTGG

6301 GTCATCACCG AAACGCGCGA GGCAGGGGTA GATCCAACCC CTCCGCTGCT ARAGTGCAGT CGGCTTCTGA CGTTCAGTGC AGCCGTCTTC
     CAGTAGTGGC TTTGCGCGCT CCGTCCCCAT CTAGGTTGGG GAGGCGACGA TATCACGTCA GCCGAAGACT GCAAGTCACG TCGGCAGAAG

6401 TGAAAACGAC ATGTCGCACA AGTCCTAAGT TACGGCGCCC GCTGCCGCCC TGCCCTTTC  ACGGGAAAAG CTGGTCGCGT GTTTTAGTCG CATAAAGTAG
     ACTTTTGCTG TACAGCGTGT TCAGGATTCA ATGCGCTGTC CGACGGCGGG ACGGCGGGGG TGACCTTTC  GACCAGCGCA CAAAATCAGC GTATTTCATC

6501 AATACTTGCG ACTAGAACGG GCCATGAACA CGCTGGCCTG AGAGCGCCGC CTGGGCTATG CACCGACGAC CAGGACTTGA
     TTATGAACGC TGATCTGGC  CGTCGTAATG GCGACGGAC  TCTCGCGGCG GCGACGGAC  GGGCGCAGTC GTGGTGCTG  GTCCTGAACT

6601 CCAACCAACG GGCCGAACTG CACGCGCCCG GCTGTTTTCC GAGAAGATCA CCGGCACCAG CGGCGACCGC CCGAGCTGG  CCAGGATGCT
     GGTTGGTTGC CCGGCTTGAC GTGCGCGGGC CGACAAAAGG CTCTTCTAGT GGCCGTGGTC GCCGCTGGCG GGCTCGACC  GGTCCTACGA

6701 TGACCACCTA CGCCCTGGCG AGTGACGACG CCTGGCAGAG ACACCACCAC GCGGCCCGGC GCGCGAGGCG TGAAGTTTGG CCCCGCCCT  TTGCCGAGCA CATCCAGGAG
     ACTGGTGGAT GCGGGACCGC TGCACACTG  GGACCGTCTC GGACCGGCG  CGGCGGACCG CGCTCCGGC  ACTTCAAACC GGGGGCGGA  AACGGCTCGC GTAGGTCCTC

6801 GCCGGCGCGG GCCTGCGTAG CCTGGCAGGA CCGTGGGGCG ACACCACCAC GCGGCCCGGC CGCATGGTGT TGACCGTGTT CGCCGGCATT GCCGAGTTGG
     CGGCCGCGCC CGGACGCATC GGACCGTCCT GGCACCCGGC TGTGGTGGTG CGCCGGGCCG ACTGGCACAA AGTGGCACAA ACTGGCACAA CGGCTCAAGC

6901 AGCGTTCCT  AATCATCGAC CGCAACCGGA CGGGGCGCGA GGCCGCCAAG GCGCGAGGCG ACTTCAAACC CCCCGCCCT  ACCCTCACCC CGGCACAGAT
     TCGCAAGGGA TTAGTAGCTG GCGTTGGCCT CGCCCGCGCT CCGGCGGTTC CGCTCCGGC  ACTTCAAACC GGGAGTGGG  GCCGTGTCTA

7001 CGCGCACGCC TGGACCAGGA AGGCCCACC  GTGAAAGAGG CACTTTCTCC GCTTGGCGTG CATCGCTCGA CCCTGTACCG CGCACTTGAG
     GCGCGTGCGG AGTCGGACT  TCCGGGGTGG CGGCGGGGC  CACTTTCTCC CGAACCGCAC GTAGCGAGCT GGGACATGCC GCGTGAACTC

7101 CGCAGCGAGG AAGTGAACGG AGGCGGGGCC AGGCGGGGCC CCGGAGAGG  GTGCCTTCCG TGAGGACGCA TTGACCGCA  GGGGCGCCC  GAGAATGAAC
     GCGTCGCTCC TTCACTTGCC TCCGGCGGG  TCCGGAAGGC GGCCTCCGGG ACTCCTGCGT AACTGGCTCC CCGCGGGCG  CTCTTACTTG

7201 GCCAAGAGGA ACAAGCATGA GGACGCCACA AACCGCAGCG TTTTCATTAC CGAAGAGATC TGATCGGGGC CGGGCGTG
     CGGTTCTCCT TGTTCGTACT TTGGCGTGGT CTGCCGGTT  AAAAGTAATG GCTTTCTCAG ACTAGCGCCG GCCCATGCAC

7301 TTCGAGCCGC CCCGCCACGT CTCAACCGTG CGGCTGCAAG AAATCCTGGC CGGTTTGTCT GATGCCAAGC TGGCGGCCTG TTGGCCGCTG
     AAGCTCGGCG GGGGCGGTGC GAGTTGGCAC GCCGACGTAC TTTAGGACCG GCCAAACAGA CTACGGTTCG AGCCCGGAC  AACGGCGAC
```

FIG. 7G

```
7401: AAGAACCGA GCGCCGCCGT CTAAAAAGGT GATGTGTATT TGAGTAAAAAC AGCTTGCGTC ATGCGGTCGC TGCGTATATG ATGGGATGAG TAAATAAACA
      TTCTTTGGCT CGCCGGGGCA GATTTTTCCA CTACACATAA ACTCATTTTG TCGAACGCAG TACGCCAGCG ACGCATATAC TACCCTACTC ATTTATTTGT

7501: AATACGCAAG GGGAACGCAT GAAGGTTATC GCTGTACTTA ACCAGAAAGG TGGTCTTTCC GCCCAGTCCA AAGACGACCA TCCAACCCA TCTAGCCCGC GCCCTGCAAC
      TTATGCGTTC CCCTTGCGTA CGACATGAAT CGACATTAG TGGTCTTTCC GCCCAGTCCG AGCGTTGGGT TTCTGCTGGT AGATCGGGCG CGGGACGTTG

7601: TCGCCGGGC CGATGTTCTG TTAGTCGATT CCGATCCCA GGGCAGTGCC CGGGATTGGG CGGCCCGTGG CCGCTAACCC TTGTCGGCAT
      AGCGGCCCG GCTACAAGAC AATCAGCTAA GGCTAGGGT CCCGTCACGG GCCCTAACGC CCTTCTAGTT GGCCATTGGC AACAGCCGTA

7701: CGACCGCCCG ACGATTGACC GCGACATCGGC CGGCCGCGACT TCGTAGTGAT CGACGGAGCG CCCCAGGCGG CGGACTTGGC TGTGTCCGG
      GCTGGCGGC TGCTAACTGG CGCTGCACTT CCGGTAGCCG GCCGGGCGATCTGA AGCATCACTA GCTGCCTCGC GGGGTCCGCG GCCTGAACCG ACACAGCGC

7801: ATCAAGCCAG CCGACTTCGT GCTGATTCCG GTGCAGCCAA CATATGGGCC GCCCTTACGA ACCGCGACC TGGTAAGCAG CGCATTGAGG
      TAGTTCCGTC GGCTGAAGCA CGACTAAGGC CACGTCGGTT CGGGAATGCT GTATACCCGG TGGGGCTGG ACCACTCGA CCAATTCGTC GCGTAACTCC

7901: TCACGGATGG AAGGCTACAA GCGGCCTTTG TCGTGTCGCG GGCACGCGCA CCGTGCGCGT TCGGCGGTGA GGTTGCCGAG GGCTGCGCG GGTACGAGCT
      AGTGCCTACC TTCCGATGTT CGCCGGAAAC AGCACAGGCG CCGCTAGTTT CCGTGCGCGT AGCCGCCCTC CCAACGGCCT CCGCACGCGC CCATCCTCGA

8001: GCCCATTCTT GAGTCCCGTA TCAACGCAGC CGTGAGCTAC CCAGGCACTG CGCGCGCGG CACAACCGTT CTTGAATCAG CGACGCTGCC
      CGGGGTAAGAA CTCAGGGCAT AGTGCGTCGC GCACTCAGCT GGTCCGTGAC GGGCGGGCC GTGTTGGCAA GAACTTAGTC TGGGCTCCC GCTGGACGCG

8101: CGCGAGGTCC AGGGCGCTGG CGCTGAAATT AAATCAAAAC TCATTTGAGT TAATGAGGTA AAGAGAAAAT GAGCAAAAGC ACAAACACGC TAAGTGCCGG
      GCGCTCCAGG TCCGGCGACC GCGACTTTAA TTTAGTTTTG AGTAAACTCA AATACTCCAT CTCGTTTTCG TGTTGTGCG ATTCACGGCC

8201: CCGTCCGAGC GCACCGCAGCA GCAAGGCTGC AACGTTGGCC AGCCTGGCAG ACACGCCAGC CATGAAGCGG GTCAACTTTC AGTTGCCGGC GGAAGATCAC
      GGCAGGCTCG CGTGCGTCGT CGTTCCGACG TGCAACCGG TCGGACCGTC TGTGCGGTCG GTACTTCGCC CAGTTGAAAG TCAACGGCCG CCTTCTAGTG

8301: ACCAAGCTGA AGATGTACGC GGTAACGCCAA TTACCGAGCT GCTATCTGAA TACATGCGCG AGCTACCAGA GAAATGAGC AAATGAATAA
      TGGTTCGACT TCTACATGCG CCATGCGGTT CGTTCTCGT AATGATGTCA CGATAGACTT ATGTAGGCGC TCGATGGTCT CATTTACTCG TTTACTTATT

8401: ATGAGTAGAT GAATTTAGC GGCTAAAGGA GCGGCATGG AAAATCAAGA ACAACCAGGC ACCGACGCCG TGGAATGCCC CATGTGTGGA GGAACGGCCG
      TACTCATCTA CTTAAAATCG CCGATTTCCT CCGCGGTACC TTTAGTTCT TGTTGGTCCG TGGCTGCGG ACTTACGGG GTACACACCT CCTTGCCCGG

8501: GTTGGCCAGG CGTAAGCGGC GGTACGCCAA TGGGTTGTCT GCCGGCCCTG CAATGGCACT GGAACCCCA AGCCCGGAGGA ATCCGGCTGA ACCATCCGGC
      CAACCGGTCC GCATTCGCCG CCATGCGGTT CGGACTCGT ACCCAACAGA CGGCCGGGAC GTTACCGGGA CCTTGGGGGT TCGGGCTCCT TAGGCGAGTT TGGTAGGCCG

8601: CCGGTACAAA TCGGGCGGC GCTGGGTGAT GACCTGGTGG AGAAGTTGAA TCTTCAACTT GCGGGCGCAG CGGGGTCTG CGAAGGCAGAA CGAGGGCCCG GCACGGCCCG
      GGCCATGTT AGCCCGCCG CGACCCACTA CTGGACCACC TCTTGCAACTT CGCCCGCGTC CGGGGTCG GCTTGCGTA GCTCCGTCTT CGTCGGGGC

8701: GTGAATCGTG GCAAGCGGCC GCTGATCGAA TCCGCAAAGA ATCCCGGCAA GTCGATTAGG CCGGTTGCGC CCGGTTGCGCGC GTCGATTAGG AAGCCGACGA AGGGCGACGA
      CACTTAGCAC CGTTCGCCGG CGACTAGCTT AGGGGTTCT TAGGGCCGTT CAGCCAGCG GCCACGCGG CAGCTAATCC TTCCGCGGGT TCCGCTGCT

8801: GCAACCAGAT TTTTTCGTTC CGATGCTCTA TGACCTGGGC ACCCGCGGATA GTCGGAGCAT CATGGACGTG CATGGACGTG GCCCTTTCC GTCGTGACCGA GCGTGACCGA
      CGTTGGTCTA AAAAAGCAAG GCTACGAGAT ACTGCACCCG TGGGCGCTAT CAGCGCAGG CGCAAAAGG GTACCTGCAC CAGACAGCTT CGCACTGGCT

8901: CGAGCTTGCG AGGTGATCGC CTTACGACTC CCTAGACGGC AGTAGAGGT TTCCGCAGG AGGGTCCGG CCCGGCCCG CCCGGCCCGT TGGCGAGTGT GACCTGGTTAC
      GCTCGACCCG TCCACTAGGC GATGCTCGA GGTCTAGATCC TGCATCCCA GGTCTCCGAA AAGGGGGTCC GGCCGGGCCG GCCGGGCCGT ACCGCTCACA CTGGACCATG
```

FIG. 7H

```
9001  TGATGGCGGT TTCCCATCTA ACCGATCCA TGAACCGATA CGGGGAAGGG AAGGGAGACA AGCCGCGCCG CGTGTTCCGT CCACACGTTG CGGACGTACT
      ACTACCGCCA AAGGCTAGAT TGGCCTTAGGT ACTTGGCTAT GGCCCCTTCCC TTCCCTCTGT TCGGGCCCGG GCACAAGGCA GGTGTGCAAC GCCTGCATGA

9101  CAAGTTCTGC CGGCGAGCGC ATGGCGAAAA GCAGAAAGAC AAACCTGCAT TCGGTTAAAC ACCACGCACG TTGCCATGCA GCGTACGAAG
      GTTCAAGACG GCCGCTCGGC TACCGCTTTT CGTCTTCTG CTTGGACCATC AGCCAATTTG TGGTGCGTGC AACGGTAGT CGCATGCTTC

9201  AAGGCCAAGA ACGGGCCGCT GGTGACGGTA TCCGAGGGTG AAGCCTTGAT TAGCCGCTAC AAGATCGTAA AGAGCGAAAC CGGGCGGCGG GAGTACATCG
      TTCCGGTTCT TGCCCGGCGA CCACTGCCAT AGGCTCCCAC TTCGGAACTA ATCGGCGATG TTCTAGCATT TCTCGCTTTG GCCCGCCGC CTCATGTAGC

9301  AGATCGAGCT AGCTGATTGG ATGTACCCGG AGATCACAGA AGGCAAGAAC CCGGACGTGC TGACGGTTCA CCCCGATTAC TTTTGATCG ATCCGGACT
      TCTAGCTCGA TCGACTAACC TACATGGGCC TCTAGTGTCT TCCGTTCTTG GGCCTGCACG ACTGCCAAGT GGGGCTAATG AAAAACTAGC TAGGGCCTA

9401  CGGCCGTTTT CTCTACCGCC TGGCACGCCG CGCGCGAAGC AAGGCAGAAG GTTCAAGACG ATCTACGAAC GCAGTGGCAG CGCCGGAGAG
      GCCGGCAAAA GAGATGGCGG ACCGTGCGGC GCGCGCTTC TTCCGGTCTTC CAAGTTCTGC TAGATGCTTG CGTCACGGTC GCGGCCTCTC

9501  TTCAAGAAGT TCTGTTTCAC CGTGCGCAAG CTGATCGGGT CAAATGACCT GCCGGAGTAC GATTTGAAGG AGGAGGCGGG GCAGGCTGGC CCGATCCTAG
      AAGTTCTTCA AGACAAAGTG GCACGCGTTC GACTAGCCCA GTTTACTGGA CGGCCTCATG CTAAACTTCC TCCTCCGCCC CGTCCGACCG GGCTAGGATC

9601  TCATGCGCTA CCGCAACCTG ATCGAGGGCG AAGCATCCGC TGTACGGAGC AGATGCCTAGG GCAAATTGCC CGGACCAAGCC CTAGCCAGGG AAAAGGTGC
      AGTACGCGAT GGCGTTGGAC TAGCTCCGC TTCGTAGGCG ACAAGGATT ACAGCCTG TCTACGATCC CGTTTAACGG GATCGTCCC TTTTCCAGC

9701  AAAAGGTCTC TTTCCTGTGG ATAGCACGTA CATTGGGAAC CCAAAGCCGT ACATTGGGA CCGGAACCCG TACATTGGGA ACCCAAAGCC GTACATTGG
      TTTTCCAGAG AAAGGACACC TATCGTGCAT GTAACCCTTG GGTTTCGGCA CCAAGCCCT GGCCTTGGGC ATGTAACCCT TGGGTTTCGG CATGTAACCCT

9801  AACCGGTCAC ACATGTAAGT GACTGATATA AAAGAGAAAA TTCCGCCTAA AACTCTTTAA AACTTATTAA ACCCGCCTGG
      TGGCCAGTG TGTACATTCA CTGACTATAT TTTCTCTTTT AAGGCGGATT TTGAGAATTT TGAATAATTT TGGGCGGACC

9901  CCTGTGCATA ACTGTCTGGC CAGCGCACAG CCGAAGAGCT GCAAAAAGCG CCTACCCTTC GGTCGCTGCG CTCCCCTACGC CCGGCGCTT CGGCGTCGCC
      GGACACGGTAT TGACAGACCG GTCGCGTGTC GGCTTCTCGA CGTTTTTCGC CGATGGGAAG CCAGCGACGC GAGGGATGCG GGGCGGCGAA GCGGCAGTCGG

10001 TATCCGGGCC GCTCAAAGCT CAAAAAATGG CCGGATGCC TGGCCTACGG CCAGGATGCC TACCAGGGCG CGGACAAGCC CGGCGGCGCG CGCGGGGCA
      ATAGCCCCGG CGAGTTCCGA GTTTTTACCG GGCTACGGG ACCGGATGCC ATGGTCCCGC GCCGCCTCGG CCGGCCAGCG GCCGCCGCG GCCGCGCCGT

10101 CATCAAGGCA CCGGTGGGTA TGCCTGACGA TGCGGTGGAGA CCGAAACCTT GTGCTCGGTC ACAGAAATGC CTCGACTTGC CTGCTGCCA
      GTAGTTCCGT GGCCACCCAT ACGGACTGCT ACGGACTCCT GGCTTTGGAA CGCGAGCAAG TGTCTTTACG GAGCTGAAGC GACGACGGGT

10201 AGGTTGCCGG GTGACGGCACA CCGGTGGCGCA GGATGAAGGC ACGAACCCAG TGGACATAAG CCTGTTCGGT TGTAAGCTG TAATGCAAGT AGCGTATGCG
      TCCAACGGCC CACTGGCGTT GGCCACCCGT CCTACTCCG TGCTTGGGTC ACCTGTTATTC GGACAAGCCA AGCATTCGAC ATTACGTTCA TCGCATACGC

10301 CTCACGCAAC TGTGCCAGAA CCTTGACCGA ACCAGCGCGA ACGCAGCGCG GGTAACGGCG CAGTGCGCGT TTCATGGCT TGTTATGACT GTTTTTTGG GGTACAGTCT
      GAGTGCGTTG ACCAGGTCTT GGAACTGGCT TGCGTCGCCA TGCGTCGCGC CCATTGCCGC GTCACGCGCA AAAGTACCGA ACAATACTGA CAAAAAACC CCATGTCAGA

10401 ATGCCTCGGG CATCCAAGCA GCAAGGCGGT TACGCCGTGG TACGCGCGGT TACGCCGTGG GTCGATGTTT GATGTTATGG AGCAGCAAG ATGTTACGCA GCAGGCAGT CGCCCTAAAA
      TACGGAGCCC GTAGTTCGT CGTTCGCCA ATGCGGCCA CAGCCAATCC CAGCGACGAA CTACAATACC TCGTCGTTGC TACAATGCGT GTCCGGTCA GCGGGATTTT

SpecR

10501 CAAAGTTAAA CATCATGAGG GAAGCGGTGA TCGCCGAAGT ATCGACTCAA CTATCAGAGG TAGTTGGCGT CATCGAGCGC CATCTCGAAC CGACGTTGCT
      GTTTCAATTT GTAGTACTCC CTTCGCCACT AGCGGCTTCA TAGCTGAGTT GATAGTCTCC ATCAACCGCA GTAGAGCTTG GCTGCAACGA
```

FIG. 7I

```
                                                                                              SpecR
10601 GGCCGTACAT TTGTAAGGCT CCGCAGTGGA TGGCGGCCTG AAGCCACACA GTGATATTGA TTTGCTGGTT ACGGTGACCG TAAAGCTTGA TGAAACAACG
      CCGGCATGTA AACATCCGA GGCGTCACCT ACCGCCGGAC TTCGGTGTGT CACTATAACT AAACGACCAA TGCCACTGGC ATTCGAACT ACTTGTTGC SpecR
10701 CGGCGAGCTT TGATCAACGA CCTTTTGGAA ACTTCCGCTT CCCCTGGAGA GAGGCAGATT CTCCCGCTG TAGAGTCAC CATTGTTGTG CACGACGACA
      GCCGCTCGAA ACTAGTTGCT GGAAAACCTT TGAAGCCGAA GGGGACCTCT CTCCGTCGAC GAGGCGCGAC ATCTTCAGTG GTAACAACAC GTGCTGCTGT SpecR
10801 TCAATCCGTG GGGTTATCCA GCTAAGCGCG AACTGCAATT TGGAGAATGG CAGGCCAATG ACATCTTGC AGGTATCTTC GAGGCAGCCA CGATCGACAT
      AGTAAGGCAC CCGAATAGGT CGATTCGCGC TTGACGTTAA ACCTCTTACC GTCGGTTAC TGTAAGAACG TCCATAGAAG CTCGGTCGGT GCTAGCTGTA SpecR
10901 TGATCTGGCT ATCTTCTGA CAAAAGCAAG AGAACATAGC GTTGCTTGG AACGGAGGAA CTCTTTGATC CGGTTCCTGA ACAAGATCTA
      ACTAGACCGA TAGAACGACT GTTTTCGTTC TCTTGTATCG CAACGGAACC ATCCAGGTCG CCGCTCCTT GAGAAACTAG GCCAAGGACT TGTCCTAGAT SpecR
11001 TTTGAGCGC TAAAATAAAC CTTAACGCTA TGGAACTCGC GGCTGGCGAT GAGCGAAATG TAGTGCTTAC GTTGTCCCGC ATTTAGTACA
      AACTCCCGCG ATTTACTTTG GAATTCGGAT ACCTTGAGCG CCGACTGAC CCGACCGCTA CTCGCTTTAC ATCACGAATG CAACGGGCG TAAACCATGT SpecR
11101 GCGGAGTAAC GGGCAAAATC GCGCCGAAGG ATGTCGCTGC CGACTGGCCA ATGGAGCGCC TGCCGGCCCA GTATCAGCCC GTCATACTTG AAGCTAGACA
      CGCCTCATTG GCCGTTTTAG CGCGGCTTCC TACACGCACG GCTGACCGGT TACCTCCGGG ACGGCCGGGT CATAGTCGGG CAGTATGAAC TTCGATCTGT SpecR
11201 GGCTTATCTT GGACAAGAAG AAGATGCCTT GGCCCTGCGC GCAGATCAGT TGGAAGAATT TGTCCACTAC GTGAAAGCCG AGATCACCAA GGTAGTCGGC
      CCGAATAGAA CCTGTTCTTC TTCTAGGAGT GCCGGAAGC CCGGAGCGCG CGTCTAGTCA ACCTTCTTAA ACAGGTGATG CACTTTCCGC TCTAGTGGTT CCATCAGCCG SpecR
11301 AAATAATAGC TAACAATTCG TTCAAGCCGA CGGCCGTTCG CGGCGCGGCT TAACTCAAGC ACAAATTGGG AGATATATCA TGAAAGGCTG GCTTTTCTT GTTATCGCAA
      TTTATTATCG ATTGTTAAGC AAGTTCGGCT GCCGGCAAGC GCCGCGCCGA ATTGAGTTCG CAATTACGT GATTCGTGTA TTAACGAGTG ACTTCCGAC CGAAAAGAA CAATAGCGTT 11401 TCAGGTCAAG TCTGTTTTA TTATTTTAA GCGTGCATAA TAAGCCCTAC ACAAATTGGG TGTTTAACCC TCTATAATAGT TGTACCTGC GTTCAAATAC TTTGCCGCC TGTTGCCGCC
      AGTCCAGTTC AGACAAAAAT AATAAAATT CGCACGTATT ATTCGGATG TGTTTAACCC AGATATATCA TGAAAGGCTG ACATGGACG CAAGTTATG AAACGGTAGC ACAACGGCCG 11501 TAGTTGGCGA AGTAATGCCA ACATAGCTTG CTTGGTCGGT CGCGGTCGGA GTCGGCCTGA GTTCAAATAC TTTGCCATCG TGTTGCCGC TGGTGCCGGC
      ATCAACCGCT TCATTACGGT TGTATCCAAC GAACCAGCAA GAACCAGCCT CAGCCGAGCT AACATGGACG CAAGTTATG AAACGTTAGC ACAACGGCG 11601 CTGCCCGGTG CTGGTCGCTA TCTCACGGAT CGACTGCTTC TCTCGCAACG CCATTGCACG GATGATGTTT AAAAGTCCCA TGTGATCAC TCCGTGCCC
      GACGGGCCAC GCACCGAGCT AGAGTGCCTA GCTGACGAAG AGAGCGTTGC GGTAACGTGC CTACTACAAA TTTTCAGGGT ACACCTAGTG AGGCAACGGG Start LB seq→
11701 CGTCGCTCAC CGTGTGGGGG GGAAGTGCA CATGGCTCAG TTCGCATT CCTAACCGGC GTAGAACCA ACATGCAAGC
      GCAGCGAGTG GCACACCCG CCTTCCACGT GTACCGAGTC AAGAGTACC TTTAATAGAC GGATTGGCCG AGTCAAGACG CATCTTGGT TGTACTTCG

11801 TCCACCGGGT GCAAAGCGGC AGCGGC
      AGGTGGCCCA CGTTTCGCCG TCGCCG
```

```
GnDI     --MSADFGLIGLAVMGQNLILNAADHGFTVCAYNRTQSKVDHFLANEAK---GKSIIGATSI
PGD1     MALTRIGLAGLAVMGQNLALNIAEKGFPISVYNRTTSKVDETVQRAKAEGNLPVYGFHDP
PGD1mut  MALTRIGLAGLAVMGQNLALNIAEKGFPISVYNRTTSKVDETVQRAKAEGNLPVYGFHDP
          : :** ********* ** *:;**  ;;,**** ****,:, ,      :* ,:*

GnDI     EDFISKLKRPRKVMLLVKAGAPVDALINQIVPLLEKGDIIIDGGNSHFPDSNRRYEELKK
PGD1     ASFVKSIQKPRVVIMLVKAGAPVDQTIATLAAHLEQGDCIIDGGNEWYENTERREKAMEE
PGD1mut  ASFVKSIQKPRVVIMLVKAGAPVDQTIATLAAHLEQGDCIIDGGNEWYENTERREKAMEE
          .*::..:::** *:;********** *  ;*. **:** ******. : :::** : :::

GnDI     KGILFVGSGVSGGEEGARYGPSLMPGGSEEAWPHIKNIFQSISA--KSDGEPCCEWVGPAG
PGD1     RGLLYLGMGVSGGEEGARNGPSLMPGGSFEAYKYVEDIVLKVAAQVPDSGPCVTYIGKGG
PGD1mut  RGLLYLGMGVSGGEEGARNGPSLMPGGSFEAYKYVEDIVLKVAAQVPDSGPCVTYIGKGG
          :*:*::* ********** ******** **:  ::::*. ,::*   *. **  ::*  .*

GnDI     AGHYVKMVHNGIEYGDMQLICEAYDIMKRLGGFTDKEISDVFAKWNNGVLDSFLVEITRD
PGD1     SGNFVKMVHNGIEYGDMQLISEAYDVLKSVGKLTNSELHQVFSEWNKGELLSFLIEITAD
PGD1mut  SGNFVKMVHNGIEYGDMQLISEAYDVLKSVGKLTNSELHQVFSEWNKGELLSFLIEITAD
          :*:;:**************.****;;* :* ;*::*:*; :**:;**:* * ***;*** *

GnDI     ILKPDDVDGK-PLVEKIMDTAGQKGTGKNTAINALDLGMPVTLIGEAVFARCLSALENER
PGD1     IFGIKDEHGDGYLVDKVLDKTGMKGTGKWTVQQAAELSVAAPTIEASLDSRFLSGLKDER
PGD1mut  IFGIKDEHGDGYLVDKVLDKTGMKGTGKWTVQQAAELSVAAPTIEASLDSRFLSGLKDER
          *:  :,*  .*.  **:*::*,:* ******, :* :*.:  ,    *  :: :* **.**:**

GnDI     IRASKVLPGPEVPKDAVKDREQFVDDLEQALYASKIISYAQGFMLIREAAATYGWKLNNP
PGD1     VEASKIFQGDYYSTGSPVDKAQLVEDVRQALYASKICSYAQGMNIIKAKSAEKGWGLNLG
PGD1mut  VEASKIFQGDYYSTGSPVDKAQLVEDVRQALYASKICSYAQGMNIIKAKSAEKGWGLNLG
          ;.***;; *     ..; *: *;*:*;.********* *****; ;*; :*  ** **

GnDI     AIALMWRGGCIIRSVFLGQITKAYREEPDLENLLFNKFFADAVTKAQSGWRKSIALATTY
PGD1     ELARIWKGGCIIRAIFLDRIKKAYDRNPGLASLLVDPEFAQEIMDRQAAWRRVVCLAINN
PGD1mut  ELARIWKGGCIIRAIFLDRIKKAYDRNPGLASLLVDPEFAQEIMDRQAAWRRVVCLAINN
          ;*  ;*;******;;***,;*,***  ;,*,*  ,**,: ***; :  ,  *:,**; :,** .

GnDI     GIPTPAFSTALSFYDGYRSERLPANLLQAQRDYFGAHTFRVLP-----------------
PGD1     GVSTPGMSASLAYFDSYRRDRLPANLVQAQRDYFGAHTYERVDMPGSFHTEWFKIARNIS
PGD1mut  GVSTPGMSASLAYFDSYRRDRLPANLVQAQRDYFGAHTYERVDMPGSFHsphrmvqdcaq
         *;  **.:** ;:*;::*,** ;******;**********,  :

GnDI     ------ECASDNLPVDKDIRINWTGHGGNVSSSTYQA
PGD1     NN-----------------------------------
PGD1mut  hl██████████████████████████---------
```

FIG. 8

```
GnDI     --MSADFGLIGLAVMGQNLILNAADHGFTVCAYNPTQSKVDRFLANEA---KGKSIIGATSI
PGD2     MALTRIGLAGLAVMGQNLALNIAEKGFPISVYNRTTSKVDETVQRAKVEGNLPVFGFHDP
PGD2mut  MALTRIGLAGLAVMGQNLALNIAEKGFPISVYNRTTSKVDETVQRAKVEGNLPVFGFHDP
           :** ********** ** *:;** ...**** ****..       ..:*  .

GnDI     EDFISKLKRPRKVMLLVKAGAPVDALINQIVPLLEKGDIIIDGGNSHFPDSNRRYEELKK
PGD2     ASFVSSIQKPRVVIMLVKAGAPVDQTIATLAAHLDQGDCIVDGGNEWYENTERREKAMEE
PGD2mut  ASFVSSIQKPRVVIMLVKAGAPVDQTIATLAAHLDQGDCIVDGGNEWYENTERREKAMEE
          .*:*.::;** *;;********** *   :.  *::** *;****.  : :;:** : :::

GnDI     KGILFVGSGVSGGEEGARYGPSLMPGGSEEAWPHIKNIFQSISA-KSDGEPCCEWVGPAG
PGD2     RGLLYLGMGVSGGEEGARNGPSLMPGGSFEAYKYIEDILLKVAAQVPDSGPCVTYIGKGG
PGD2mut  RGLLYLGMGVSGGEEGARNGPSLMPGGSFEAYKYIEDILLKVAAQVPDSGPCVTYIGKGG
         ;*;::* ********** ********** **; ;*;;;* .;;:*   *,.** ::* .*

GnDI     AGHYVKMVHNGIEYGDMQLICEAYDIMKRLGGFTDKEISDVFAKWNNGVLDSFLVEITRD
PGD2     SGNFVKMVHNGIEYGDMQLIAEAYDVLKSVGKLTNSELHQVFSEWNKGELLSFLIEITAD
PGD2mut  SGNFVKMVHNGIEYGDMQLIAEAYDVLKSVGKLTNSELHQVFSEWNKGELLSFLIEITAD
         ;*:;**************** ****;:* ;* ;*;,*;  ;**;;**;* * ***;*** *

GnDI     ILKFDDVDGK-PLVEKIMDTAGQKGTGKWTAINALDLGMPVTLIGEAVFARCLSALKNER
PGD2     IFGIKDDKGEGYLVDKVLDKTGMKGTGKWTVQQAAELSVAAPTIEASLDSRFLSGLKDER
PGD2mut  IFGIKDDKGEGYLVDKVLDKTGMKGTGKWTVQQAAELSVAAPTIEASLDSRFLSGLKDER
         *; ;.* .,*;  **:*;;*.;* ******,.;* ;*;,. .  *  ;; ;* **,**;**

GnDI     IRASKVLPGPEVPKDAVKDREQFVDDLEQALYASKIISYAQGFMLIREAAATYGWKLNNP
PGD2     VEASKIFQGDYST-GLPVDKAQLIEDVRQALYASKICSYAQGMNIIKAKSSEKGWGLNLG
PGD2mut  VEASKIFQGDYST-GLPVDKAQLIEDVRQALYASKICSYAQGMNIIKAKSSEKGWGLNLG
         ;.***;; *     . *; *;;;*;;.********* *****; ;*; ;; ** **

GnDI     AIALMWRGGCIIRSVFLGQITRAYREEPDLENLLFNKFFADAVTKAQSGWRKSIALATTY
PGD2     ELARIWKGGCIIRAIFLDRIKKAYDRNPNLANLLVDPEFAQEIIDRQAAWRRVVCLAINN
PGD2mut  ELARIWKGGCIIPAIFLDRIKKAYDRNPNLANLLVDPEFAQEIIDRQAAWRRVVCLAINN
          ;* ;*;*****;;** ;**,;* *** ,;  *,;**  ;  .  *;,**;  ;,** .

GnDI     GIPTPAFSTALSFYDGYRSERLPANLLQAQRDYFGAHTFxVLPECASDNLPVDKDIRINW
PGD2     GVSTPGMSASLAYFDSYRRDRLPANLVQAQRDYFGAHTYExVDMP--------GSFHTEW
PGD2mut  GVSTPGMSASLAYFDSYRRDRLPANLVQAQRDYFGAHTYtVDMP--------GSFHTEW
         *; **.:*;;*;;;*,** ;****** ;*************;. ;             .;* ;*

GnDI     TGHGGNVSSSTYQA
PGD2     FKIARNSKI-----
PGD2mut  FKIARNSKI-----
          . *. .
```

FIG. 10

FIG. 17
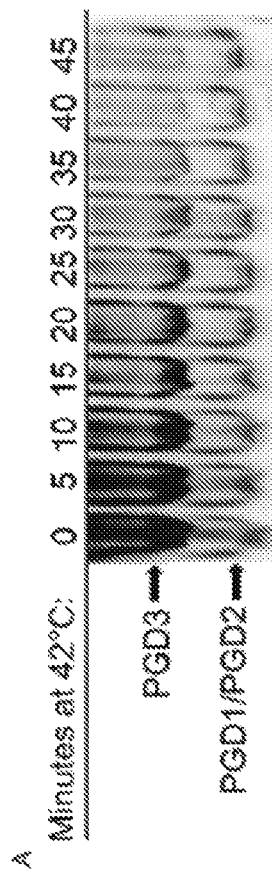
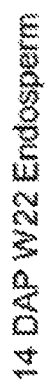
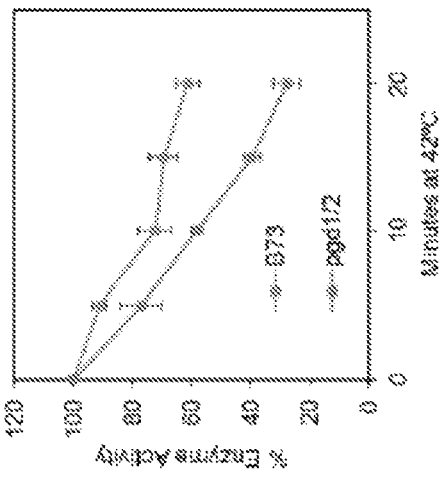
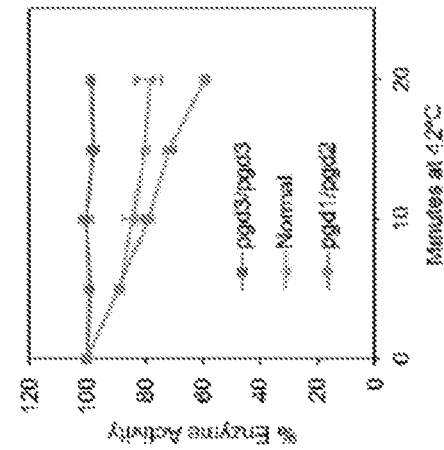

```
Maize-PGD3    MASPAPASPAAAAAHCPPPRIGLAGLATMGQNLALNIAEKGFPISVYNRTaaKVDsTLSR
Maize-PGD1    ---------------MALTRIGLAGLAVMGQNLALNIAEKGFPISVYNR
Maize-PGD2    ---------------MALTRIGLAGLAVMGQNLALNIAEKGFPISVYNR
                             *******.*************************;;***.*;.*

Maize-PGD3    ArDEGSLPVLGHPDPRGFVLSLARPRAVVLLVQAGPAVDATIQALSPYLEPGDAIVDGGN
Maize-PGD1    AKAEGNLPVYGPHDPASFVKSIQKPRVVIMLVKAGAPVDQTIATLAAHLEQGDCIIDGGN
Maize-PGD2    AKVEGNLPVFGPHDPASFVSSIQKPRVVIMLVKAGAPVDQTIATLAAHLDQGDCIVDGGN
              *;.**.***.*;.**..**..;**.*;;**;**.**.**.;*;.*;.**.*;****

Maize-PGD3    EWYQNTERRIQEAAARGVLYLGMGVSGGEEGARNGPSLMPGGSADAYANIRDILQKAAAQ
Maize-PGD1    EWYENTEPREKAMEERGLLYLGMGVSGGEEGARNGPSLMPGGSFEAYKYVEDIVLKVAAQ
Maize-PGD2    EWYENTERREKAMEERGLLYLGMGVSGGEEGARNGPSLMPGGSFEAYKYIEDILLKVAAQ
              ***;****.  ;    **;************************;**  ;;**;*;***

Maize-PGD3    --TEDGACVTFVGPGGAGNFVKMVHNGIEYGDMQLIAEAYDVLRRLGGLSNSEIADVFAEW
Maize-PGD1    VPDSGPCVTYIGKGGSGNFVKMVHNGIEYGDMQLISEAYDVLKSVGKLTNSELHQVFSEW
Maize-PGD2    VPDSGPCVTYIGKGGSGNFVKMVHNGIEYGDMQLIAEAYDVLKSVGKLTNSELHQVFSEW
                ;.*  ***;;*  **;*****************;******;  ;*  *;***;  ;**;**

Maize-PGD3    NRGELESFLVQITADIFTVADPLDGSGSGGGALVDRILDKTGMKGTGKWTVQQAAELAVA
Maize-PGD1    NKGELLSFLIEITADIFGIKDE-----HGDGYLVDKVLDKTGMKGTGKWTVQQAAELSVA
Maize-PGD2    NKGELLSFLIEITADIFGIKDD-----KGEGYLVDKVLDKTGMKGTGKWTVQQAAELSVA
              *;***.***;;******.;.*        *.*.***;;*;**************;**

Maize-PGD3    APTIAASLDGRyLSGLKDERVAAAGVLEEEGMPAGLLETVNVDKKVLVDPVRQALYASKI
Maize-PGD1    APTIEASLDSR         VEASKIFQGDYYSTG-----  PVDKAQLVEDVRQALYASKI
Maize-PGD2    APTIEASLDSR         VEASKYFQGDY-STG----LPVDKAQLIEDVRQALYASKI
              ****.****.*          *;;;;;  ;   ;*   ***  *;;  **********

Maize-PGD3    CSYAQGMNLLRAKSVEKGWNLNLAELARIWKGGCIIRAKFLDRIKsAYDRNPELANLIVD
Maize-PGD1    CSYAQGMNIIKAKSAEKGWGLNLGELARIWKGGCIIRAIFLDRIKKAYDRNPGLASLLVD
Maize-PGD2    CSYAQGMNIIKAKSSEKGWGLNLGELARIWKGGCIIRAIFLDRIKKAYDRNPNLANLLVD
              ********;;;***.*****.*** .***********.******  ******  **.;;**

Maize-PGD3    REFAREMVQRQNAWRWVVARAVEAGISTPGMTASLSYFDTYRSSRLPANLIQAQRDLFGA
Maize-PGD1    PEFAQEIMDRQAAWRRVVCLAINNGVSTPGMSASLAYFDSYPRDRLPANLVQAQRDYFGA
Maize-PGD2    PEFAQEIIDRQAAWRRVVCLAINNGVSTPGMSASLAYFDSYRRDRLPANLVQAQRDYFGA
              .***;*;;;;**.***.**  .;;.;********;***.***;****.******;***

Maize-PGD3    HTYERIDCPGSFHTEWTKLARRSNGAAI
Maize-PGD1    HTYERVDMPGSFHTEWFKIARNISNN---
Maize-PGD2    HTYERVDMPGSFHTEWFKIARNSKI---
              *****;*  ********  *;**  ;
```

FIG. 19

```
Hordeum-vulgare-plast       QNLALNIAEKGFPISVYNRTaaKVDsTLSRAAAEGALPVLGHRDPPDFVLSLARPRTVVL
Oryza-sativa-PGD2-plast     QNLALNIAEKGFPISVYNPTaaKVDATVSRAEAEGALPVLGHRDPRGFVLSLSPPRTVVL
Maize-PGD3                  QNLALNIAEKGFPISVYNRTaaKVDsTLSRAsDEsSLPVLGHRDPRGFVLSLARPRAVVL
Setaria-italica-PGD2-plast  QNLALNIAEKGFPISVYNRTaaKVDsTLVRAPDEGALPVLGHRDPRGFVLSLARPRTVVL
Spinacia-plast              QNLALNIAEKGFPISVYNPTa       LDRAKSEGDLPLSGHYTPRDFVLSIEPPRSIVI
Solanum-plast               QNLALNIAEKGFPISVYNR         LDRAQNESGQLPLIGQYNPRDFVLSIQRPKSVII
Brassica-plast              QNLALNIAEKGFPISVYNR         LDPAAVEGNLPVSGQYSPRDFVLSLQRPRSLII
Cucumis-plast               QNLALNIAEKGFPISVYNP         DRAHNEGNLPLFGQYNPRDFVLSIQRPPSVII
Triticum-aestivum-cyt       QNLALNIAEKGFPISVYNR         RAKLEGNLPLYGFHDPASFVNSIQKPRVVIM
Oryza-brachyantha-cyt       QNLALNIAEKGFPISVYNR         RAKAEGNLPVYGFHDPASFVNSIQKPRVVIM
Oryza-sativa-Japonica-cyt   QNLALNIAEKGFPISVYNR         RAKVEGNLPVYGFHDPASFVNSIQKPRVVIM
Maize-PGD1                  QNLALNIAEKGFPISVYNR         RAKAEGNLPVYGFHDPASFVKSIQKPRVVIM
Maize-PGD2                  QNLALNIAEKGFPISVYNR         RAKVEGNLPVFGFHDPASFVESIQKPRVVIM
Setaria-italica-cyt         QNLALNIAEKGFPISVYNR         RAKVEGNLPVYGFHDPASFVSSIQKPRVVIM
Spinacia-cyt                QNLALNIAEKGFPISVYNR         ERAKQEGNLPLYGFHDPESFVNSIQKPRVIIM
Brassica-cyt                QNLALNIAEKGFPISVYNR         ERAKKEGNLPVYGFHDPESFVNSIQKPRVIIM
Cucumis-cyt                 QNLALNIAEKGFPISVYNR         EPAKAEGNLPLYGFHDPESFVQSIQKPRVIIM
Solanum-1-cyt               QNLALNIAEKGFPISVYNPS        ERAKKEGNLPLYGFHDPESFVLSIQKPRVIII
                            *******.*********:;;*** *: ** ** **; *   * ,** *; :** :::

Hordeum-vulgare-plast       GALVDKILDKTGMKGTGKWTVQQAAELAVAAPTIAASLDGRyLSGLKDEPVAASSVLAEE
Oryza-sativa-PGD2-plast     GGLVDKILDKTGMKGTGKWTVQQAAELAIAAPTIAASLDGRyLSGLKDERVAAAGVLEAE
Maize-PGD3                  GALVDRILDRTGMKGTGKWTVQQAAELAVAAPTIAASLDGRyLSGLKDERVAAAGVLEEE
Setaria-italica-PGD2-plast  GALVDKILDKTGMKGTGKWTVQQAAELAVAAPTIAASLDGRyLSGLKDERVAAAGVLEEE
Spinacia-plast              SGLVDKILDKTGMKGTGKWTVQQAAELSVAAPTIAASLDCRyLSGLKEERENAAKILEAA
Solanum-plast               GELVDKILDKTGMKGTGKWTVQQAAELSIAAPTIAASLDSRyMSGLRDEREEASEIFRFE
Brassica-plast              GELVDKILDKTGMKGTGKWTVQQAAELSVAAPTIAASLDCRyLSGLKDERENAAKVLREA
Cucumis-plast               GELVDKILDKTGMKGTGKWTVQQAAELSIAAPTIAASLDCRyLSGLKEERESAAEVLKEA
Triticum-aestivum-cyt       GYLVDKVLDKTGMKGTGKWTVQQAAELSVAAPTIEASLDSR         VAASKIFQGD
Oryza-brachyantha-cyt       GYLVDKVLDKTGMKGTGKWTVQQAAELSVAAPTIEASLDSR         VEAAKIFQGD
Oryza-sativa-Japonica-cyt   SHLVDKVLDKTGMKGTGKWTVQQAAELSVAAPTIEASLDSR         VEAAKVFQGD
Maize-PGD1                  GYLVDRVLDKTGMKGTGKWTVQQAAELSVAAPTIEASLDSR         VEASKIFQGD
Maize-PGD2                  GYLVDKVLDKTGMKGTGKWTVQQAAELSVAAPTIEASLDSR         VEASKIFQGD
Setaria-italica-cyt         GYLVDKVLDKTGMKGTGKWTVQQAAELSVAAPTIEASLDSR         VEASKIFQGD
Spinacia-cyt                GYLVDKVLDKTGMKGTGKWTVQQAAELSVAAPTIASSLDSP         VEAAKVFKAG
Brassica-cyt                GELVDKVLDKTGMKGTGKWTVQQAAELSVPSPTIESSLDAR         VQAAFVFKEG
Cucumis-cyt                 GYLVDKVLDKTGMKGTGKWTVQQAADLSVAVPTIASSLDARFLSGLKsSPVEAAKVFG-S
Solanum-1-cyt               GYLVDKVLDKTGMKGTGKWTVQQAAELSVAAPTIAASLDSR         VQAAKVFESS
                            * ***:;************:(*:;    ***  :***  *;;****;;**   *: ::

Hordeum-vulgare-plast       GMPTGLL----EKINVNKKVLVDNVPQALYSSKVCSYAQGMNLLRAKSVEKGWNLNLAELS
Oryza-sativa-PGD2-plast     GMPSGLL----ETINVDKFMLVDRVRQALYASKICSYAQGMNLLRAKSVEKGWNLNLAELA
Maize-PGD3                  GMPAGLL----ETVNVDKKVLVDRVRQALYASKICSYAQGMNLLRAKSVEKGWNLNLAELA
Setaria-italica-PGD2-plast  GMPAGLL----EKINVDKKVLVDRVPQALYASKICSYAQGMNLIRAKSVEKGWNLNLAELA
Spinacia-plast              GMKEEVNAIR--GGVDKRRLIDDVRQALYASKICSYAQGMNLLRAKSAEMGWDLNLGELA
Solanum-plast               GLKEEISSGING  DLDKFRLIDEVRQALYASKICSYAQGMNLLRAKSSEKGWNLNLGEMA
Brassica-plast              GLKEEIGSAS--  GIDKRRLVDDVRQALYASKICSYAQGMNLLRAKSLERSWNLNFGELA
Cucumis-plast               GMTDIVGSVR--  GIDKKKLIEDVPQALYASKICSYAQGMNLLRAKSLEKGWNLNLGELA
Triticum-aestivum-cyt       YS-----S----GETVDKAQLIEDVRKALYASKICSYAQGMNIIKAKSVEKGWGLNLGELA
Oryza-brachyantha-cyt       FS----S-----DLPVDKAQLIEDVRQALYASKICSYAQGMNIIKAKSMEKGWSLNLGELA
Oryza-sativa-Japonica-cyt   FS-----S----NLPVDKAQLIEDVRQALYASKICSYAQGMNIIKAKSMEKGWSLNLGELA
Maize-PGD1                  YY----ST----G PVDKAQLvEDVRQALYASKICSYAQGMNIIKAKSAEKGWGLNLGELA
Maize-PGD2                  Y----ST-----GLPVDKAQLIEDVRQALYASKICSYAQGMNIIKAKSSEKGWGLNLGELA
Setaria-italica-cyt         Y-----ST----GLPVDKAQLIEDVRQALYASKICSYAQGMNIIKAKSEKGWALNLGELA
Spinacia-cyt                GVEDTLS----DQVVDKKKLIDDVRQALYAAKICSYAQGMNLIRAKSVEKEWDLKLGELA
Brassica-cyt                GFGDVLT-----DQTVDKFQLIDEVRKALYASKICSYAQGMNLIRAKSMEKGWGLKLGELA
Cucumis-cyt                 GLNDVLA-----PQEVDRAKLIDDVRQALYASKICSYAQGMNLIPAKSIEKGWDLKLGELA
Solanum-1-cyt               GVSDIFV----EQTVDKNQLIDDVRKALYASKICSYAQGMNLIRAKSVEKGWDLKLGELA
                            ::*  *;: *:;***:*;*;:********;;;**** *  * *::;.*::
```

FIG. 21

FIG. 30
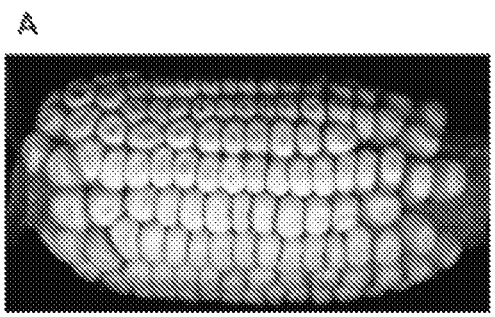
pgd3/pgd3; Wpgd2-F/Wpgd2-F
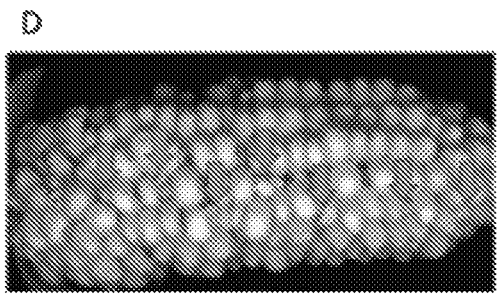
pgd3/pgd3; Wpgd2-F/-

FIG. 32
A  WPgd1-E
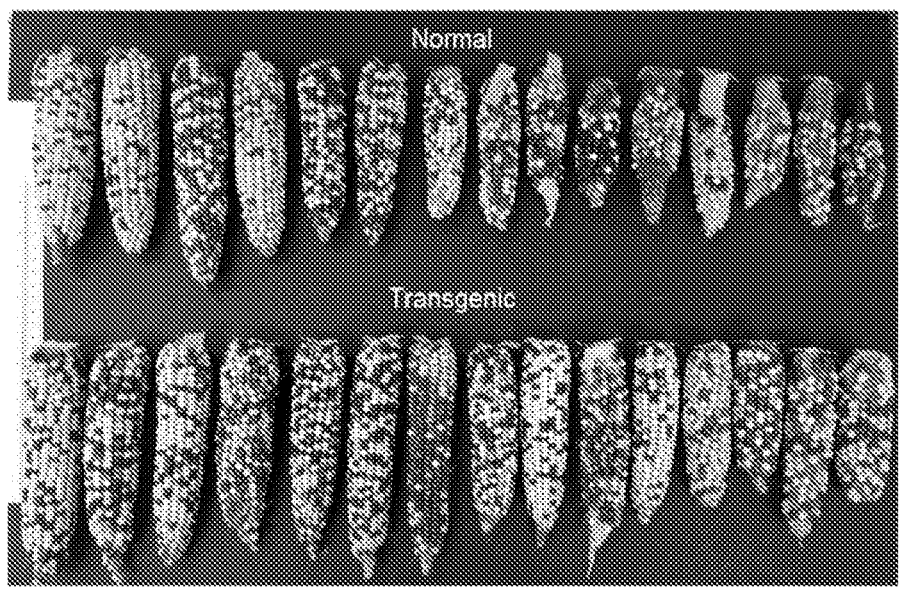
B  WPgd2-C
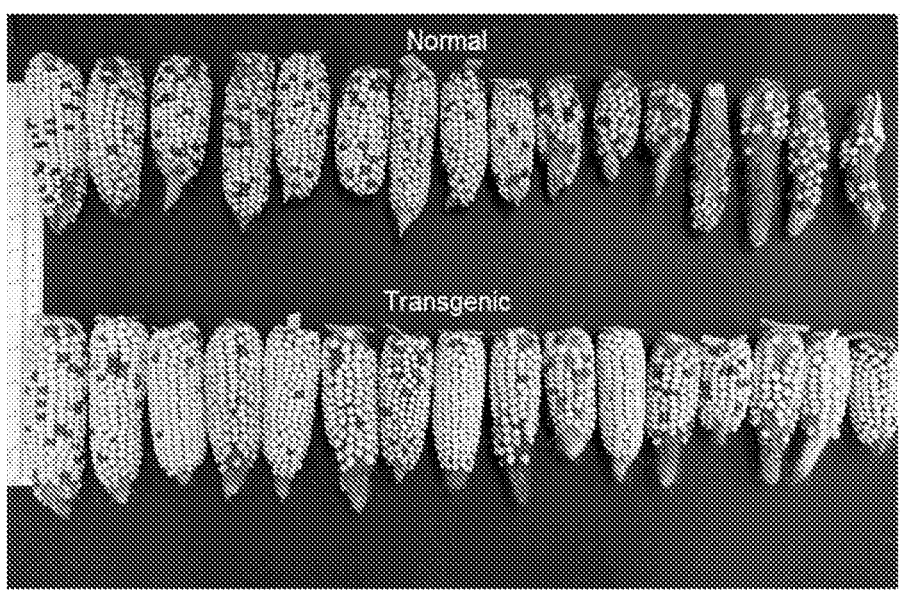

MITIGATION OF MAIZE HEAT STRESS WITH RECOMBINANT 6-PHOSPHOGLUCONATE DEHYDROGENASE

CROSS-REFERENCE TO RELATED APPLICATIONS

This application claims the benefit of U.S. provisional application Ser. No. 62/581,070, filed 3 Nov. 2017. The entire contents of this provisional application is hereby incorporated by reference as if fully set forth herein.

GOVERNMENT FUNDING SUPPORT

This invention was made with government support under grant no. 2011-67003-30215, awarded by the United States Department of Agriculture. The government has certain rights in the invention.

This work was carried out with support from CNPq, Conselho Nacional de Desenvolvimento Cientifico e Tecnológico, Brazil Project no. 209426/20124.

STATEMENT OF JOINT RESEARCH AGREEMENT

In compliance with 37 C.F.R. § 1.71(g)(1), disclosure is herein made that the inventions described and claimed herein were made pursuant to a Joint Research Agreement as defined in 35 U.S.C. 103 (c)(3), that was in effect on or before the date the inventions were made, and as a result of activities undertaken within the scope of the Joint Research Agreement, by or on the behalf of CNPq, Conselho Nacional de Desenvolvimento Cientifico e Tecnológico—Brazil.

BACKGROUND

1. Field of the Invention

The present invention relates to generally plant biology. More particularly, the present invention relates to products and methods for genetically modifying a plant, preferably corn.

2. Background of the Invention

Maize, *Zea mays* L., currently is the second most produced grain crop globally, and is predicted to be the most consumed cereal in the world by 2020. The crop originates from the mountainous regions of Mexico and was likely domesticated in Mexico's Central Balsas River Valley approximately 8,700 years ago. Domestication changed maize dramatically from its teosinte ancestors, with novel traits such as exposed kernels attached to a cob, reproduction by cross-pollination, and more rows of kernels. The resulting high-yielding modern maize is cultivated worldwide. Maize plays a critical role in global grain production due to its high starch yield potential.

Traditional plant breeding programs have greatly enhanced yield and grain quality in most corn producing countries. Technologies such as hybrid seeds and improved management techniques have expanded the corn production range, however there is a pressing need to generate varieties that can tolerate different weather patterns due to climate change. Climate change is increasing abiotic stresses on corn production regions including larger temperature swings at planting, greater heat stress during pollination and grain-fill, and an increased frequency of drought. Therefore, there is a great need in the art for methodologies to allow insertion of nucleic acids into plants, particularly corn. Genetic studies of yield enhancement mechanisms and environmental stress tolerance are critical for the future of maize production. The discovery of genes related to abiotic stress is an important goal to generate new germplasm for breeders and producers.

SUMMARY OF THE INVENTION

Therefore, the invention pertains, in a broad aspect, to recombinant nucleotides comprising a nucleic acid sequence encoding a fusion protein with a plastid targeting sequence, fused in frame with cytosolic 6-phosphogluconate dehydrogenase (6PGDH), wherein this fusion protein is able to import into a plastid of a plant cell.

Specifically, one embodiment of the invention pertains to a recombinant polynucleotide comprising a nucleic acid sequence encoding a fusion protein comprising a plastid targeting sequence fused in frame with cytosolic 6-phosphogluconate dehydrogenase (6PGDH), wherein the fusion protein is able to import into a plastid of a plant cell. A further embodiment of the invention pertains to an expression cassette comprising a regulatory region operably linked to a nucleic acid sequence encoding a fusion protein comprising a plastid targeting sequence fused in frame with cytosolic 6-phosphogluconate dehydrogenase (6PGDH), wherein the regulatory region is a plant promoter. An additional embodiment of the invention related to an expression vector comprising a nucleic acid sequence encoding a fusion protein, wherein the fusion protein comprises a plastid targeting sequence fused in frame with cytosolic 6-phosphogluconate dehydrogenase (6PGDH), wherein the fusion protein is able to import into a plastid of a plant cell. An additional embodiment of the invention pertains to a nucleic acid sequence encoding a fusion protein, wherein the fusion protein comprises a plastid targeting sequence fused in frame with cytosolic 6-phosphogluconate dehydrogenase (6PGDH), wherein the fusion protein is able to import into a plastid of a plant cell. A further embodiment pertains to a transgenic plant comprising a nucleic acid sequence encoding a fusion protein, wherein the fusion protein comprises a plastid targeting sequence fused in frame with cytosolic 6-phosphogluconate dehydrogenase (6PGDH), wherein the fusion protein is able to import into a plastid of a plant cell. Another embodiment of the invention relates to a method for developing a transgenic plant that has increased heat resistance and yield during heat stress, comprising introducing the expression cassette of claim 2 in a plant cell.

BRIEF DESCRIPTION OF THE FIGURES

The accompanying drawings, which are incorporated herein and constitute part of this specification, illustrate exemplary embodiments of the invention, and, together with the general description given above and the detailed description given below, serve to explain the features of the invention. The following figures are illustrative only and are not intended to be limiting.

FIG. 7A, FIG. 7B, FIG. 7C, FIG. 7D, FIG. 7E, FIG. 7F, FIG. 7G, FIG. 7H, and FIG. 7I provide a full vector sequence of pIPK27-MCSBAR according to one embodiment of the present invention. Sense, SEQ ID NO:1; Antisense, SEQ ID NO:2.

FIG. 8 is a protein alignment between *Saccharomyces cerevisae* 6PGDH (Gnd1), PGD1 and PGD1 mutant proteins according to one embodiment of the present invention (GnDI, SEQ ID NO:3; PGD1, SEQ ID NO:4; and PGD1mut, SEQ ID NO:5).

FIG. 10 is a protein alignment between *Saccharomyces cerevisae* 6PGDH (Gnd1), PGD2 and PGD2 mutant proteins according to one embodiment of the present invention (GnDI, SEQ ID NO:6; PGD2, SEQ ID NO:7; and PGD2mut. SEQ ID NO:8).

FIG. 17A is a photograph of a gel showing PGD3 and PGD1/PDG2 in W22 endosperm, 14 DAP. FIG. 17B and FIG. 17C are graphs illustrating the thermostability of 6PGDH isozymes.

FIG. 19 provides a sequence alignment illustrating post-translational regulatory differences of the cytosolic and plastid Zm6PGDH Protein sequences alignment between maize PGD1, PGD2 and PGD3 (Maize-PGD3, SEQ ID NO:8; Maize-PGD1, SEQ ID NO:9; Maize-PGD2, SEQ ID NO:10).

FIG. 21 is a protein sequence alignment between closely related 6PGDH in the indicated plants, showing SEQ ID NO:11-64.

FIG. 34A (ear weight, early); FIG. 34B (ear weight, late); FIG. 34C (grain yield, early); FIG. 34D (grain yield, late); FIG. 34E (100 kernel weight, early); FIG. 34F (100 kernel weight, late); FIG. 34G (ear length, early); FIG. 34H (ear length, late); FIG. 34I (cob weight, early); FIG. 34J (cob weight, late).

DETAILED DESCRIPTION

1. Overview

Figure 1:
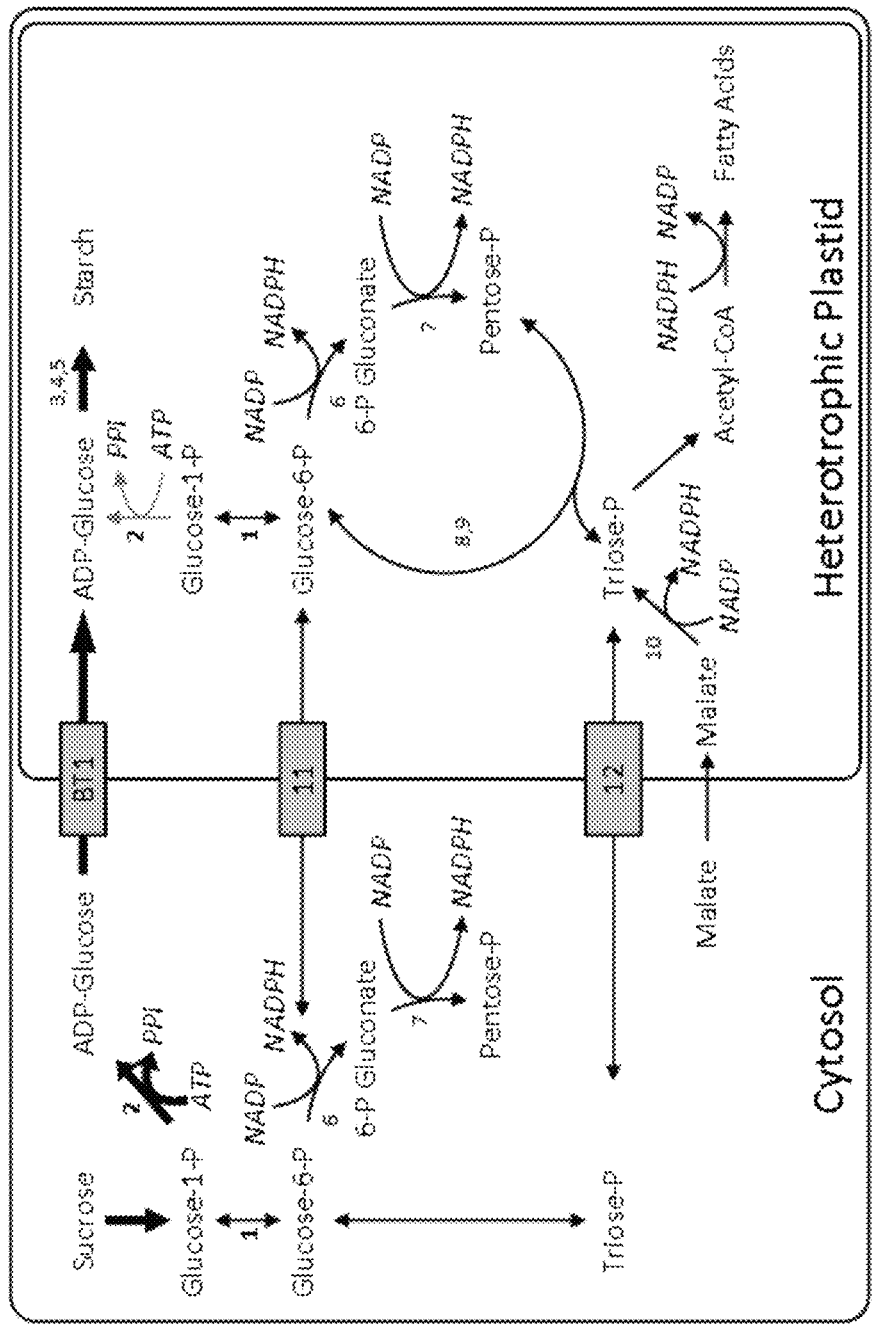
FIG. 1 is a diagram showing starch synthesis and the pentose phosphate pathway (PPP) in the maize endosperm. The invention pertains to enzymatic step 7 in the drawing.

Identifying and understanding the factors contributing to the adaptation of organisms living under extreme conditions has been a long-standing problem. Thermophilic organisms adapted to extreme heat have thermostable proteins that maintain their activities at high temperatures (Reed et al., 2013). Primary protein sequence and secondary structures of thermophilic and mesophilic proteins show many conserved features (Vieille et al., 2001). Studies comparing thermophilic and mesophilic homolog proteins found conserved predicted hydrophobicity, compactness, oligomeric states, polar and non-polar contributions to surface areas as well as main-chain and side-chain hydrogen bonds. However, salt bridges and side chain-side and main-chain hydrogens bonds were shown more abundant in most thermophilic proteins. Those differential structural patterns could cause subtle conformational modifications, and influence on the differential heat stability patterns. Also, some amino acids are more frequently found in thermophilic proteins, such as Arg and Tyr, while Cys and Ser are less frequent. Those sequence differences suggest post-translational regulation may be more common in heat-sensitive enzymes than in heat-stable enzymes.

Eukaryotic cells compartmentalize metabolic functions through membrane-bound organelles. The mitochondria and chloroplast originate from endosymbiosis in which a eukaryotic cell integrated first alpha-proteobacterium and then a photosynthetic cyanobacterium to form the mitochondria and chloroplast, respectively. Some photosynthetic eukaryotes obtained chloroplasts by merging with a plastid-bearing eukaryotic cell, which would be a secondary or higher order endosymbiosis (reviewed in Archibald, 2015).

Many enzyme activities are needed in multiple subcellular compartments. In plants, multiple isozymes for the same catalytic reaction can be found and the number of isozymes roughly reflects the ploidy and number of subcellular compartments in which the reaction is required (Gottlieb, 1982; Soltis et al., 2014). The differences between two isozymes can be due to the need to import one version of the protein into the chloroplast or mitochondria (Silva-Filho, 2003; Li and Teng, 2013). Also, specific isozymes may be more adapted to a unique internal environment, such as high pH (Gottlieb and Weeden, 1981). The evolution of a novel biochemical pathway, for example, a C4 type of photosynthesis, happened by the generation of new genes, or functional shifts in existing genes (review in Sage, 2004). A common mechanism utilized for the creation of new genes is gene duplication. For those reasons, plant genomes possess duplicated genes and gene families that originated from single-gene duplications, tandem duplications, and whole-genome duplications (Bowers et al., 2003; Van de Peer et al., 2017). Most of the PPP enzymes in plants exist as isozymes that are distributed between the cytosol and plastids, except for transaldolase and transketolase which isozymes appear to be exclusive from the plastids. There is also evidence of exchange of OxPPP intermediates by plastid phosphate translocators in *Arabidopsis* (Kruger and von Schaewen, 2003).

The PPP is one of the main sources of reducing molecules and sugar phosphates that can be utilized for several biosynthetic processes (Kruger and von Schaewen, 2003). The PPP is composed of eight enzymes with 27 isozymes in maize with some isozymes encoding proteins with different subcellular localization and other isozymes resulting from gene duplications. Most studies on the biological roles of PPP enzymes are from *Arabidopsis*, and pleiotropic effects on different stages of the plant life cycle have been observed. For example, the plastid-localized PGL isozyme, PGL3, was found to be critical for plant development (Xiong et al., 2009b). PGL3 is also required for nitrate assimilation in roots (Bussell et al., 2013b). Mutations in the peroxisomal 6PGDH (PGD2) cause reproductive defects in both male gametophytes and pollen tube-ovule interaction (Hölscher et al., 2016). A mutation in the cytosolic RPI, rpi2, resulted in chloroplast malfunction, reduced starch on leaves, reproductive defects, and premature cell death (Xiong et al., 2009a). Furthermore, a mutation of the plastidic PGI1 reduced growth, decreased photosynthetic rates, as well as starch content in leaves (Bahaji et al., 2015).

Previous studies showed that PPP enzymes are plastid-localized (Schnarrenberger et al., 1995), and at night chloroplasts have a formal reversal of the Calvin-Benson cycle (Buchanan, 1991; Scheibe, 1991; Kruger and Von Schaewen, 2003). However, there are isozymes from the irreversible reactions that are present in the cytosol and peroxisomes (Corpas et al., 1998; Meyer et al., 2011; Hölscher et al., 2014; Hölscher et al., 2016). Beyond the metabolic role of each isozyme, the subcellular localization role between cytosol, plastids and peroxisomes has been explored. All of the oxPPP enzymes have at least one example of a dual-targeted protein going to the cytosol or plastid as well as to peroxisomes including G6PDH (Meyer et al., 2011), 6PGL (Hölscher et al., 2014) and 6PGDH (Hölscher et al., 2016; Marie-Christin Lutterbey and To, 2017). For example, the *Arabidopsis* 6PGDH isozymes AtPGD1, AtPGD2, and AtPGD3 have distinct subcellular localization. Using reporter-fusion assays, AtPGD1 and AtPGD3 were shown to accumulate in the cytosol and chloroplasts respectively (Hölscher et al., 2016) AtPGD2 remains in the cytosol but can also be present in the peroxisomes with a C-terminal targeting signal. Importantly, AtPGD2 peroxisomal activity was found to be critical for gametophyte function in *Arabidopsis*.

In maize, the best-characterized PPP isozyme is 6PGDH. Double homozygous mutants of the cytosolic proteins PGD1 and PGD2 (pgd1-null; pgd2-125 null) were isolated (Bailey-Serres et al., 1992). 6PGDH cytosolic mutations do not show any plant or seed phenotype but are unresponsive to nitrite due to a decreased NADPH generation (Averill et al., 1998). Two null alleles of the plastidic 6PGDH locus, Pgd3, showed that plastid-localized 6PGDH is critical to endosperm starch accumulation and embryo development (Settles et al., 2007; Spielbauer et al., 2013).

High temperatures can alter starch accumulation and sucrose synthesis by decreasing gene expression in carbohydrate metabolic enzymes (Ruan et al., 2010; Bita and Gerats, 2013). However, the effects of heat stress on PPP enzymes have not been characterized in detail. Heat and other abiotic stresses have some effects on G6PDH gene expression and enzyme activity. A study of 40° C. heat treatments on calli from *Przewalskia tangutia* and *Nicotiana benthamiana* found total G6PDH enzyme activity increased (Gong et al., 2012). In sugarcane, a cytosolic G6PDH gene is up-regulated under several abiotic stresses including as salt, drought, heavy metal, and low temperatures (Yang et al., 2014). In tomato, short and long-term drought suggest an important role for G6PDH, as total activity increased after drought stress and the gene expression of the cytosolic isozyme is up-regulated (Landi et al., 2016). Combined, these data suggest that oxPPP function is responsive to abiotic stresses. A proteomic analysis of wheat leaves exposed to drought-induced treatments indeed showed that 6PGDH was significantly upregulated (Cheng et al., 2015).

Based on PPP mutant studies, there is significant evidence for distinct physiological and metabolic roles of the PPP in the cytosol and the plastid. Moreover, the plant enzymes in the cytosol and plastid evolved from different ancestral genomes according to endosymbiotic theory (for a review, see Archibald, 2015). Ancestral differences or selection for compartment-specific functions may have resulted in differing biochemical characteristics of cytosol versus plastidic isozymes. The objective of this example was to determine whether the maize 6PGDH isozymes show differences in responses to heat stress or heat stability.

The disclosure here relates to modification of a heat resistant cytoplasmic heat stable 6-phosphogluconate dehydrogenase (6PGDH) enzyme by fusing the cytoplasmic 6PGDH enzyme in frame to a plastid-targeting sequence. This modification allows the import of the cytoplasmic 6PGDH enzyme into plastids of a plant cell. Polynucleotides encoding and expressing the modified cytoplasmic 6PGDH enzymes are provided. The disclosure further provides transgenic plants and seeds containing the disclosed polynucleotides and expressing the modified cytoplasmic 6PGDH enzymes during development. The invention further relates to methods for developing a transgenic plant that has increased heat resistance and yield during heat stress.

While the invention is susceptible to various modifications and alternative forms, specific embodiment thereof has been shown by way of example in the drawings and will be described in detail below. It should be understood, however that it is not intended to limit the invention to the particular forms disclosed, but on the contrary, the invention is to cover all modifications, equivalents, and alternatives falling within the spirit and the scope of the invention.

2. Definitions

Unless defined otherwise, all technical and scientific terms used herein are intended to have the same meaning as commonly understood by one of ordinary skill in the art. Although various methods and materials similar or equivalent to those described herein can be used in the practice or testing of the present invention, suitable methods and materials are described below. However, the skilled artisan understands that the methods and materials used and described are examples and may not be the only ones suitable for use in the invention. Moreover, as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary.

The practice of the disclosed invention will employ, unless otherwise indicated, conventional techniques of botany, microbiology, tissue culture, molecular biology, chemistry, biochemistry and recombinant DNA technology, which are within the skill of the art. Such techniques are explained fully in the literature. See, e.g., Langenheim and Thimann, (1982) *Botany: Plant Biology and Its Relation to Human Affairs*, John Wiley; *Cell Culture and Somatic Cell Genetics of Plants*, vol. 1, Vasil, ed. (1984); Stanier, et al., (1986) *The Microbial World*, 5$^h$ed., Prentice-Hall; Dhringra and Sinclair, (1985) *Basic Plant Pathology Methods*, CRC Press; Maniatis, et al., (1982) *Molecular Cloning: A Laboratory Manual; DNA Cloning*, vols. I and II, Glover, ed. (1985); *Oligonucleotide Synthesis*, Gait, ed. (1984); *Nucleic Acid Hybridization*, Hames and Higgins, eds. (1984); and the series *Methods in Enzymology*, Colowick and Kaplan, eds, Academic Press, Inc., San Diego, Calif.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

The foregoing general description and the following detailed description are exemplary and explanatory only and are not restrictive of any subject matter claimed. In this application, the use of the singular includes the plural unless specifically stated otherwise. As used in the specification and the appended claims, the singular forms "a," "an" and "the" include plural referents unless the context clearly dictates otherwise. In this application, the use of "or" means "and/or" unless stated otherwise. Furthermore, for purposes of the present invention use of the term "including" as well as other forms, such as "include", "includes," and "included," and the terms "comprising" and "having," and variations of these words, are intended to be open-ended and mean that there may be additional elements other than the listed elements.

For purposes of the present invention, directional terms such as "top," "bottom," "upper," "lower," "above," "below," "left," "right," "horizontal," "vertical," "up," "down," etc., are used merely for convenience in describing the various embodiments of the present invention.

The embodiments of the present invention may be oriented in various ways. For example, the diagrams, apparatuses, etc., shown in the drawing figures may be flipped over, rotated by 90 in any direction, reversed, etc. In addition, for purposes of the present invention, a value or property is "based" on a particular value, property, the satisfaction of a condition, or other factor, if that value is derived by performing a mathematical calculation or logical decision using that value, property or other factor.

The term "about," as used herein, means plus or minus 20 percent of the recited value, so that, for example, "about 0.125" means 0.125±0.025, and "about 1.0" means 1.0±0.2.

The term "adjacent," as used herein, refers to "next to" or "adjoining something else."

The term "amino acid," as used herein, refers to the molecules composed of terminal amine and carboxylic acid functional groups with a carbon atom between the terminal amine and carboxylic acid functional groups, sometimes containing a side chain functional group attached to the carbon atom (e.g. a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3,4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification, the amino acids include the L-optical isomer, the D-optical isomer, or a racemate.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80% or 90%, preferably 60-90% of the native protein for its native substrate. Conservative substitution tables providing functionally similar amino acids are well known in the art. The following six groups each contain amino acids that are conservative substitutions for one another. See also, Creighton, Proteins, W.H. Freeman and Co. (1984).

(1) Alanine (A), Serine (S), Threonine (T);
(2) Aspartic acid (D), Glutamic acid (E);
(3) Asparagine (N), Glutamine (Q);
(4) Arginine (R), Lysine (K);
(5) Isoleucine (I), Leucine (L), Methionine (M), Valine (V); and
(6) Phenylalanine (F), Tyrosine (Y), Tryptophan (W).

The term "analyte," as used herein, refers to the conventional meaning of the term "analyte," i.e., a substance or chemical constituent of a sample that is being detected or measured in a sample. In one embodiment of the present invention, a sample to be analyzed may be an aqueous sample, but other types of samples may also be analyzed using a device of the present invention.

The term "biomolecule," as used herein, refers to the conventional meaning of the term biomolecule, i.e., a molecule produced by or found in living cells, e.g., a protein, a carbohydrate, a lipid, a phospholipid, a nucleic acid, etc.

The term "corresponding," as used herein, refers to that on comparison of a number of articles, the articles in question which are being compared with one another were kept under identical conditions. In connection with the present invention, the term "corresponding," in connection with a wild-type plant cell or wild-type plant, means that the plant cells or plants which are being compared with one another were grown under identical culture conditions and that they have an identical (cultivation) age.

The term "cisgenesis," as used herein, refers to organisms that have been engineered using a process in which genes are artificially transferred between organisms that could otherwise be conventionally bred. Unlike in transgenesis, genes are only transferred between closely related organisms. The term "cisgenic" refers to a genetic modification in which genes from other species are not involved.

The term "conservatively modified variants," as used herein, applies to both amino acid and nucleic acid sequences. With respect to particular nucleic acid sequences, conservatively modified variants refer to those nucleic acids that encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill will recognize that each codon in a nucleic acid (except AUG, which is ordinarily the only codon for methionine; one exception is *Micrococcus rubens*, for which GTG is the methionine codon can be modified to yield a functionally identical molecule. Accordingly, each silent variation of a nucleic acid, which encodes a polypeptide of the disclosed invention, is implicit in each described polypeptide sequence and incorporated herein by reference.

The phrase "consisting essentially of" when used in relation to a specified nucleic acid, includes reference to the inclusion of additional sequences to an object polynucleotide where the additional sequences do not selectively hybridize, under stringent hybridization conditions, to the same cDNA as the polynucleotide and where the hybridization conditions include a wash step in 0.1×SSC and 0.1% sodium dodecyl sulfate at 65° C.

The terms "correspond" and "corresponding," as used herein with respect to polyamino acids and polynucleotides, relate to interchangeable amino acid position(s) of a protein or nucleotide position(s) of a polynucleotide. For example, an amino acid at a position of a protein may be found to be equivalent or corresponding to an amino acid at a position of one or more other protein(s) based on any relevant evidence, such as the primary sequence context of the each amino acid, its position in relation to the N-terminal or C-terminal ends of its respective protein, the structural and functional roles of each amino acid in its respective protein, etc.

The term "crop plants" and the term "agricultural plants," as used herein, refer to plants that have economic importance for human or animal food production, or for animal fodder production. "Crop plants" or "agricultural plants" can include grains, fruits and vegetables as well as grasses. Horticultural plants include those for turfgrass, windbreaks and landscaping and include ornamental plants such as flowers, shrubs, vines and the like.

The term "cross," as used herein in relation to plant breeding, refers to deliberate interbreeding of closely or distantly related individuals to produce new plant varieties or lines with desirable properties. Plants are crossbred to introduce traits/genes from one variety or line into a new genetic background. Progeny from a cross may be crossed with a parent having a particular trait to ensure that the progeny are most like the parent having the particular trait (backcrossing). Plants may also be crossed with themselves to produce inbred varieties for breeding.

The term "diagnose," as used herein, refers to identify the nature of a disease, condition, or other problem by examination of the symptoms in a plant.

The terms "encoding" and "encoded," as used herein in relation to a specified nucleic acid, include reference to comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum*, or the ciliate *Macronucleus*, may be used when the nucleic acid is expressed using these organisms. When the nucleic acid is prepared or altered synthetically, advantage can be taken of known codon preferences of the intended host where the nucleic acid is to be expressed. For example, although nucleic acid sequences of the disclosed invention may be expressed in both monocotyledonous and dicotyledonous plant species, sequences can be modified to account for the specific codon preferences and GC content preferences of monocotyledonous plants or dicotyledonous plants as these preferences have been shown to differ. Thus, the rice preferred codon for a particular amino acid might be derived from known gene sequences from rice.

The term "expression cassette," as used herein, refers to a part of a vector DNA used for cloning and transformation. In each successful transformation, the expression cassette directs the cell's machinery to make RNA and protein. Some expression cassettes are designed for modular cloning of protein-encoding sequences so that the same cassette can easily be altered to make different proteins. Expression cassettes also can refer to a recombinantly-produced nucleic acid molecule that is capable of expressing a genetic sequence in a cell. An expression cassette typically includes a regulatory region such as a promoter, (allowing transcription initiation), and a sequence encoding one or more proteins or RNAs. Optionally, the expression cassette may include transcriptional enhancers, non-coding sequences, splicing signals, transcription termination signals, and polyadenylation signals. The sequences controlling the expression of the gene, i.e. its transcription and the translation of the transcription product, are commonly referred to as regulatory unit. Most parts of the regulatory unit are located upstream of coding sequence of the heterologous gene and are operably linked thereto. The expression cassette may also contain a downstream 3' untranslated region comprising a polyadenylation site. The regulatory unit of the invention is either directly linked to the gene to be expressed, i.e. transcription unit, or is separated therefrom by intervening DNA such as for example by the 5'-untranslated region of the heterologous gene. Preferably the expression cassette is flanked by one or more suitable restriction sites in order to enable the insertion of the expression cassette into a vector and/or its excision from a vector. Thus, the expression cassette according to the disclosed invention can be used for the construction of an expression vector, in particular a mammalian expression vector.

The term "expression vector," otherwise known as "expression construct," as used herein, refers to a plasmid or virus designed for protein expression in cells. The vector is used to introduce a specific gene into a target cell, and can commandeer the cell's mechanism for protein synthesis to produce the protein encoded by the gene. The plasmid is engineered to contain regulatory sequences that act as enhancer and promoter regions and lead to efficient transcription of the gene carried on the expression vector. The goal of a well-designed expression vector is the production of significant amount of stable messenger RNA, and therefore proteins.

The term "fragment," as used herein in relation to a molecule such as a protein or nucleic acid refers to a portion of the amino acid or nucleotide sequence. For example, a fragment can include portions containing about 5-20 amino acids or nucleotides, or up to about 99% of the complete sequence, including 21-50 amino acids or nucleotides, 51-70 amino acids or nucleotides, 71-90 amino acids or nucleotides, 91-100 amino acids or nucleotides, or more.

The term "fuse," as used herein, refers to join together physically, or to make things join together and become a single thing.

The term "fusion protein," as used herein, refers to a polypeptide or a protein created through the joining of two or more genes that originally coded for separate proteins.

The term "heat liable," as used herein, refers to easily changed or destroyed by heat. For example, an enzyme or protein that is heat liable may mean that the enzyme or protein is not capable of maintaining its form, structure, or function at high temperatures, and as a result, the enzyme or protein becomes inactivated at high temperatures. The term "heat stable," as used herein in relation to a protein or enzyme, refers to be capable of maintaining its form, structure, and/or function even at high temperatures. As a result, an enzyme or protein that is heat stable will maintain activated even at high temperatures. The term "high temperature," as used herein refers to a temperature that affects the growth of plants or above the tolerance limit of a plant. For example, with respect to maize, the high temperature may be cumulative time above about 85° F. or 29.4° C. Alternatively, high temperature for maize may be average night temperatures above 68° F. or 20° C.

The terms "identical" and "identity," as used herein, refer to two or more polypeptide or nucleotide sequences having the same amino acid or nucleotide at corresponding positions.

The phrases "in-frame fusion" and "fusion in frame," as used herein in relation to polypeptides or proteins, refers to when generating a recombinant fusion protein through genetic engineering, the stop codon from a cDNA sequence coding for the first protein is removed and the cDNA sequence of the second protein is connected to the cDNA sequence coding for the first protein through ligation or overlap extension (PCR), thus generating an open reading frame in the mRNA so that a fusion protein will be produced. That DNA sequence will then be expressed by a cell as a single protein.

The term "introduce," as used herein in relation to a nucleic acid, refers to inserting a nucleic acid into a cell, which is can be accomplished by "transfection," "transformation," or "transduction." In some situations, introducing a nucleic acid into a cell can include the incorporation of a nucleic acid into a eukaryotic or prokaryotic cell, where the nucleic acid can be incorporated into the genome of the cell (e.g., chromosome, plasmid, plastid or mitochondrial DNA), converted into an autonomous replicon, or transiently expressed (e.g., transfected mRNA).

The terms "isolated," "isolated nucleic acid," "isolated protein," and "isolated organelle of a plant cell," as used herein, refers to a material, such as a nucleic acid, a protein, or organelle, which is substantially or essentially free from components which normally accompany or interact with it as found in its naturally occurring environment, and included purified and partially purified material. The isolated material optionally comprises material not found with the material in its natural environment.

The term "mutant protein," as used herein, refers to a protein product encoded by a gene with mutation.

The terms "nucleic acid" and "polynucleotide," as used herein, are interchangeable and refer to a deoxyribonucleotide or ribonucleotide polymer in either single- or double-stranded form, and unless otherwise limited, encompasses known analogs having the essential nature of natural nucleotides in that they hybridize to single-stranded nucleic acids in a manner similar to naturally occurring nucleotides (e.g., peptide nucleic acids).

The term "open reading frame" or "ORF," refers to a part of a reading frame that has the potential to be translated. An ORF is a continuous stretch of codons that contain a start codon (usually AUG) and a stop codon (usually UAA, UAG or UGA). An ATG codon within the ORF (not necessarily the first) may indicate where translation starts. The transcription termination site is located after the ORF, beyond the translation stop.

The terms "operably linked," "operably associated," and "functionally linked," as used herein, are interchangeable and refer to a functional relationship between two or more DNA segments. In particular, "operably linked" refers to a functional linkage between a first nucleic acid sequence, such as a promoter, in a functional relationship with a second nucleic acid sequence, wherein the promoter sequence initiates and mediates transcription of the DNA corresponding to the second sequence. A promoter/enhancer sequence, including any combination of cis-acting transcriptional control elements is operably associated to a coding sequence if the promoter/enhancer sequence affects the transcription or expression of the coding sequence in an appropriate host cell or other expression system. Promoter regulatory sequences that are operably linked to the transcribed gene sequence are physically contiguous to the transcribed sequence. Generally, operably linked means that the nucleic acid sequences being linked are contiguous and, where necessary to join two protein coding regions, contiguous and in the same reading frame.

The terms "peptide linker" and "linker" are interchangeable and refer to short peptide sequences that occur between functional protein domains and link the functional domains together. Linkers designed by researchers are generally classified into three categories according to their structures: flexible linkers, rigid linkers, and in vivo cleavable linkers. A flexible linker is often composed of flexible amino acid residues like glycine and serine so that the adjacent protein domains are free to move relative to one another. A linker also may play a role in releasing the free functional domain in vivo (as in in vivo cleavable linkers). Linkers may offer many other advantages for the production of fusion proteins, such as improving biological activity, increasing expression yield, and achieving desirable pharmacokinetic profiles. The composition and length of a linker may be determined in accordance with methods well known in the art and may be tested for efficacy. A linker may have about 3 to about 15 amino acids. In some embodiments of the disclosed invention, a linker may have about 5 to about 10 amino acids, however, longer linker may be used in embodiments of the disclosed invention.

The term "plant" includes reference to whole plants, plant organs (e.g., leaves, stems, roots, etc.), seeds and plant cells and progeny of same. "Plant cell," as used herein, includes, without limitation, cells in or from seeds, suspension cultures, embryos, meristematic regions, callus tissue, leaves, roots, shoots, gametophytes, sporophytes, pollen, and microspores. The class of plants which can be used in the methods of the invention is generally as broad as the class of higher plants amenable to transformation techniques, including both monocotyledonous and dicotyledonous plants including species from the genera: *Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium*, and *Triticum*. A particularly preferred plant is *Zea mays*.

The term "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). "Substantially the same," as used herein with reference to polynucleotides, refers to a polynucleotide with a sequence that is at least about 80% identical to another sequence, preferably at least 85% or 90% identical, and more preferably at least 95% or 97% identical and most preferably at least 98%, 99%, or 99.5% identical. A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including inter alia, simple and complex cells.

The term "polypeptide," the term "peptide," and the term "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria which comprise genes expressed in plant cells such *Agrobacterium* or *Rhizobium*. Examples are promoters that preferentially initiate transcription in certain tissues, such as leaves, roots, seeds, fibers, xylem vessels, tracheids, or sclerenchyma. Such promoters are referred to as "tissue-preferred." A "cell type" specific promoter primarily drives expression in certain cell types in one or more organs, for example, vascular cells in roots or leaves. An "inducible" or "regulatable" promoter is a promoter which is under environmental control. Examples of environmental conditions that may affect transcription by inducible promoters include anaerobic conditions or the presence of light. Another type of promoter is a developmentally regulated promoter, for example, a promoter that drives expression during pollen development. Tissue preferred, cell type specific, developmentally regulated, and inducible promoters constitute the class of "non-constitutive" promoters. A "constitutive" promoter is a promoter, which is active under most environmental conditions.

The term "protein domain" refers to a distinct functional or structural unit in a protein. Usually, a protein domain is responsible for a particular function or interaction, contributing to the overall role of a protein. Domains may exist in a variety of biological contexts, where similar domains can be found in proteins with different functions.

The term "purified" refers to the component in a relatively pure state, for example at least about 80%, 85% or 90% pure, preferably 95%, 97%, 98%, or 99% pure, including 99.5% pure and 99.9% pure.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "recombinant" refers to a genetic material formed by a genetic recombination process. A "recombinant protein" is made through genetic engineering. A recombinant protein is coded by a DNA sequence created artificially. A recombinant protein is a protein that is coded by a recombinant nucleic acid sequence. A recombinant nucleic acid sequence has a sequence from two or more sources incorporated into a single molecule.

The term "recombinant protein" refers to a protein derived from a recombinant DNA, that is, its code was carried by a "recombinant DNA" molecule. Recombinant DNA molecules are DNA molecules formed by laboratory methods of genetic recombination (such as molecular cloning) to bring together genetic material from multiple sources, creating sequences that would not otherwise be found in biological organisms.

The term "reference allele," "reference genome" or "reference background" refers to a defined allele, genome, or background used as a basis for comparison.

The term "residue," the term "amino acid residue," or the term "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "room temperature" refers to a temperature of from about 20° C. to about 25° C.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The term "subunit" refers to a separate polypeptide chain that makes a certain protein which is made up of two or more polypeptide chains joined together. In a protein molecule composed of more than one subunit, each subunit can form a stable folded structure by itself. The amino acid sequences of subunits of a protein can be identical, similar, or completely different.

The term "synergistic effect" refers to a combined effect when two or more substances or biological structures interact resulting in an overall effect that is greater than the sum of individual effects of any of the two or more substances or biological structures. For example, a synergistic effect of two therapeutic compounds means that an effect of administering two therapeutic compounds in combination is greater than the sum of each effect when each of the two therapeutic compounds is administered alone.

The term "target" refers to a living organism or a biological molecule to which some other entity, like a ligand or a drug, is directed and/or binds. For example, "target protein" may a biological molecule, such as a protein or protein complex, a receptor, or a portion of a biological molecule, etc., capable of being bound and regulated by a biologically active composition such as a pharmacologically active drug compound.

The term "transfection" refers to a variety of art-recognized techniques for introducing foreign nucleic acid (e.g., DNA) into a host cell by calcium phosphate or calcium chloride co-precipitation, DEAE-dextran-mediated transfection, lipofection (e.g., using commercially available reagents such as, for example, LIPOFECTIN® (Invitrogen™), LIPOFECTAMINE® (Invitrogen™), FUGENE® (Roche™ Applied Science), JETPEI™ (Polyplus-transfection™ Inc.), EFFECTENE® (Qiagen™), DREAMFECT™ (OZ Biosciences) and the like), electroporation (e.g., in vivo electroporation), etc. Suitable methods for transfecting host cells can be found in Sambrook, et al., ("Molecular Cloning: A Laboratory Manual." 2nd, ed., Cold Spring harbor Laboratory, Cold Spring Harbor Laboratory Press, Cold Spring Harbor, NY, 1989), and other laboratory manuals known in the art.

The term "transgenic" refers to an organism whose genome has been genetically modified, i.e., changed by the addition of a gene from another species or a genetically engineered recombinant gene, and as a result, the organism's genome has been changed by such addition. The term "transgenic plant" includes reference to a plant, which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

The term "vector" includes reference to a nucleic acid used in transfection of a host cell and into which can be inserted a polynucleotide. Vectors are often replicons. Expression vectors permit transcription of a nucleic acid inserted therein. A "suitable vector" refers to any vector (for example, a plasmid or virus) which may incorporate a nucleic acid sequence encoding an antigenic polypeptide and any desired control sequences. It may bring about the expression of the nucleic acid sequence. The choice of the vector will typically depend on the compatibility of the vector with a host cell into which the vector is to be introduced.

The term "wild-type plant cell" refers to a plant cell of which genetic information is not modified or changed. A wild-type plant cell may be served as a starting material for the production of an engineered plant cell that is introduced modified genetic information according to the present invention.

3. Summary of Results

The present disclosure provides an approach to genetically modify a plant so that a heat stable 6-phosphogluconate dehydrogenase can be localized to plastids of the plant. Genetic modification of maize expressing recombinant 6-phosphogluconate dehydrogenase (6PGDH) enzymes during seed development allows for greater yield under heat stress environments. The modification is based on the knowledge that cytoplasmic isoforms of maize 6PGDH are more heat stable than the plastid-localized enzyme. The generated plastid-targeted versions of the cytoplasmic isoforms are capable of increasing total and heat-resistant enzyme activity during seed development. Transgenic plants containing these heat-resistant gene variants are able to increase yield by about 10-30% under heat stress conditions. There is no negative effect of expressing this transgene under more optimal growth conditions. This present disclosure provides a new method of ensuring greater yield under environmental stress conditions without causing a yield drag in optimal conditions. Our recombinant gene design utilizes a maize promoter, a maize plastid-targeting sequence, and maize 6PGDH enzymes. This allows a cisgenic design to reduce regulatory burdens for implementing the invention.

4. Embodiments of the Invention

A. Carbon Metabolism

Starch is the primary storage molecule in the maize kernel, and increased starch content is directly related to higher yield in hybrids. FIG. 1 is a schematic showing starch synthesis and the Pentose Phosphate Pathway (PPP) in the maize endosperm. Thick arrows present the conventional biosynthesis of starch: glucose-1-P is converted to ADP-glucose, which is transported into the plastid and polymerized into starch. In this figure, 1 represents Phosphoglucomutase; 2 represents ADP Glucose Pyrophosphorylase (AGPase); 3 represents Starch Synthase; 4 represents Starch Branching Enzyme; 5 represents Starch Debranching Enzyme. In the Pentose Phosphate Pathway shown in FIG. 1: 6 represents Glucose 6-Phosphate Dehydrogenase (G6PDH); 7 represents 6-Phosphogluconate Dehydrogenase (6PGDH); 8 represents Transaldolase; 9 represents Transketolase; 10 represents Malic enzyme; 11 represents Glucose-6-P/P translocator; 12 represents Triose-P/P translocator and P/phosphoenolpyruvate translocator (Adapted from Spielbauer et al., 2013). The invention pertains in general to the enzymatic step 7 in the drawing.

Maize grain-fill relies on the sucrose transported from the maternal phloem into the pedicel. The basal endosperm cells transfer these nutrients to the endosperm and embryo. The passive efflux of sucrose from the maize pedicel symplast occurs after the extracellular hydrolysis to glucose and fructose hexose sugars. The hexoses are phosphorylated and imported to the endosperm and embryo cytosol to supply cellular energy and precursors of storage compounds. The importance of sucrose cleavage is illustrated by the maize miniature1 (mn1) seed mutation. Mutant mn1 kernels lack invertase activity to cleave sucrose into hexoses. This results in reduced grain-fill and aberrant pedicel and basal endosperm development. Thus, sugar up-take and carbon metabolism are essential for accumulation of the primary endosperm storage molecule, starch.

The first committed step of maize endosperm starch synthesis is the conversion of glucose 1-phosphate (glucose 1-P) into ADP-glucose by a cytoplasmic ADP-glucose pyrophosphorylase, AGPase. Maize endosperm AGPase is a multisubunit enzyme encoded by the brittle2 (bt2) and shrunken2 (sh2) loci. Mutants in bt2 and sh2 are used for commercial sweet corn production in the United States. Heat stable variants of these proteins have been engineered and shown to improve yield in maize, rice, and wheat. ADP-glucose is then directed into the amyloplast through the BRITTLE1 (BT1) transporter protein. The ADP-glucose then is polymerized into starch with a series of starch synthases and debranching enzymes.

Starch can be polymerized directly from intact hexoses derived from cleaved sucrose. However, metabolic studies have shown that central carbon metabolism is involved in endosperm starch accumulation. Labelling studies have shown rearrangements between the C-1 and C-6 positions of glucose elements in endosperm starch, which indicates metabolic cycling between trioses and hexoses in the cytosol.

In potato, complex engineering of sugar transporters and carbon metabolic enzymes resulted in increased rate of export of sucrose from source leaves with enhancement of starch storage. By contrast, the metabolic pathways by which trioses are incorporated into maize endosperm starch are not fully understood. Carbon flux experiments using fully labelled $^{13}$C-glucose, $^{13}$C-sucrose, or $^{13}$C-acetate quantified intermediary metabolism of carbon flow into maize endosperm starch. Based on glucose isotopologue abundances, the relative contributions of the Central Carbon Metabolism pathways can be estimated. Glycolysis, gluconeogenesis and the pentose phosphate pathway (PPP) are the predominant metabolic processes for hexose recycling and flux into endosperm starch.

Alonso et al., (2010) developed a metabolite flux model for primary metabolism in developing endosperm during seed filling. There is an excess production of NADPH that is well above demand for known endosperm metabolic processes. This flux model suggests NADPH has additional roles that are currently unknown. NADPH is produced by the first and third enzymes of the PPP, glucose-6-phosphate dehydrogenase (G6PDH, step 6 in FIG. 1) and 6-phosphogluconate dehydrogenase (6PGDH, step 7 in FIG. 1). One of these PPP enzymes, chloroplast-localized 6PGDH, has been shown to be required for normal grain-fill and endosperm starch accumulation.

The pentose phosphate pathway (PPP) is composed of two distinct parts or metabolic stages. The non-reversible, oxidative section of the pathway (oxPPP) is an important source of NADPH that is utilized for synthesis of fatty acids and glutamine. NADPH also provides reducing equivalents for nitrate assimilation by nitrite reduction as well as protecting the plant against oxidative stress. The reversible non-oxidative section of the pathway (noxPPP) generates 3-carbon to 7-carbon phosphate sugars that are used as substrates for the synthesis of nucleotides, aromatic amino acids, and other secondary metabolites such as phenylpropanoids.

The PPP has seven enzymatic activities. The oxidative phase includes glucose-6-phosphate 1-dehydrogenase (G6PDH), 6-phosphogluconolactonase (6PGL), 6-phosphogluconate dehydrogenase (6PGDH). The non-oxidative phase is composed of ribose-5-phophate isomerase (RPI), ribulose-5-phosphate 3-epimerase (RPE), transketolase (TK) and transaldolase (TA). The oxPPP enzymes are found in both the cytosol and plastids, while noxPPP enzymes are primarily found in plastids. Activity of both G6PDH and 6PGDH were found in purified peroxisomes from pea leaves, indicating that the oxPPP can also be present in peroxisomes. Products of the non-oxidative section were identified in the cytosol of castor bean endosperm, soybean root nodules and cauliflower buds. There is a phosphate-translocator family among plastid inner-envelope membrane proteins that has the capacity to transport pentose phosphates between plastids and the cytosol. These translocators provide a mechanism for noxPPP products to accumulate in the cytosol.

Although studies have established the subcellular localization of many PPP enzymes in plant cells, the biological roles of the pathway in plants are still being unraveled. For example, the *Arabidopsis* plastid-localized 6PGL isozyme (PGL3) is required for plant development, and the subcellular localization of this activity is essential for complementing the phenotype. PGL3 has also been linked to nitrate assimilation in roots. The knockout of a cytosolic noxPPP enzyme, RPI2, affects chloroplast structure, diminishes plant photosynthetic capacity, and mutants were found to accumulate less starch in the leaves. The rpi2 mutant phenotype could indicate a co-dependence between plastids and cytosol metabolic intermediates.

In maize, the cytosolic loci of 6PGDH, Pgd1 and Pgd2 were first identified by isozyme activity assays. Null alleles from these loci were identified activity assay screens and a double mutant was generated with the pgd1-null and pgd2-125 null alleles. This double mutant did not show any seed or plant phenotype. By contrast, null alleles of plastid-localized PGD3 (pgd3-umu1, pgd3-umu2) show severe defective kernel phenotypes. Starch levels decreased in the pgd3 mutant on a dry weight basis coupled with increased levels of reducing sugars. Labelling of endosperm starch with $^{13}$C-glucose showed altered carbon flux into starch. These data indicate a critical role for PGD3 in endosperm starch accumulation. The contrast in phenotypes between loss for cytosolic and plastidic isoforms of oxPPP enzymes suggests distinct metabolic functions.

B. The Effect of Heat Stress on Grain Development

Heat stress reduces grain weight and quality in maize. The early stage of the grain filling stage, 10 to 12 days after pollination (DAP), is critical to kernel development in maize. The ability to accumulate dry matter, otherwise known as kernel sink capacity, is determined around 10 to 12 DAP by the number of endosperm cells formed and starch granules initiated. Environmental changes may affect kernel sink capacity, subsequent kernel development and grain yield in maize. For example, temperatures above the optimum 25° C. during reproductive development decrease grain yield. It was proposed that for each 10° C. increase in temperature above the optimum 25° C. results in a decrease of 3% to 4% in grain yield. A more recent models proposes that corn has a nonlinear response to high temperatures with yield showing exponentially increasing losses with exposure above 29° C. Heat stress yield losses in corn are also correlated with night time temperatures that average above 20° C.

Sugar and starch metabolism are likely to be directly affected by heat stress during endosperm development with enzymes from these pathways showing sensitivity to high temperatures. In a survey of eleven enzyme activities, GPase, glucokinase, sucrose synthase and soluble starch synthase were the enzymes with the greatest sensitivity to high temperatures. The peptide sequence basis for AGPase thermosensitivity kinetics has been intensely studied. Heat stable variants of AGPase have been introduced in transgenic plants and shown positive effects on yield under elevated temperatures in potato tubers, wheat grain, rice grain, and maize.

Characterizing and understanding the mechanisms by which high temperature stress disrupts and limits maize kernel development is essential to enhance plant thermotolerance and provide improved yield stability now and in a future, warmer world impacted by climate change.

Heat stress reduces maize grain weight and quality. Starch synthesis in the endosperm is sensitive to high temperature stress and has the potential to be a limiting pathway for grain yield under heat stress. In addition to enzymes directly involved in starch biosynthesis, chloroplast-localized 6-phosphogluconate dehydrogenase (PGD3) is critical for starch accumulation. PGD3 is one of three enzymes in the oxidative section of the Pentose Phosphate Pathway (PPP). Maize encodes two cytosolic isozymes, PGD1 and PGD2. Double mutants of pgd1; pgd2 have a nearly complete loss of cytosolic activity and develop normal kernels.

C. Distinct Functional Roles for the Pentose Phosphate Pathway Isozymes

The PPP is one of the main sources of reducing molecules and sugar phosphates that can be utilized for several biosynthetic processes. As discussed above, the PPP is composed of eight enzymes with 27 isozymes in maize with some isozymes encoding proteins with different subcellular localization and other isozymes resulting from gene duplications. Most of the PPP enzymes in plants exist as isozymes that are distributed between the cytosol and plastids, except for transaldolase and transketolase which isozymes appear to be exclusive to plastids. There is also evidence of exchange of OxPPP intermediates by plastid phosphate translocators in *Arabidopsis*. The plastid-localized 6-phosphogluconate dehydrogenase (6PGDH) is a critical enzyme for grain-fill in maize. In maize, the eight PPP enzymes are encoded by 27 genes with isozymes of the same enzyme having different subcellular localization. For 6PGDH, maize has three genes: Pgd1, Pgd2, and Pgd3.

Figure 2:
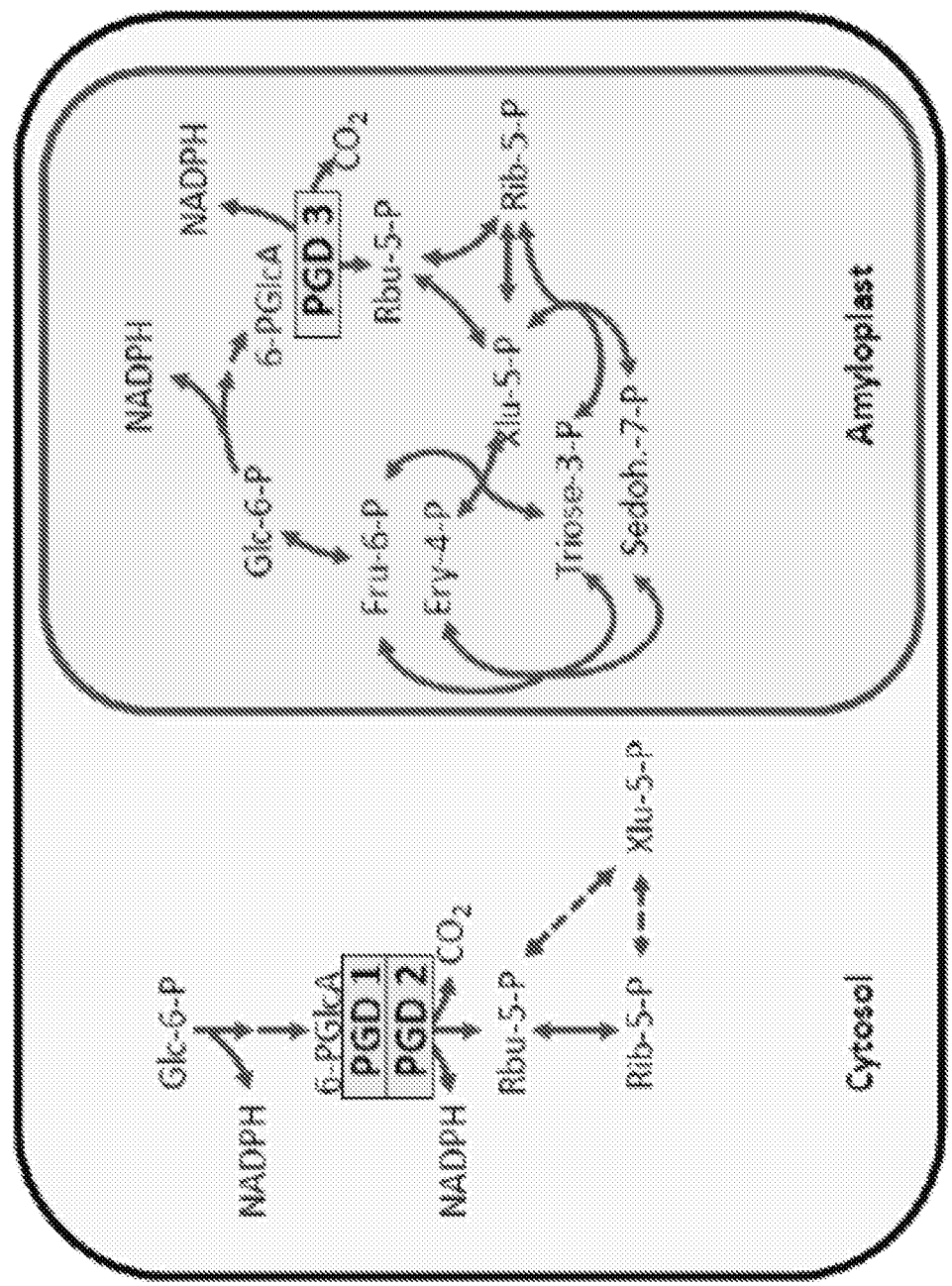
FIG. 2 is a diagram showing 6PGDH compartment localization critical for the seed phenotype.

Plastid-localized 6PGDH appears to be the sole isozyme required for normal maize kernel development. FIG. 2 is a diagram showing 6PGDH compartment localization that is critical for the seed phenotype. As shown in FIG. 2, the PGD1 and PGD2 proteins are cytosolic, while PGD3 is the plastid-localized enzyme required for grain-fill. PGD3 is critical for starch accumulation. Starch levels go down in the pgd3 mutant on a dry weight basis. Endosperm metabolite profiling experiments indicated that pgd3 has increased reducing sugars similar to starch-biosynthesis mutants. Heavy isotope-labelling experiments indicate that carbon flux into starch is altered in pgd3/pgd3. Labelling experiments with pgd1/pgd2 did not affect flux into starch.

Endosperm enzyme activities from the pgd3 mutant and pgd1; pgd2 double mutants were compared. The comparison confirms that PGD1 and PGD2 are localized to the cytosol and that double mutants of these cytoplasmic isozymes do not affect kernel phenotypes (FIG. 14). Double mutants of pgd1; pgd2 have a nearly complete loss of cytosolic activity but develop normal kernels.

The thermostability of 6PGDH isoenzymes is affected by in vitro heat treatments, as shown in FIG. 17. Cytosolic PGD1 and PGD2 isozymes are heat stable, while the amyloplast-localized PGD3 is heat labile under in vitro and in vivo heat stress conditions. See FIG. 17. Isozyme sensitivity to in vitro heat treatments was compared qualitatively with native PAGE in-gel assays. These experiments show that the PGD3 isozyme is much more sensitive to heat treatments. To quantify the sensitivity, spectrophotometric assays were used with mutants lacking either plastid-localized or cytoplasmic isozymes (see FIG. 17B and FIG. 17C). The combined results suggest that PGD3 loses 40-80% of activity after only 20 minutes of heat treatment, while the PGD1 and PGD2 enzymes are very stable in these treatments. The discovery suggests that PGD3 enzyme activity is limiting during grain-fill in heat stress conditions. PGD1 and PGD2 isozymes could provide heat-resistant 6PGDH activity, but these enzymes are localized to the cytosol and cannot substitute for the plastid-localized PGD3 isozyme.

D. Transgene Design

Embodiments of the disclosure provide genetically modified heat stable 6-phosphogluconate dehydrogenases by fusing PGD1 or PGD2 to a targeting sequence that is able to lead PGD1 and PGD2 import into plastids in plant cells. The genetically modified PGD1 and PGD2 are able to substitute plastid-localized heat labile 6-phosphogluconate dehydrogenases, e.g., PGD3 isozyme, thereby providing heat-resistant 6PGDH activity in the plastids during heat stress.

In one embodiment, constructs were developed to fuse the Waxy1 N-terminal chloroplast targeting sequence to the Pgd1 and Pgd2 open reading frames, thereby producing WX1::PGD1 and WX1::PGD2 fusion proteins (i.e., WPGD1 and WPGD2) in order to develop a heat stable 6-phosphogluconate dehydrogenase localized to amyloplasts. The WPGD1 and WPGD2 fusion proteins are capable of importing into isolated pea chloroplasts. WPGD1 comprises an N-terminal chloroplast targeting sequence of starch synthase Waxy1, WX1 transit peptide, fused to PGD1. WPGD2 comprises an N-terminal chloroplast targeting sequence of starch synthase Waxy1, WX1 transit peptide, fused to PGD2. Thus, embodiments provide recombinant proteins, WPGD1 and WPGD2, each having a WAXY1 chloroplast targeting sequence fused at the N-termini of PGD1 and PGD2 isozymes.

Table 1, below shows a targeting sequence that is a WX1 N-terminal transit peptide according to one embodiment of the present invention. This is the WPGD1 and WPGD2 predicted N-terminal protein sequence. The WX1 N-terminal transit peptide is shown with the red highlighted amino acids (VVC) indicating the required processing site for cleavage after import into plastids. In one embodiment, the N-terminal M for both PGD1 and PGD2 is directly fused to the C-terminal WX1 processing site. WPGD1 and WPGD2 may be produced by translationally fusing the N-terminal WX1 transit peptide to both Pgd1 and Pgd2 by gene synthesis. Protein sequencing of the mature WX1 protein identified the transit peptide processing site as VVC, which is used as C-terminal end of the recombinant transit peptide for PGD1 and PGD2. The rationale is to produce native PGD1 and PGD2 protein and enzymatic activity after targeting to the amyloplast with the goal of allowing native folding in the new compartment. See Table 1, which shows WX1 N-terminal transit peptide translationally fused to the N-terminal protein sequence of cytosolic 6PDGH, i.e., WPGD1 and WPGD2, according to one embodiment of the present invention. The processing site is shown in bold and underline.

TABLE 1

WX1 Transit Peptide; PGD1 and PGD2 Mature Protein (SEQ ID NO: 65).

MAALATSQLVATRAGLGVPDASTFRRGAAQGLRGARASAADTLSMRT
SARAAPRHQHQQARRGARFPSL<u>VVC</u>MAALATSQLVATRAGLGVPDAS...

Figure 3:
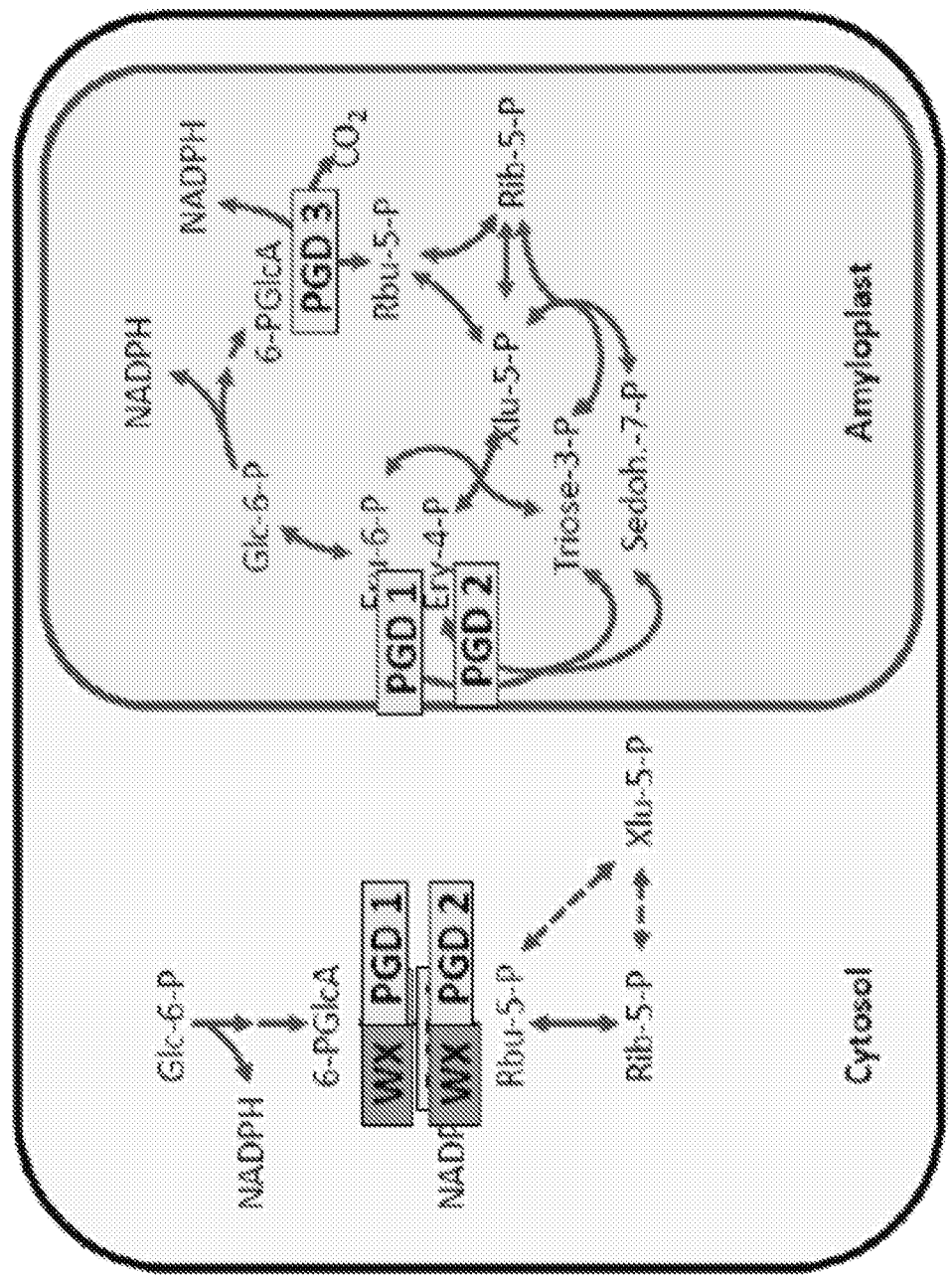
FIG. 3 is a schematic diagram showing plastid import of PGD1 and PGD2 according to one embodiment of the present invention.

FIG. 3 is a diagram showing plastid import of PGD1 and PGD2 according to one embodiment of the present invention. As shown in FIG. 3, modification of the PGD1 and PGD2 proteins can be done with a use of a chloroplast targeting sequence, which directs the PGD1 and PGD2 proteins to plastids, such as an amyloplast. The WX1::PGD1 and WX1::PGD2 fusion proteins (i.e., WPGD1 and WPGD2) can be developed from constructs engineered by fusing the Waxy1 N-terminal chloroplast targeting sequence to the Pgd1 and Pgd2 open reading frames. WPGD1 and WPGD2 are able to import into plastids such as isolated pea chloroplasts and maize endosperm amyloplast, in vitro or in vivo.

Embodiments further provide recombinant polynucleotides that encode the fusion proteins WPGD1 and WPGD2, i.e., Wpgd1 gene and Wpgd2 gene, respectively. In one embodiment, a recombinant polynucleotide comprises the nucleic acid sequence for Waxy1 transit peptide fused in-frame to Pgd1 start codons. Alternatively, a recombinant polynucleotide may also comprise the nucleic acid sequence for Waxy1 transit peptide fused in-frame to Pgd2 start codons. Table 2 and Table 3 provide the recombinant sequences of the Wpgd1 gene and the Wpgd2 gene, respectively, according to one embodiment of the present invention. Underlining shows the HindIII and BamHI cleavage sites for cloning; orange lettering shows the Kozak consensus sequence to improve eukaryotic translation, italics is the chosen N-transit peptide. Bold letters are the 3' codons for the Waxy1 transit peptide cleavage site sequence, which is fused in-frame to the Pgd1 and Pgd2 start codons. The 3' codons for the Waxy1 transit peptide cleavage site sequence before the Pgd1 start codon are highlighted in yellow, which is fused in-frame to the Pgd2 start codon.

Table 2 illustrates the recombinant sequence of the Wpgd1 gene comprising fused sequences of the N-terminal transit peptide from the Waxy gene with Pgd1 according to one embodiment of the present invention. The 3' codons for the Waxy1 transit peptide cleavage site sequence are bolded, which is fused in-frame to the Pgd2 start codon. Table 3 illustrates recombinant sequence of the Wpgd2 gene comprising fused sequences of the N-terminal transit peptide from the Waxy1 gene with Pgd2 according to one embodiment of the present invention. The 3' codons for the Waxy1 transit peptide cleavage site sequence are bolded, which is fused in-frame to the Pgd2 start codons.

TABLE 2

Wpdq1 DNA Sequence (SEQ ID NO: 66).

Wpgd1

<u>AAGCTT</u>gccgccacc*ATGGCGGCTCTGGCCACGTCGCAGCTCGTCGCAAC
GCGCGCCGGCCTGGGCGTCCCGGACGCGTCCACGTTCCGCCGCGGCGCCG
CGCAGGGCCTGAGGGGGGCCCGGGCGTCGGCGGCGGCGGACACGCTCAGC
ATGCGGACCAGCGCGCGCGCGGCGCCCAGGCACCAGCACCAGCAGGCGCG
CCGCGGGGCCAGGTTCCCGTCGCTGTCGTGTGCATGGCGCTCACAAGA*
ATCGGTCTTGCTGGCCTTGCGGTCATGGGGCAGAACCTTGCCCTCAACAT
TGCAGAGAAAGGGTTCCCCATCTCTGTGTACAACAGGACAACCTCCAAGG
TGGACGAGACCGTGCAGCGTGCCAAGGCAGAAGGAAACCTTCCCGTCTAC
GGCTTCCATGACCCCGCGTCCTTTGTGAAGTCCATTCAGAAGCCACGGGT

TABLE 2-continued

Wpdg1 DNA Sequence (SEQ ID NO: 66).

Wpgd1

GGTGATCATGCTCGTCAAGGCCGGCGCGCCAGTTGACCAGACCATCGCGA
CGCTCGCAGCTCACTTGGAGCAGGGCGACTGCATCATCGATGGGGGGAAC
GAGTGGTACGAGAACACGGAGAGGAGGGAGAAGGCCATGGAGGAGCGCGG
CCTCCTGTATCTTGGCATGGGTGTCTCTGGAGGAGAGGAGGGTGCCCGCA
ACGGCCCGTCCTTGATGCCCGGAGGCTCGTTCGAGGCTTACAAGTACGTC
GAAGACATTGTCCTCAAGGTGGCTGCTCAGGTCCCTGACAGTGGCCCGTG
TGTCACGTACATTGGCAAAGGTGGATCGGGCAACTTTGTCAAGATGGTTC
ACAACGGAATCGAGTATGGCGATATGCAGCTGATTTCCGAGGCATACGAC
GTTCTCAAGTCGGTCGGTAAGCTCACCAACAGTGAGCTGCACCAGGTGTT
CTCCGAGTGGAACAAGGGCGAGCTCCTGAGCTTCTTGATCGAGATCACGG
CCGACATCTTTGGCATCAAGGACGAGCATGGCGATGGCTACCTGGTGGAC
AAGGTCCTTGACAAGACCGGGATGAAAGGGACAGGGAAGTGGACGGTGCA
GCAGGCCGCCGAGCTGTCGGTGGCCGCTCCTACGATCGAGGCGTCCTTGG
ACTCGAGGTTCCTGAGCGGGCTGAAGGACGAGCGGGTGGAGGCCTCCAAG
ATCTTCCAGGGTGACTACTACTCCACCGGCTCGCCGGTGGACAAGGCGCA
GCTGGTGGAGGACGTGAGGCAGGCCCTGTACGCGTCCAAGATCTGCAGCT
ACGCGCAGGGCATGAACATCATCAAGGCCAAGAGCGCGAGAAAGGCTGG
GGGCTCAACCTCGGCGAGCTGGCCAGGATCTGGAAGGGCGGGTGCATCAT
CCGCGCCATCTTCCTGGACCGCATCAAGAAGGCCTACGACAGGAACCCGG
GCCTCGCCAGCCTGCTCGTAGACCCCGAGTTCGCGCAGGAGATCATGGAC
AGGCAGGCGCGTGGCGCAGGGTGGTGTGCCTCGCCATCAACAACGGCGT
CAGCACCCCGGGAATGTCCGCTAGCCTGGCCTACTTCGACTCCTACCGCA
GGGACAGGCTGCCTGCCAACCTGGTGCAGGCCCAGAGGGACTACTTCGGG
GCTCACACCTACGAGAGGGTCGACATGCCTGGCTCTTTCCACACCGAGTG
GTTCAAGATTGCGCGCAACATCTCCAACAACTG<u>AGGATCC</u>

TABLE 3

Wpdg2 DNA Sequence (SEQ ID NO: 67)

AAGCTTgccgccaccATGGCGGCTCTGGCCACGTCGCAGCTCGTCGCAAC
GCGCGCCGGCCTGGGCGTCCCGGACGCGTCCACGTTCCGCCGCGGCCCG
CGCAGGGCCTGAGGGGGGCCCGGCGTCGGCGGCGGCGGACACGCTCAGC
ATGCGGACCAGCGCGCGCGCGGCGCCCAGGCACCAGCACCAGCAGGCGCG
CCGCGGGGCCAGGTTCCCGTCGCTCGTCGTGTGCATGGCTCTCACGAGA
ATTGGCCTTGCGGGCCTCGCGGTCATGGGACAGAACCTTGCCCTCAACAT
CGCGGAGAAAGGGTTCCCTATCTCGGTCTACAACAGGACGACCTCCAAGG
TTGATGAGACCGTGCAGCGTGCCAAGGTCGAAGGAAACCTCCCCGTGTTT
GGTTTCCACGACCCCGCGTCCTTCGTGAGCTCCATCCAGAAGCCCCGTGT
CGTCATCATGCTCGTCAAGGCTGGGGCGCCGGTGGACCAGACCATTGCCA
CGCTCGCGGCGCACCTTGATCAGGGGACTGTATCGTCGATGGTGGCAAC
GAGTGGTATGAGAACACGGAGAGGAGGGAGAAGGCGATGGAGGAGCGCGG
GCTCCTTTATCTTGGCATGGGCGTCTCCGGAGGAGAGGAGGGTGCCCGCA
ATGGCCCGTCCTTGATGCCCGGGGGCTCCTTCGAGGCATACAAGTACATT
GAAGATATTCTTCTCAAGGTGGCTGCTCAGGTACCTGACAGCGGCCCGTG
CGTCACATATATTGGCAAAGGTGGATCAGGCAACTTTGTCAAGATGGTTC
ACAATGGAATTGAATATGGTGACATGCAACTTATCGCCGAGGCTTATGAT
GTTCTCAAGTCGGTCGGTAAGCTCACAAACAGCGAGCTGCATCAGGTGTT
CTCTGAGTGGAACAAGGGTGAGCTCCTCAGTTTCTTGATTGAGATCACGG
CCGACATCTTTGGTATCAAGGATGACAAGGGTGAAGGCTACCTGGTCGAC
AAGGTCCTGGACAAGACCGGGATGAAGGGAACCGGGAAATGGACAGTCCA
GCAGGCTGCTGAGCTTTCTGTAGCTGCTCCTACAATCGAGGCGTCCTTGG
ACTCCAGGTTCCTCAGCGGTCTGAAGGACGAGCGCGTTGAGGCTTCCAAA
ATCTTCCAAGGTGACTACTCCACTGGCCTACCGGTGGACAAGGCACAGCT
GATCGAGGACGTGAGGCAAGCTCTATATGCCTCCAAGATCTGCAGTTACG
CGCAGGGCATGAACATCATCAAGGCCAAGAGCTCAGAGAAAGGATGGGGC
CTCAACCTTGGTGAGCTAGCGAGGATCTGGAAGGGAGGGTGCATCATCCG
TGCCATCTTCCTCGACCGCATCAAGAAGGCGTACGATAGGAACCCTAACC
TTGCCAACCTCCTCGTTGACCCCGAGTTCGCCCAGGAGATCATAGACAGG
CAAGCTGCCTGGCGCAGGGTTGTCTGCCTTGCCATCAACAATGGCGTTAG
CACCCCAGGCATGTCTGCAAGTCTGGCCTACTTCGACTCGTACCGCAGGG
ATAGGCTTCCCGCCAACCTGGTGCAGGCTCAGAGAGACTACTTCGGCGCT
CACACGTACGAGAGGGTTGACATGCCTGGTTCTTTCCACACCGAGTGGTT
CAAGATTGCGCGCAACTCCAAGATCTGAGGATCC In some embodiments, expression cassettes or transgenes to express above described Wpgd1 and/or Wpgd2 are provided as embodiments of the invention. Expression cassettes can comprise a first nucleic acid sequence encoding WPGD1 and a second nucleic acid sequence capable of enabling the expression of WPGD1 in plant cells. The second nucleic acid sequence can be a promoter that is suitable for expression in a plant cell. In one embodiment, the second nucleic acid sequence in a disclosed expression cassette is an endosperm specific promoter. In an alternative embodiment, the second nucleic acid in a disclosed expression cassette is an endosperm zein promoter sequence ("27 kDa promoter sequence," or "27 kDa Promoter"). Thus, embodiments of the invention provide recombinant gene design utilizing a maize promoter, a maize plastid-targeting sequence, and maize 6PGDH enzymes. This allows a cisgenic design to reduce regulatory burdens for implementing the embodiment disclosed herein.

An expression cassette according to the invention also can comprise a first nucleic acid sequence encoding WPGD2 and a second nucleic acid sequence capable of enabling the expression of WPGD2 in plant cells. The second nucleic acid sequence can be a promoter that is suitable for expression in a plant cell. In one embodiment of the invention, the second nucleic acid sequence in an expression cassette is an endosperm specific promoter. In an alternative embodiment, the second nucleic acid in a disclosed expression cassette is an endosperm zein promoter sequence (i.e., "27 kDa promoter sequence," or "27 kDA Promoter").

Figure 4:
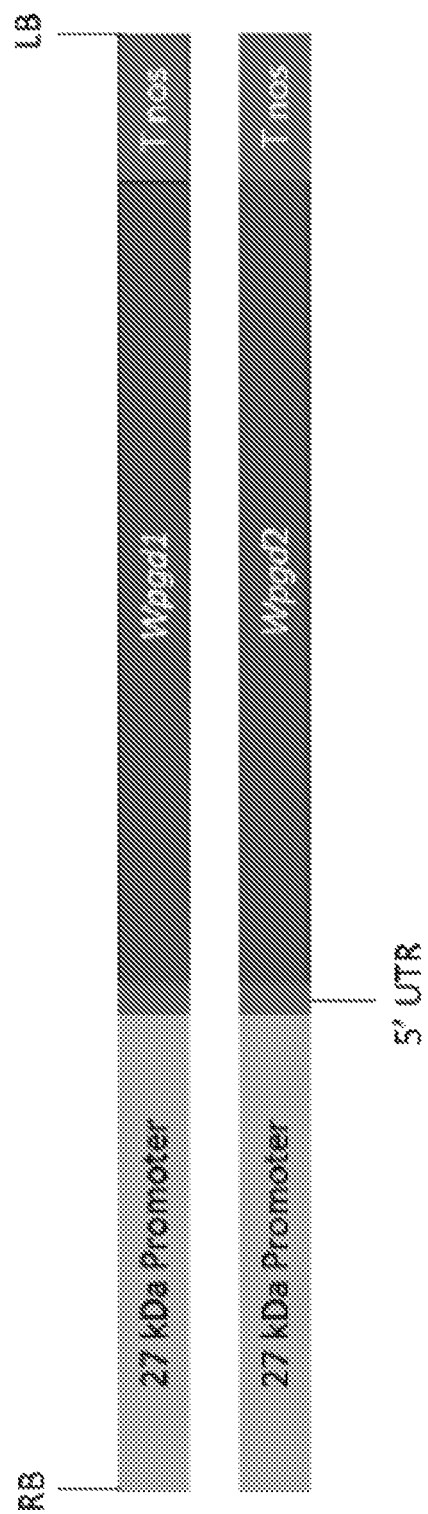
FIG. 4 is a schematic of the constructs of Wpgd1 and Wpgd2 transgenes used for plant transformation according to one embodiment of the present invention.

FIG. 3 and FIG. 4 are the schematic of Wpgd1 and Wpgd2 transgenes according to one embodiment of the present invention, and shows the expression constructs in which the maize endosperm-specific promoter drives expression and the nopaline synthase terminator (nosT) from *Agrobacterium tumefaciens* is used to terminate transcription. Structural analysis of 6PGDH enzymes in other organisms suggest that the WAXY1 transit peptide has been characterized in detail with a precise stromal cleavage site identified. This knowledge allows engineering of fusion proteins with a known, mature N-terminal sequence after import into plastids. The Wpgd1 and Wpgd2 transgenes can be transformed into the inbred line Hill. $T_0$ plants can be self-pollinated and $T_1$ plants can be crossed into the B73 and W22 inbred lines. The Wpgd1 and Wpgd2 transgenes therefore can be expressed specifically in the endosperm during grain-fill to test whether additional, heat-resistant 6PGDH activity in the amyloplast could mitigate heat stress yield losses.

As a non-limiting example, the Wpgd1 and Wpgd2 genes can be synthesized by GenScript™. A Kozak consensus sequence 5' of the Waxy1 start codon can be included to aid in eukaryotic translation. Restriction enzymes such as HindIII and BamHI cleavage sites can be designed at the 5' and 3' end of the Wpgd1 and Wpgd2 fusions to facilitate cloning into diverse vectors (see Table 2 and Table 3). These genes may be then cloned into a T-DNA binary vector containing the 27 kDa 7-zein promoter and a NOS terminator to drive endosperm specific expression of the Wpgd1 and Wpgd2 genes. The T-DNA may also contain a Bar resistance gene against the herbicide glufosinate-ammonium. The Wpgd1 and Wpgd2 constructs can be transformed by *Agrobacterium tumefaciens* into the Hill genotype. $T_0$ transformants can be grown in a greenhouse and be self-pollinated. In one embodiment, there are six independent events of Wpgd1 named Wpgd1-A to Wpgd1-F and seven independent Wpgd2 events named Wpgd2-A to Wpgd2-G.

Figure 5:
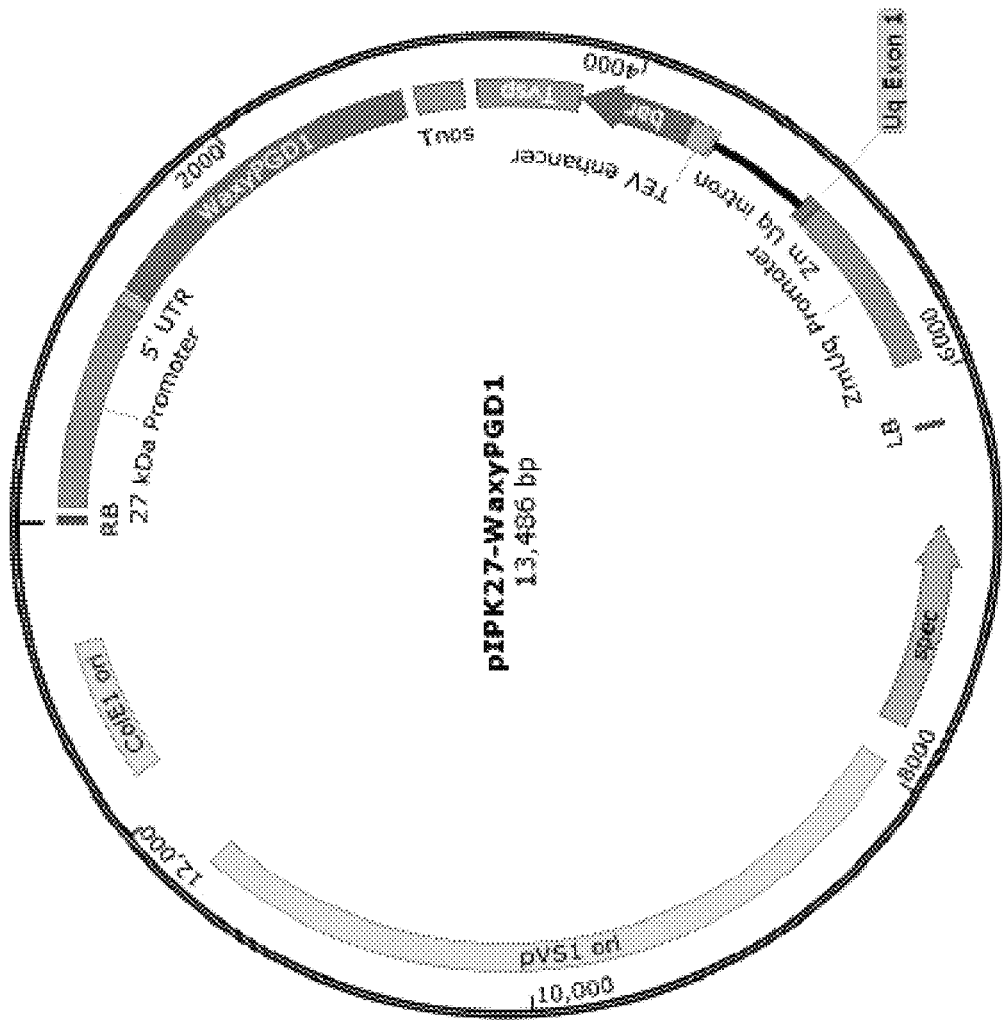
FIG. 5 is a schematic showing a vector structure and an insert of recombinant nucleic acid Wpgd1 according to one embodiment of the present invention.
Figure 6:
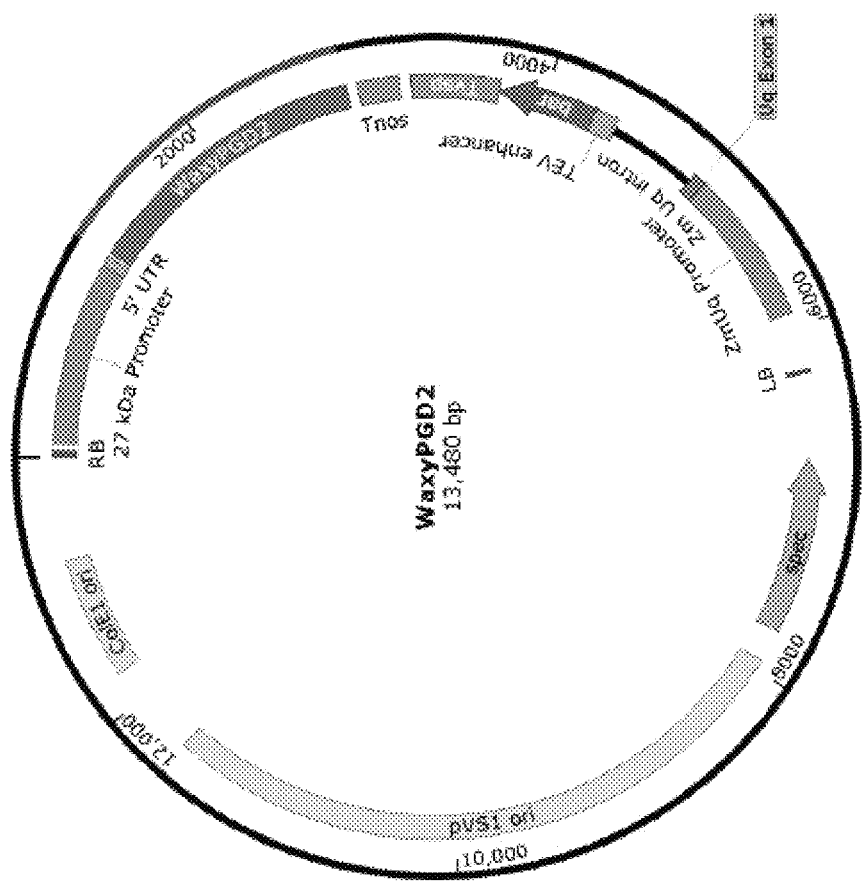
FIG. 6 is a schematic showing a vector structure and an insert of recombinant nucleic acid Wpgd2 according to one embodiment of the present invention.

Embodiments of the invention further include vectors comprising Wpgd1 and Wpgd2 transgenes. FIG. 5 and FIG. 6 are schematic drawings showing a vector structure and an insert of recombinant nucleic acid Wpdg1 and Wpdg2 according to embodiments of the present invention.

FIGS. 7A-7I provide a full vector sequence of pIPK27-MCSBAR according to one embodiment of the present invention. The full vector sequence of pIPK27-MCSBAR includes Endosperm zein promoter sequences (27 kDa promoter sequence (s)) and an NOS terminator sequence. These vectors can be introduced into a plant cell to express WPGD1 and WPGD2 in the cell. As shown in FIG. 7, the Wpgd1 and Wpgd2 genes can be cloned into the pIPK27-MCSBAR binary transformation vector with a 7-zein 27 kDa endosperm-specific promoter. Embodiments further provide host cells containing or carrying the above described Wpgd1 and Wpgd2 transgenes.

E. Genetically Modified Plants

Embodiments of the invention provide genetically modified plants, or transgenic plants, that contain the above described transgenes wpgd1 and/or wpgd2 and are able to express fusion protein WPGD1 and/or WPGD2, respectively. In one embodiment, the transgenic maize plants contain a disclosed expression cassette for expressing WPGD1 and/or WPGD2. In one embodiment, the expression of WPGD1 and/or WPGD2 is driven by the 27 kDa 7-zein promoter to confer endosperm specific expression. The transgenic WPGD1 and WPGD2 are able to target to plastids, such as the amyloplast, and may mitigate grain yield losses in heat stressed conditions. Consequently, the engineered fusion proteins are expected to rescue the defective endosperm phenotype of pgd3 mutants. Transformants may have increased 6-phosphogluconate dehydrogenase enzyme activity and isozyme activity assays suggest the increase is due to higher levels of PGD1 and PGD2. Transgenic endosperm may have enhanced heat stability in vitro. The Wpgd1 or Wpgd2 transgenes complement the pgd3 defective kernel phenotype suggesting the fusion proteins are targeted to the amyloplast. These data disclosed herein support a model in which the amyloplast PPP contributes to maize yield loss during heat stress.

Embodiments of the invention also provide methods to develop transgenic plants that have increased heat resistance and yield during heat stress. In one embodiment, transgenic plants, such as transgenic maize, contain transgenes wpgd1 and/or wpgd2 and can express fusion protein WPGD1 and/or WPGD2, respectively. The method comprises transforming a vector containing an expressing cassette for expressing genetically modified heat-resistant 6PGDH that can be imported into plastids in plant cells. In one embodiment, the method comprises transforming a vector containing an expressing cassette for expressing fusion protein(s) as discussed herein, in maize cells. In one embodiment, the method comprises transforming a vector containing an expressing cassette for expressing Wpgd1 and Wpgd2 transgenes in maize cells. In one embodiment, the vector transformed in a maize cell is a disclosed pIPK27-MCSBAR vector containing γ-zein 27 kDa endosperm-specific promoter and a recombinant polynucleotide encoding the fusion protein of WPGD1 or WPGD2.

In one embodiment, single hemizygous transgenics, Wpgd1/– and Wpgd2/–, as well as the double transgenic, Wpgd1/–; Wpgd2/–, may be crossed with pgd3/+ plants. The F$_1$ progeny then may be self-pollinated and F2 kernels are expected to be 25% pgd3 mutant. See FIG. 25. Among the ¼ pgd3/pgd3 mutants, a single transgene locus is expected to segregate with ¼ being homozygous, ½ being hemizygous, and ¼ being non-transgenic. Thus, the transgene can be expected to rescue 3/16 kernels from the total population, and pgd3 mutant kernels should be reduced to 1/16 of the total kernels.

Embodiments of the present invention provide a genetically modified (GM) corn plant expressing Wpgd1 and/or Wpgd2 and GM corn seeds that containing Wpgd1 and/or Wpgd2 and which are capable of expressing Wpgd1 and/or Wpgd2.

In view of the aspects discussed herein, an embodiment of the invention is directed to a plant or plant cell that has been genetically modified to increase the plant's or plant cell's tolerance to heat. In particular, cells of the plant are genetically modified with the stable introduction of a transgene encoding PGD1 and PGD2 fused in-frame with a plastid targeting sequence.

In view of the aspects discussed herein, embodiments of the invention also provide a plant cell or a plant which is genetically modified, the genetic modification leading to the import of heat stable 6PGDH into the plastids of the plant cell or the plant. Compared to a corresponding unmodified wild-type plant cells or wild-type plants, the genetically modified plant cell or plant has enhanced thermotolerance and improved yield during heat stress.

In yet another aspect of the invention, a plant with altered expression levels of a polypeptide described above or a plant with altered expression or activity levels of an above-described polypeptide may be modified according to the methods disclosed herein. Further, a plant lacking a polynucleotide sequence encoding a polypeptide described above or substantially lacking a polypeptide described above may be modified according to the methods disclosed herein. The plant may be any plant, including, but not limited to, *Arabidopsis*, maize, barley, rice, and *Setaria*.

In yet another aspect of the invention, the disclosed methods may apply to an isolated plant material of a plant, including, but not limited to, plant tissue, fruit, seed, plant cell, embryo, protoplast, pollen, and the like. In yet another aspect of the invention, the invention is a transgenic plant tissue culture of regenerable cells, including, but not limited to, embryos, meristematic cells, microspores, protoplast, pollen, and the like.

F. Use in Breeding Methods

The genetically modified plants of the disclosure can be used in a plant breeding program. The goal of such plant breeding according to the invention is to combine, in a single variety or hybrid, various desirable traits. For field crops, these traits preferably include, for example, resistance to diseases and insects, tolerance to heat and drought, tolerance to chilling or freezing, reduced time to crop maturity, greater yield and better agronomic quality. With mechanical harvesting of many crops, uniformity of plant characteristics such as germination and stand establishment, growth rate, maturity and plant and ear height also is desirable. Traditional plant breeding is an important tool in developing new and improved commercial crops. This disclosure encompasses methods for producing a plant by crossing a first parent plant with a second parent plant wherein one or both of the parent plants is a transformed plant displaying a phenotype as described herein.

Plant breeding techniques known in the art and used in a plant breeding program include, but are not limited to, recurrent selection, bulk selection, mass selection, backcrossing, pedigree breeding, open pollination breeding, restriction fragment length polymorphism enhanced selection, genetic marker enhanced selection, doubled haploids and transformation. Often combinations of these techniques are used.

The development of hybrids in a plant breeding program requires, in general, the development of homozygous inbred lines, the crossing of these lines and the evaluation of the progeny of the crosses. There are many analytical methods available to evaluate the result of a cross. The oldest and most traditional method of analysis is the observation of phenotypic traits. Alternatively, the genotype of a plant can be examined.

A genetic trait which has been engineered into a particular plant using gene editing or transformation techniques can be moved into another line using traditional breeding techniques that are well known in the plant breeding arts. For example, a backcrossing approach is commonly used to move a modified plant to an elite inbred line and the resulting progeny would then comprise the modification. Also, if an inbred line was used for the transformation or editing, then those plants could be crossed to a different inbred line in order to produce a hybrid plant. As used herein, "crossing" can refer to a simple X by Y cross or the process of backcrossing, depending on the context as is understood in the art.

The development of a hybrid in a plant breeding program involves three steps: (1) the selection of plants from various germplasm pools for initial breeding crosses; (2) the selfing of the selected plants from the breeding crosses for several generations to produce a series of inbred lines, which, while different from each other, breed true and are highly homozygous and (3) crossing the selected inbred lines with different inbred lines to produce the hybrids. During the inbreeding process, the vigor of the lines decreases. Vigor is restored when two different inbred lines are crossed to produce the hybrid. An important consequence of the homozygosity and homogeneity of the inbred lines is that the hybrid created by crossing a defined pair of inbreds will always be the same. Once the inbreds that give a superior hybrid have been identified, the hybrid seed can be reproduced indefinitely as long as the homogeneity of the inbred parents is maintained.

Transgenic plants of the present disclosure can be used to produce, e.g., a single cross hybrid, a three-way hybrid or a double cross hybrid. A single cross hybrid is produced when two inbred lines are crossed to produce the F1 progeny. A double cross hybrid is produced from four inbred lines crossed in pairs (A×B and C×D) and then the two F1 hybrids are crossed again (A×B) times (C×D). A three-way cross hybrid is produced from three inbred lines where two of the inbred lines are crossed (A×B) and then the resulting F1 hybrid is crossed with the third inbred (A×B)×C. Much of the hybrid vigor and uniformity exhibited by F1 hybrids is lost in the next generation (F2). Consequently, seed produced by hybrids is consumed rather than planted.

The disclosed invention is further defined in the following examples. It should be understood that these examples are given by way of illustration only. From the above discussion and these examples, one skilled in the art can ascertain the essential characteristics of embodiments of the disclosed invention. Without departing from the spirit and scope thereof, one skilled in the art can make various changes and modifications of the invention to adapt it to various usages and conditions. All publications, including patents and non-patent literature, referred to in this specification are expressly incorporated by reference herein.

G. Engineering Heat Stable Endosperm Enzymes

Heat labile enzymes can be a cause for yield loss during heat stress. Loss of enzyme activity in carbon metabolism, particularly in starch synthesis, is thought to reduce grain-fill in cereals. The amyloplast-localized PGD3 isozyme is necessary for normal grain-fill. Example 1 shows that PGD3 is heat sensitive, making this plastid isozyme a candidate for engineering a more heat stable form. The best-characterized example of an engineered, heat-stable cereal endosperm enzyme is AGPase. AGPase is a potential rate-limiting step in starch biosynthesis, and its activity is reduced by heat stress. Engineered heat stable variants of AGPase can increase seed weight up to 64% over normal controls depending on temperatures during early seed development.

Heat stable mutants of AGPase were first identified and characterized in maize. These variants may confer heat stability by stabilizing large and small subunit interactions. Some plant species, such as potato, have heat stable AGPase. Site-directed mutagenesis and domain swapping experiments have been used to engineer additional heat-stable variants of AGPase. Expression of these heat stable AGPase variants can increase grain yield in maize, wheat, and rice.

As shown in Example 1, maize 6PGDH activity has heat-stable cytoplasmic isozymes and a heat-sensitive plastid isozyme. The plastid version is known to be critical for starch accumulation and adding a heat-stable isozyme to the amyloplast may improve grain yield under heat stress growth conditions. A simple approach to increasing heat stability of 6PDGH in the amyloplast would be to target the more heat stable cytosolic isozymes into the amyloplast during endosperm development.

H. Transit Peptide and Protein Subcellular Localization

During the evolution of eukaryotic cells, most of the genomes of the mitochondrial and plastid endosymbionts were transferred to the nucleus. Consequently, many plastid proteins are encoded by the nuclear genome and synthesized in the cytosol and need to be post-translationally targeted to the plastid. N-terminal targeting signals called transit peptides direct plastid precursors through the TOC/TIC translocation machinery in the outer and inner chloroplast envelope membranes. After import into the chloroplast, the transit peptide is proteolytically cleaved from the precursor to allow the mature protein to properly fold in the chloroplast. Most proteins can be targeted to the chloroplast by constructing a translational fusion of a chloroplast transit peptide with the coding sequence of the protein of interest. Sequences of transit peptides are extremely diverse, and there is no strict consensus sequence motif for chloroplast transit peptides. Instead, transit peptides and chloroplast proteins have a bias for amino acid composition that can be predicted using statistical models. Therefore, it is important to identify a biochemically characterized transit peptide to allow precise engineering of a translational fusion of 6PGDH to target to the plastid.

I. The ZmGBSS (Waxy1) N-Terminal Transit Peptide

The waxy1 (wx1) locus in maize encodes the granule-bound starch synthase (GBSS), which is expressed only in the endosperm, pollen, and embryo sac. This enzyme is nuclear-encoded, translated in the cytosol, and imported into the amyloplast in the maize endosperm. The wx1 locus has been intensively studied due to its function in determining starch quality. The WX1 transit peptide was characterized in detail. The N-terminus of the mature 59 kDa WX1 protein was purified from amyloplasts, sequenced and compared with the predicted precursor protein sequence from cDNA sequence data to identify the 72 amino acid transit peptide. The WX1 transit peptide was shown later to mediate chloroplast import of a translational fusion protein into purified maize, pea, and potato chloroplasts. These experiments demonstrated WX1 to be a reliable transit peptide to target proteins to endosperm amyloplasts. Importantly, the cleavage site for the WX1 transit peptide has been experimentally determined, allowing fusion proteins to be designed that will contain no WX1 sequence after import into the plastid.

J. Endosperm Specific Maize Promoters

Zeins are the main storage proteins in the maize endosperm. α-Zeins are encoded by three multimember 19-kDa α (Z1A, Z1B and Z1D) subfamilies and one multimember 22-kDa (Z1C) subfamily (Song et al., 2003). The 27-, 16-, and 50-kDa γ-zeins and the 15-KDa β-zein are encoded by single genes. All zein genes are specifically expressed during maize endosperm development.

The promoter regions from zeins have been used for endosperm-specific expression in transgenic plants. The 5' flanking regions of zein genes are conserved between cereal storage protein genes along with other endosperm expressed maize genes allowing the zein promoter sequences to be identified. Specific binding of protein factors was shown to be present in the endosperm cell nuclei from a 19-kDa α-zein promoter. Quayle and Feix (1992) showed that a 43-bp sequence in the 19-kDa α-zein promoter enhanced transcriptional activity in transiently transformed maize protoplasts. Ueda and Messing, 1991, identified a 1.1 kbp promoter sequence from the 27-kDa γ-zein locus that effectively drove expression of reporter genes in endosperm cell culture. Later, Ueda et al. (1994) identified a 23-bp motif in the 27-kDa γ-zein promoter that could be mutated to increase transcriptional response to the OPAQUE2 transcription factor. The 27-kDa γ-zein was shown to have strong endosperm expression during grain filling stages from 10 to 25 DAP, which makes this promoter a good choice for endosperm-specific expression.

The examples demonstrate distinct enzymatic properties and roles of 6PGDH isozymes in maize. There was significant evidence for compartment-specific biological roles of maize 6PGDH isozymes. PGD3 is critical for starch accumulation and is localized in the plastid. The PGD1 and PGD2 isozymes are cytosolic and do not affect seed phenotype when knocked down. Therefore, compartment localization was shown to determine the differences between the isozymes. Differential roles of starch biosynthetic isozymes were shown to be compartment dependent for AGPase, as overexpression of the cytoplasmic version enhances seed weight. While the plastidic version, if overexpressed showed moderate increases to even decreases on seed weight in rice.

As shown in Example 1, PGD3 is heat sensitive, while PGD1 and PGD2 are heat stable. In order to provide extra heat-stable isozymes to the plastids, constructs of PGD1 and PGD2 were fused to a previously characterized N-terminal transit peptide, from the maize WX1 protein, previously shown to target proteins to either chloroplasts or amyloplasts. The two engineered versions of 6PGDH import into isolated pea chloroplasts in vitro, indicating that the targeting sequence is functional.

Transgenic maize plants were generated with a strong endosperm promoter to specifically target 6PGDH function in the endosperm amyloplasts. The use of tissue-specific native promoters are expected to improve trait precision breeding. Transformants showed increased 6PGDH enzyme activity, and isozyme activity assays suggest the increase is due to higher levels of PGD1 and PGD2. Endosperm with the presence of the transgenes also enhanced heat stability in vitro. Wpgd1 and Wpgd2 transgenes rescue the pgd3 defective kernel phenotype suggesting the fusion proteins are targeted to the amyloplast. These results conclusively prove that plastid 6PGDH activity is critical for proper seed development. The endosperm-specific transgenes rescued embryo development suggesting that the endosperm specific function may impact embryo development. However, it is possible that the endosperm-specific promoter may express a low level of WPGD1 or WPGD2 in the embryo. There is some precedent for non-autonomous effects of transgenes expressed from zein promoters. Heat-stable AGPase transformed with an endosperm specific promoter show increases in yield based on increased seed number instead of increased final seed weight.

The preliminary field experiment suggests the transgene can mitigate grain yield losses in heat stressed conditions by enhancing individual kernel weight. These data support a model in which the amyloplast PPP contributes to maize yield loss during heat stress. However, follow-up yield trials must be conducted to determine the consistency of the heat stability traits and grain yield, as some of the events show better yield maintenance than others.

This project also illustrates the potential value of genetic engineering to generate traits that would be nearly impossible to obtain through traditional breeding methods. For PGD1 or PGD2 to be targeted to the plastid, an exon encoding a chloroplast transit peptide would need to insert in correct orientation upstream of the endogenous gene. This type of insertion could potentially occur over the course of evolution, but it is not clear whether there would be a selective advantage under non-stressed culture conditions. Alternatively, germplasm could be screened for more heat tolerant alleles of Pgd3. However, transgenic germplasm can be introgressed into elite temperate germplasm without the risk of carrying extra deleterious genes that can cause linkage drag, which is likely to occur in traditional breeding programs. For those reasons, direct genetic approaches can save breeding selection time and have the potential to enhance germplasm diversity options for breeding programs.

The transgenic approach could also be converted to a cisgenic construct, because maize endogenous genes were engineered and expressed in the plant with an endogenous promoter. For the designed engineered construct to be considered a complete cisgenic approach, non-maize components of the vector would need to be replaced, such as an endogenous selectable marker driven by a maize promoter and terminator.

In Example 2, the cytosolic 6PGDH proteins are engineered to be targeted to plastids during endosperm development. The goal is to produce heat-stable, amyloplast-localized 6PGDH activity. The rationale was to supply the metabolic intermediates in the endosperm amyloplast that are affected when PGD3 activity is reduced under heat stress conditions. It is shown that transgenics expressing engineered 6PGDH isozymes during endosperm development increase the heat tolerance of 6PGDH activity and rescue pgd3 mutant endosperm phenotypes.

5. Examples

This invention is not limited to the particular processes, compositions, or methodologies described, as these may vary. The terminology used in the description is for the purpose of describing the particular versions or embodiments only, and is not intended to limit the scope of the present invention which will be limited only by the appended claims. Although any methods and materials similar or equivalent to those described herein can be used in the practice or testing of embodiments of the present invention, the preferred methods, devices, and materials are now described. All publications mentioned herein, are incorporated by reference in their entirety; nothing herein is to be construed as an admission that the invention is not entitled to antedate such disclosure by virtue of prior invention.

Example 1: Maize 6PGDH Isozyme Roles are Distinct and Compartment-Dependent

A. Materials and Methods
1. General Methods
Maize plants were grown in the field at the University of Florida Plant Science research and Education Unit in Citra, Fla., or in a greenhouse at the Horticultural Sciences Department in Gainesville, Fla. The pgd3-umu1 allele was maintained in the color-converted W22 inbred genetic background as heterozygous plants and self-pollinated to obtain homozygous mutant kernels (see Spielbauer et al., 2013). The pgd3-umu1 allele was also introgressed into the B73 inbred line until the BC6S1 generation. The pgd1-null; pgd2-125 double mutant genetic stock was obtained from Julia Bailey-Serres at the University of California, Riverside and maintained through self-pollination (see Bailey-Serres et al., 1992). The pgd1-null; pgd2-125 double mutant was introgressed into the color-converted W22 inbred line using marker assisted selection to develop a BC5S2 double mutant homozygous stock.

RNA was extracted from W22 14 DAP leaves using Trizol™ and DNaseI (NEB) following the manufacturers' protocols. Full-length cDNA for PGD1 and PGD2 were synthesized with the SuperScript® III First-Strand Synthesis System (ThermoFisher™). Pgd and Pgd2 cDNA was amplified and cloned into a TOPO Zero Blunt® (ThermoFisher™) vector. DNA was extracted from positive cloned colonies, using the QIAprep® Miniprep Kit (Qiagen™) and was later sequenced using the M13 Forward and Reverse primers. The sequences were compared with the B73 reference genome at MaizeGDB (see Andorf et al., 2016) and Gramene (see Tello-Ruiz et al., 2016) using the software ProSeq™3.5 (see Filatov, 2009).

The pgd1-null and pgd2-125 alleles were sequenced from the homozygous double mutant stock genomic DNA. Products spanning the open reading frame of each gene were amplified with a high-fidelity Phusion® (NEB) DNA polymerase using the following primers:

PGD1L1:
(SEQ ID NO: 68)
GCGTCAGAAGCACCAACC,

PGD1R1:
(SEQ ID NO: 69)
ACATCACCTTTGGAGCATGG,

PGD1L2:
(SEQ ID NO: 70)
CGCCATCTCCTCCTACACTG,

PGD1R2:
(SEQ ID NO: 71)
CCGCTCTGGATTTTCTTTGA,

PGD1R3:
(SEQ ID NO: 72)
CTCAGGAACCTCGAGTCCAA,

PGD1L3:
(SEQ ID NO: 73)
CAACAGTGAGCTGCACCAG,

PGD1R4:
(SEQ ID NO: 74)
ACATCACCTTTGGAGCATGG,

PGD1L4:
(SEQ ID NO: 75)
CCAAGATCTTCCAGGGTGAC,

PGD2L1:
(SEQ ID NO: 76)
GCCCAGACGTCAGGTATGTT,

PGD2R1:
(SEQ ID NO: 77)
TTTCTGTCAAGGGGAAAGGA,

PGD2R3:
(SEQ ID NO: 78)
GGTCTATGAATCAAAATGCAGGT,

PGD2L3:
(SEQ ID NO: 79)
CGGCCAGAGATCTTTAATGG,

PGD2R4:
(SEQ ID NO: 80)
GGACTGTCCATTTCCCAGTT,

PGDL4:
(SEQ ID NO: 81)
GGAATTGAATATGGTGACATGC,

PGD2R5:
(SEQ ID NO: 82)
AGGCAGCTTGCCTGTCTATG,

PGD2L5:
(SEQ ID NO: 83)
GCCTCAACCTTGGTGAGCTA.

PCR product sequences were compared with the full-length cDNA sequences from W22 and B73 to identify mutations using the software ProSeq™3.5 (see Filatov, 2009).

Mutant protein sequences were obtained with the NCBI™ ORF-finder (see Wheeler et al., 2003) and the ExPASy Translate™ tool (see Gasteiger et al., 2003). Protein alignments and phylogenetic analysis performed by the software Phylogeny™ (see Dereeper et al., 2008) and Clustal Omega™ (see Sievers et al., 2011). Protein structure modeling was completed with Phyre 2™ (see Mezulis et al., 2015).

Co-dominant markers were designed for genotyping the pgd1-null and pgd2-125 mutations. The pgd1-null allele could be detected with an insertion-deletion (InDel) product using the primers: PGD1C-Terminal F: CTACGAGAGGGTCGACATGC (SEQ ID NO:84) and PGD1 C-Terminal R: TGCAGGAAATCTCATTACCG (SEQ ID NO:85). The pgd2-125 allele was detected with a cleaved amplified polymorphic sequence (CAPS) marker using the primers: PGD2 C-Terminal F: GCATCAAGAAGGCGTACGAT (SEQ ID NO:86), PGD2 C-Terminal R: TTACTCGACACGGTGGCATA (SEQ ID NO:87). This product was then digested by BsmFI (NEB) to detect mutant and normal alleles.

2. In Vivo Heat Stability

A controlled heat-stress experiment was performed at the University of Wisconsin-Madison Biotron facility (see biotron.wisc.edu). Climate and lighting controlled growth rooms were used to grow three replicates of 50 color-converted W22 inbred maize plants in each room. Heat stress was applied during seed development starting at 12 DAP until maturity. Three different temperature conditions were used: (1) Control room: 28° C. day/17° C. night, (2) Hot day/Normal night: 38° C. day/17° C. night, and (3) Hot day/Hot night: 38° C. day/28° C. night. Growth room temperature was set to increase and decrease in increments with the room to be at daytime high temperature for approximately 8.5 hours total. For example, the temperature regime for hot day/hot night was set as (28° C. at 4:00 AM, 33° C. at 7:45 AM, 38° C. at 11:30 AM, 33° C. at 8:00 PM, and 28° C. at 11:59 PM). Whole ears were harvested in July 2014, at 14, 18, 22, 26, and 30 days after pollination and maturity. Kernels were segregated into the bottom, middle, and top portion of the ear, flash frozen and stored at −80° C. until used for enzyme activity analysis.

The full-length genes of 6PGDH were cloned from cDNA from B73 using the Gateway™ system (Life Technologies™) with the Zero Blunt@ TOPO vector (see James et al., 2000; Kulcinskaja et al., 2013) (ThermoFisher™). The open reading frame (ORF) of Pgd1, Pgd2, and Pgd3 were subcloned into the pENTR vector (Gateway™ ThermoFisher™) (see Katzen, 2007), and then recombined into the binary vector pB7-MP:GFP (see Brandner et al., 2008). The PGD1-GFP, PGD2-GFP, and PGD3-GFP vectors were then transformed into *Agrobacterium* competent cells.

*Nicotiana benthamiana* was grown in a growth chamber with 16/8 hours day/night light. *Agrobacterium* ($OD_{600}$=0.6) was infiltrated into leaves of 4 weeks old plants using a needleless syringe as described by Gault et al., 2017. Fluorescence in epidermal cells of *N. benthamiana* leaves was visualized by spinning disk confocal microscopy (X81-DSU-Olympus™) 48 hours after transient transformation.

Seeds were harvested for enzyme activity at immature grain filling stages of 14, 18, 22, 26 and 30 DAP. Immature kernels were excised from the cobs, frozen in liquid nitrogen, and stored at −80° C. until used for enzyme extraction.

Frozen tissues from total or dissected kernels were ground in liquid nitrogen and extraction buffer (100 mM Tris-HCl pH 7.5, 30 mM 1,4-Dithiothreitol (DTT), 15% (v/v) glycerol) added to the tissue in a 1:1 weight to volume ratio of tissue to buffer. All additional extraction procedures were carried out on ice or at 4° C. Crude extracts were cleared of tissue by centrifugation for 20 minutes at 1,600×g. The upper aqueous phase was collected, placed in a new tube, and kept in ice.

Protein samples were loaded on a native polyacrylamide gel at 10% and electrophoresed at 30 mA for 2.5 hours at 4° C. 6PGDH activity was assayed by incubating gels at room temperature for 30 minutes in the dark with 6PGDH staining solution (0.1 mg/mL NADP+, 0.1 mg/mL nitro blue tetrazolium, 0.1 mg/mL phenazine methosulfate, 0.5 mg/mL 6-phosphogluconate, 100 mM Tris-HCl pH 7.5) (see Bailey-Serres et al, 1992). Activity stain solution was prepared just before use. Gels were rinsed in water, dried, and imaged with a flatbed scanner. Gel band intensity was quantitated using ImageJ™ (see Abramoff et al., 2004).

Spectrophotometric determination of total 6PGDH was adapted from Debnam and Emes, 1999. Total protein was extracted with 300 L of cold extraction buffer that contained, 50 mM HEPES (pH 7.5), 200 mM KCl, 10 mM MgCl2, 2.5 mM EDTA (pH 7.5) and 5% sucrose. The extract was centrifuged for 20 minutes at 1600×g at 4° C. The supernatant was transferred to a new tube, desalted using Zeba™ desalting columns (ThermoFisher™), and kept in ice. Total protein concentration was measured using a commercial Bradford™ assay (Bio-Rad™) following the manufacturer's protocol.

Total enzyme activity was measured quantitatively using spectrophotometric absorbance. Embryo enzyme activity is approximately six-fold higher than endosperm activity. Crude extract protein concentration was adjusted to achieve similar linear ranges of absorbance with 120 μg of endosperm protein and 20 μg of embryo protein added to 500 L volume substrate solution. G6PDH was detected with 0.1 mM NADP+, 0.1 mM glucose-6-phosphate, 0.2 mM Tris-HCl, 0.5 mM MgCl2. 6PGDH was detected with 0.1 mM NADP+, 0.1 mM 6-phosphogluconate, 0.2 mM Tris-HCl, 0.5 mM $MgCl_2$. Absorbance at 340 nm was measured for 10 minutes with one reading collected per minutes. Absorbance was regressed against time, and the slope was used to determine enzyme activity in Units/mg protein from the Lambert-Beer Law in which A/min=e-c-1 where A is absorbance, e is the coefficient of extinction for NADP+, c is the protein concentration, and 1 is the path length.

3. In Vitro Heat Stability Experiments

Protein extracts were separated in equal aliquots (10-20 μL) and placed in a 42° C. water bath. Control aliquots were kept in ice during the heat treatment. Heat-treated aliquots were placed in ice at 5 minute intervals. 6PGDH enzyme activity was assayed from control and heat-treated protein extracts at the end of all heat treatments.

B. Experimental Results

1. Sequencing pgd1 and pgd2 Reference Alleles

The pgd1; pgd2 double mutant stock was in an undefined genetic background with the molecular cause for loss of PGD1 and PGD2 activity unknown. The molecular nature of the pgd1-null and pgd2-125 mutations were determined by sequencing the two genomic loci from the pgd1-null; pgd2-125 genetic stock.

The pgd1-null allele has a small insertion that alters the 3' end of the ORF with 39 novel codons replacing the C-terminal 15 amino acids of the normal protein coding sequence. FIG. 8 shows an alignment between 6PGDH protein sequences from *Saccharomyces cerevisiae* (Gnd1), wild-type (wt) PGD1, and mutant pgd1-null. Underlined is the Domain-C region on Gnd1. Highlighted in yellow is the 37 amino acid insertion in the PGD1 mutant. The crystal structure of *S. cerevisiae* Gnd1 revealed that the enzyme is a dimer with the C-terminal domain promoting dimerization (He et al., 2007). In yeast, the C-terminal domain is not essential for dimer formation, but it also functions to control the binding of substrate and release of product making the domain indispensable for activity (He et al., 2007).

Figure 9:
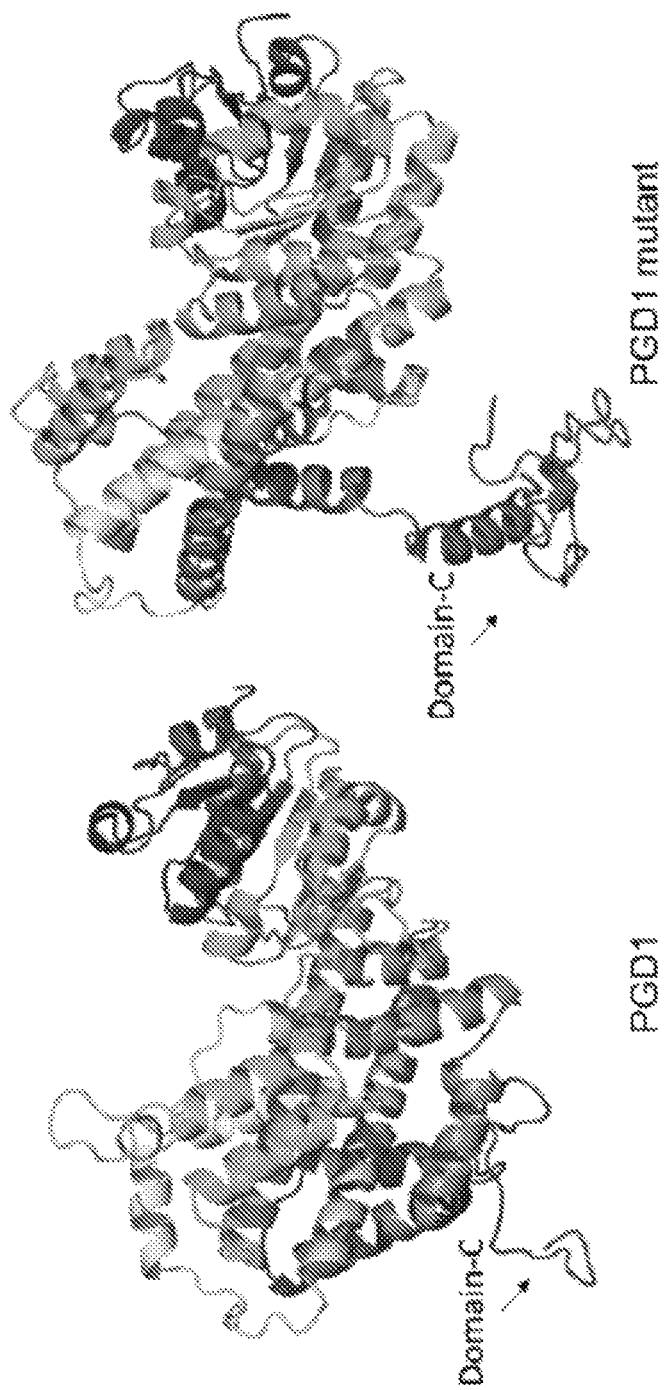
FIG. 9 shows a comparison of the protein structure models for native PGD1 and the homozygous PGD1 mutant protein according to one embodiment of the present invention.

FIG. 9 is a comparison of the protein structure models for native PGD1 and the homozygous PGD1 mutant protein according to one embodiment of the present invention. The predicted C-terminal Domain-C is shown in red. Structures were modeled using Phyre2™. Predicted crystal structures of pgd1 show the effects on the Domain-C (FIG. 9).

The pgd2-125 mutant allele was also amplified and sequenced. FIG. 10 is a protein alignment between *Saccharomyces cerevisae* 6PGDH (Gnd1), PGD2 and PGD2 mutant proteins according to one embodiment of the present invention. The Domain-C region on Gnd1 is underlined. The Gnd1 R456, and the ZmPGD2 R460 are shown in yellow highlight. The R-T substitution is shown in red lowercase.

Figure 11:
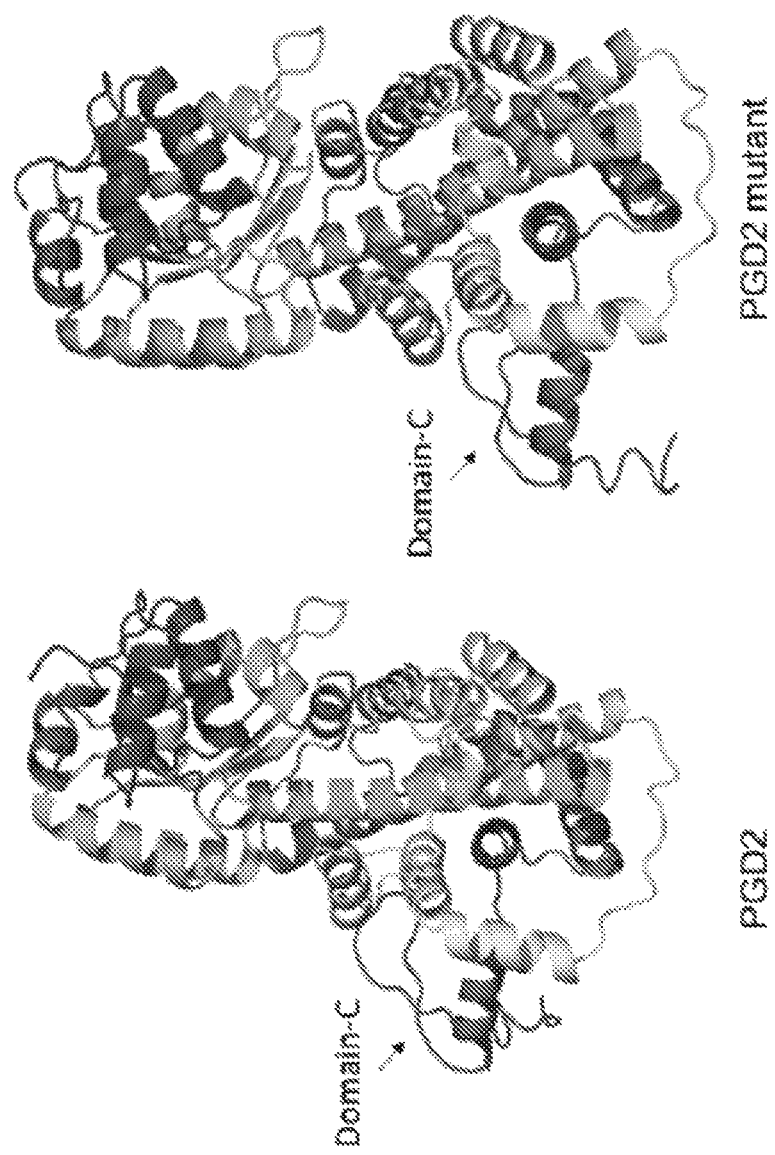
FIG. 11 is a drawing showing a comparison of the protein structure models for native PGD2 and the homozygous PGD2 mutant protein according to one embodiment of the present invention.

FIG. 11 is a comparison of the protein structure models for native PGD2 and the homozygous PGD2 mutant protein according to one embodiment of the present invention. The predicted C-terminal Domain-C is shown in red. Structures were modeled using Phyre2™. As shown in FIG. 10, a missense mutation in the PGD2 ORF changes a charged Arg residue to the non-charged amino acid Thr. The R460T mutation is located at the C-terminal domain (see FIG. 10) and is predicted to alter Domain-C structure (FIG. 11). This Arg is an important residue for binding and anchoring the 6-phosphogluconate (6PGD) substrate as well as the NADP+ coenzyme in yeast (Tetaud et al., 1999).

The pgd1-null; pgd2-125 double mutant has some residual 6PGDH enzyme activity (Bailey-Serres and Nguyen, 1992). Both mutant alleles are predicted to produce proteins, and neither allele directly affects the active site of the enzyme.

Figure 12:
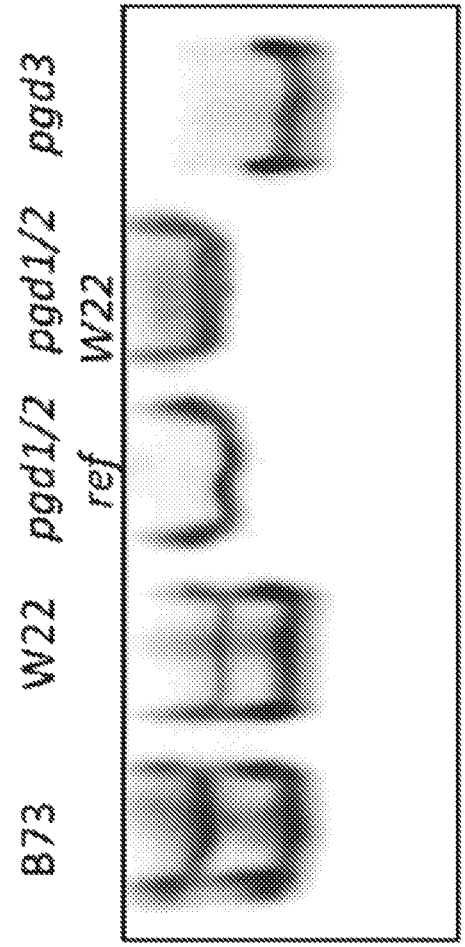
FIG. 12 is an image of a gel showing the mutations in the 6PGDH isozyme activity according to one embodiment of the present invention.

2. 6-Phosphogluconate Dehydrogenase Seed Defective Phenotype is Compartment Dependent The identification of the mutation sites pgd1-null and pgd2-125 allowed the design of PCR markers to introgress the double mutant into the W22 inbred background. FIG. 12 is an image of a gel showing the mutations in the 6PGDH isozyme activity according to one embodiment of the present invention (native PAGE stained for the activity of 6-phosphogluconate dehydrogenase). FIG. 12 shows a native PAGE activity assay comparing PGD3 (top band) with PGD1/PGD2 (bottom band) in the B73 and W22 inbred lines and mutant genetic stocks. The reference pgd1; pgd2 double mutant stock was backcrossed (BC) to W22 for five generations followed by two self-pollination generations for a homozygous pgd1; pgd2 BC5S2 introgression into W22 (pgd1/2, W22). B73 and W22 showing total activity, being the upper band represented by PGD3 homodimer and lower band by PGD1 and PGD2 homodimers and heterodimer. In the pgd1/pgd1; pgd2/pgd2 mutant, there is absence of the lower band, in the reference background (Bailey-Serres et al., 1992) and W22 background. In the pgd3/pgd3 mutant there is absence of the upper band.

Figure 13:
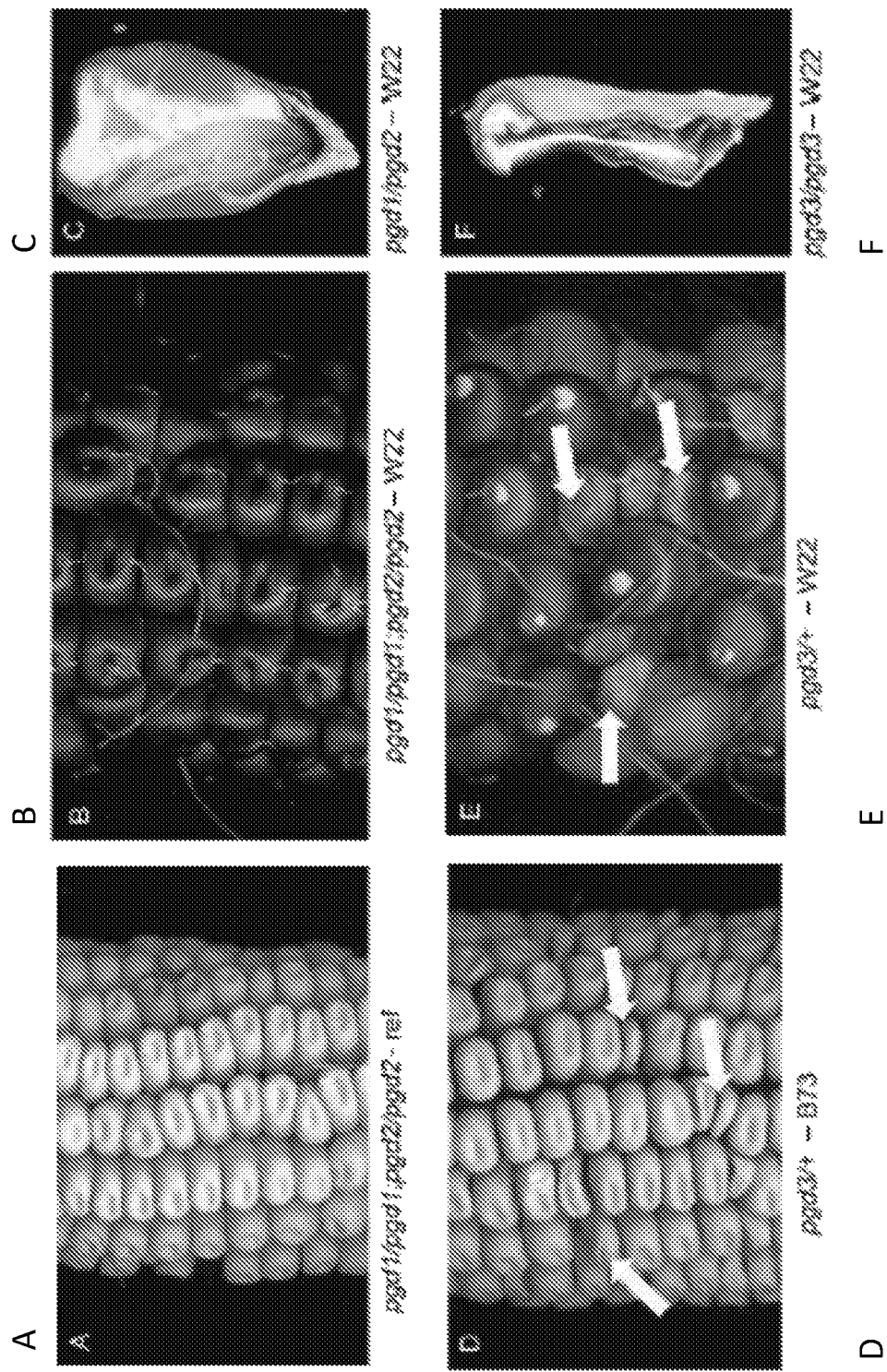
FIG. 13A, FIG. 13B, FIG. 13C, FIG. 13D, FIG. 13E, and FIG. 13F are images illustrating that PGD3 knockout can cause a seed defective phenotype according to one embodiment of the present invention.

FIG. 13A through F are images illustrating that PGD3 knockout can cause a seed defective phenotype according to one embodiment of the present invention. See FIG. 13A, showing a homozygous ear pgd1/pgd1; pgd2/pgd2 in the reference background (mixed partially introgressed into B73, (Bailey-Serres et al., 1992)); FIG. 13B, showing a homozygous ear pgd1/pgd1, pgd2/pgd2 in W22; FIG. 13C, showing a sectioned pgd1/pgd1, pgd2/pgd2 homozygous kernel into W22; FIG. 13D, showing a heterozygous pgd3/+ ear in the B73 background; FIG. 13E, showing a heterozygous pgd3/+ ear in the W22 background; FIG. 13F, showing a sectioned pgd3/pgd3 homozygous kernel into W22. Neither PGD1 nor PGD2 activity is detectable, and the double mutant plant develops normal kernels (see FIG. 13). By contrast, the pgd3 mutant in either B73 or W22 inbred backgrounds has severe grain-fill and defective embryo phenotypes.

To experimentally test whether PGD1 and PGD2 are exclusively cytoplasmic, transient expression constructs were designed with PGD1 and PGD2 fused in-frame with GFP as a C-terminal fusion. FIG. 14 shows that both PGD1 and PGD2 fusion proteins accumulate in the peripheral region of N. benthamiana epidermal pavement cells, consistent with cytosolic localization. The PGD3-GFP fusion co-localized with chloroplasts. These data confirm that PGD1 and PGD2 are localized to the cytosol and that double mutants of these cytoplasmic isozymes do not have kernel phenotypes even in the W22 inbred genetic background. Thus, plastid-localized 6PGDH appears to be the sole isozyme required for normal maize kernel development.

Figures 14A, 14B, 14C, 14D, 14E, 14F, 14G, 14H, 14I:
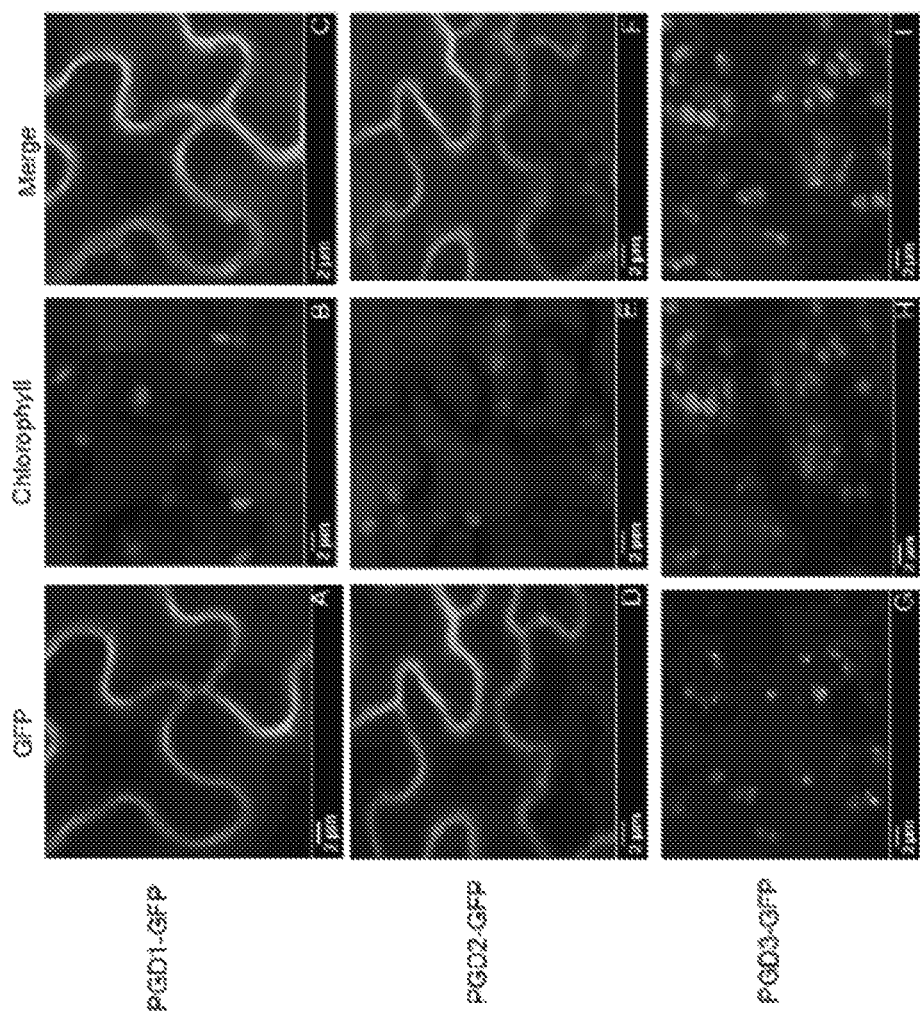
FIG. 14 is a set of images illustrating that PGD1 and PGD2 are cytosolic proteins, and PGD3 is plastidic according to one embodiment of the present invention.

Additional details concerning FIG. 14 are as follows. FIG. 14A through I are images illustrating that PGD1 and PGD2 are cytosolic proteins, and PGD3 is plastidic according to one embodiment of the present invention. N. benthamiana leaves are agroinfiltrated with constructs expressing PGD1-GFP (FIG. 14A, FIG. 14B, FIG. 14C), PGD2-GFP (FIG. 14D, FIG. 14E, FIG. 14F) and PGD3-GFP (FIG. 14G, FIG. 14H, FIG. 14I). Protein expression and localization was imaged utilizing fluorescence microscopy at 40× magnification with filters specific for GFP, chlorophyll, and merged images. Spectrophotometric enzyme activity assays combined with sub-cellular fractionation of root extracts found that about 70% of wild-type 6PGDH activity is associated with the cytosol, and 30% is associated with plastids. In pgd1; pgd2 double mutants, the remaining activity is localized predominantly to plastids. Mutations of the maize pgd3 locus disrupt the plastid-localized activity. The maize PGD3 protein has a short, atypical chloroplast targeting sequence, which was shown to be functional by transiently expressing a PGD3-GFP fusion protein in N. benthamiana (see FIG. 14).

3. Seed G6PDH and 6PGDH Activity are Responsive to Heat Stress

To understand how the grain-filling stage was affected by heat, a heat stress experiment was conducted. As shown in Table 4, W22 plants were shifted into three temperature regimes beginning at 12 DAP: normal day/normal night, hot day/normal night, and hot day/hot night.

TABLE 4

Controlled Temperature Experiment
Day/Night Average Temperatures.

| Room | Temperature ° C. | Temperature ° F. |
| --- | --- | --- |
| Normal | 28/17 | 82.4/62.6 |
| Normal/Hot | 38/17 | 100.4/62.8 |
| Hot/Hot | 38/28 | 100.4/82.4 |

Figure 15:
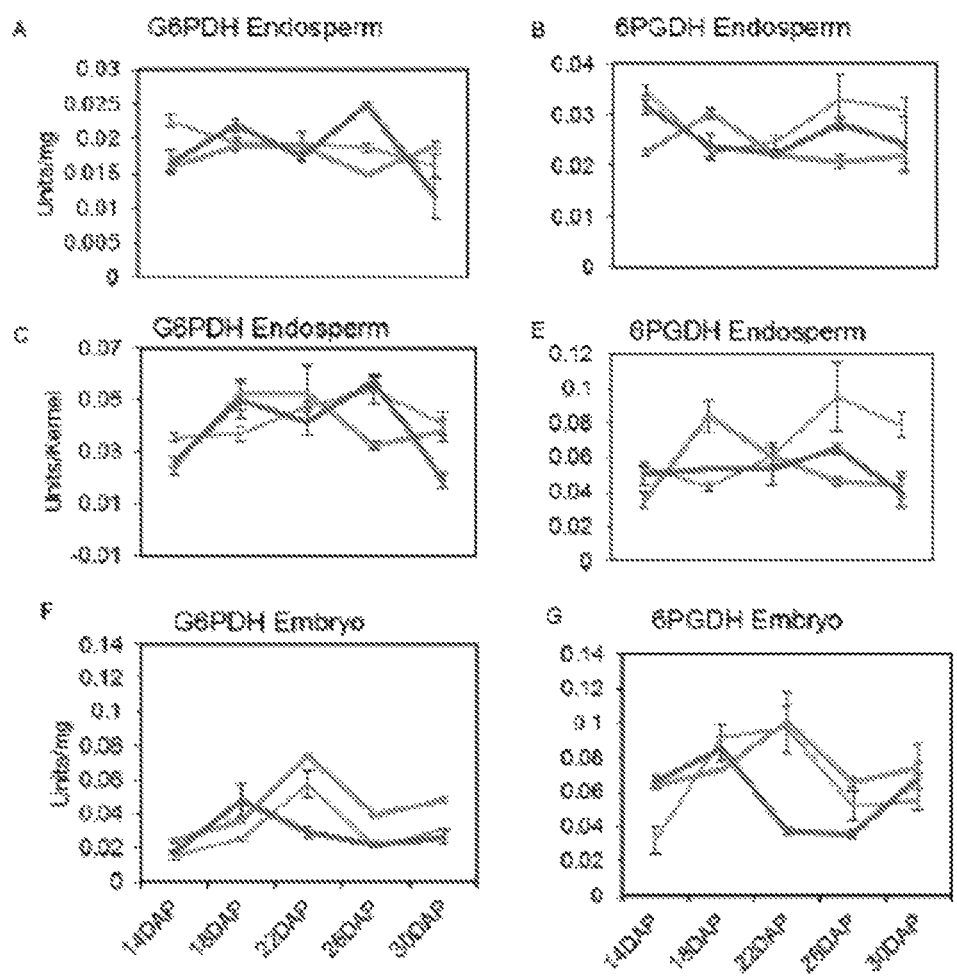
FIG. 15A, FIG. 15B, FIG. 15C, FIG. 15E, FIG. 15F, and FIG. 15G are graphs illustrating that total 6PGDH enzyme activity is affected in vivo by heat treatment during grain filling stages, according to one embodiment of the present invention.

Immature kernels were collected throughout the kernel filling developmental stages from 14 DAP to 30 DAP. Total enzyme activity was measured, comparing endosperm and embryo activity for G6PDH and 6PGDH (see FIG. 15). FIG. 15A through FIG. 15G are graphs illustrating that total 6PGDH enzyme activity is affected in vivo by heat treatment during grain filling stages, according to one embodiment of the present invention. Endosperm (Units/mg) G6PDH (FIG. 15A), 6PGDH (FIG. 15B), Endosperm (Units/kernel) G6PDH (FIG. 15C), 6PGDH (FIG. 15D), and Embryo (Units/mg) G6PDH (FIG. 15E), and 6PGDH (FIG. 15F). Treatments are as follows: Normal (blue), Normal/Hot (orange), Hot/Hot (red). Samples were taken at 14, 18, 22, 26, and 30 days after pollination (DAP). Error bars indicate ±SD of three biological replicates.

FIG. 16A through F are graphs showing 6PGDH specific isozymes activities according to one embodiment of the present invention. 6PGDH isozyme activity was analyzed using a native PAGE gel stained for 6PGDH activity. Enzyme activities from the samples from the Normal conditions (N) and Hot/Hot conditions (H), from 14, 18, 22, 26, and 30 DAP are shown. The upper band is PGD3; the lower band PGD1/2. FIG. 16A and FIG. 16B are images of native PAGE gels for Endosperm and for embryo, respectively. Quantitation of the bands was calculated using IMAGEJ™. Differences between the band intensity were calculated comparing total enzyme activity with the specific isozyme activity % (Isozyme/Total) for Normal day/Normal night, Endosperm and Embryo in FIG. 16C and FIG. 16D, respectively; and for Hot Day/Hot Night for Endosperm and Embryo in FIG. 16E and FIG. 16F, respectively.

Figure 16:
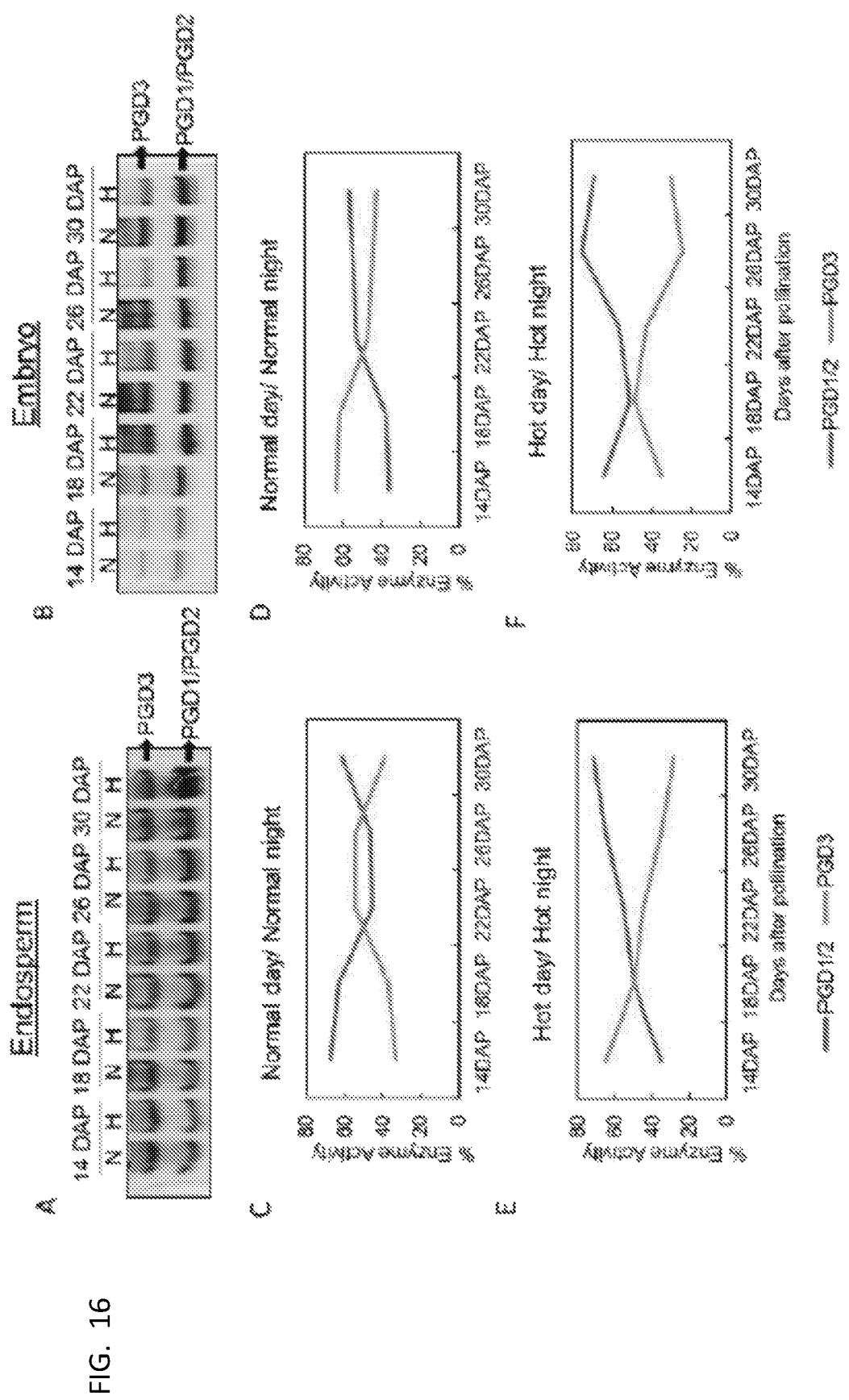
FIG. 16A, FIG. 16B, FIG. 16C, FIG. 16D, FIG. 16E and FIG. 16F are gels (A and B) and graphs (C, D, E, and F) showing 6PGDH specific isozymes activities according to one embodiment of the present invention.

As shown in FIG. 16, endosperm enzyme activity significantly decreased by about 50% at 26 DAP for both enzymes. Embryo enzyme activity was reduced by 60% at 22 DAP. Native PAGE assays were used to evaluate isozyme-specific activity during the treatments. (see FIG. 16A and FIG. 16B). Relative levels of plastid (PGD3) and cytoplasmic (PGD1/PGD2) activity were quantified for the normal/normal and hot/hot samples based on band intensity (see FIG. 16C, FIG. 16D, FIG. 16E and FIG. 16F). Relative levels of PGD3 activity peaked and declined at earlier time points in hot temperature treatments, and in the endosperm decreased along the developmental time points. The declines in PGD3 activity correspond to overall decline in 6PGDH activity as shown in FIG. 15. Consistent with an overall reduction in oxPPP activity in response to heat stress, the 6PGDH substrate, 6-PGD, also decreases at 22 to 30 DAP in hot/hot endosperm samples.

4. PGD3 Enzyme Activity is Sensitive to Heat

To determine how enzyme activity of the 6PGDH isozymes are directly affected by heat, crude extracts from endosperm were treated at 42° C. and isozyme activity was assayed by native PAGE. Results are shown in FIG. 17. FIG. 17A is a photograph of a gel showing PGD3 and PGD1/

PDG2 in W22 endosperm, 14 DAP. FIG. 17B and FIG. 17C are graphs illustrating the thermostability of 6PGDH isozymes.

As shown in FIG. 17A through C, PGD3 activity decreased in proportion to the length of heat treatments, while PGD1 and PGD2 did not appear affected (FIG. 17A). FIG. 17A, FIG. 17B and FIG. 17C illustrate that the thermostability of 6-phosphogluconate dehydrogenase isozymes is affected by in vitro heat treatments according to one embodiment of the present invention. FIG. 17A presents native PAGE results, stained for the activity of 6PGDH. This figure illustrates enzyme (6PGDH) activity in identical endosperm protein extracts during a time course of heat treatment. The samples were treated on ice for 0 minutes (control) and from 5 minutes to 45 minutes at 42° C. The upper band shows PGD3 activity and the lower band shows PGD1/PGD2 activity with most PGD3 activity lost by 40 minutes of heat treatment. The combined results suggest PGD3 loses 40-80% of activity after only 20 minutes of heat treatment, while the PGD1 and PGD2 enzymes are very stable in these treatments.

FIG. 17B is a graph illustrating spectrophotometric measurements of total 6PGDH activity from endosperm extracts during a time course of heat treatment. This figure provides endosperm spectrophotometric measurements for the decrease of enzyme activity for total activity in the B73, pgd1/pgd2 and pgd3 mutants, treated at 42° C. for 20 minutes. As shown in FIG. 17B, mutant pgd3/pgd3 endosperm only contain PGD1 and PGD2 activity, while double mutant pgd1/pgd1; pgd2/pgd2 endosperm only contain PGD3 activity. To quantify the decrease of PGD3 enzyme activity, endosperm extracts of B73, pgd1; pgd2 and pgd3 were treated at 42° C., and total enzyme activity was measured spectrophotometrically. In the pgd3 mutant, only PGD1 and PGD2 isozyme activity remains, this cytosolic activity is stable during heat treatment. "Normal" extracts have a mix of PGD1, PGD2, and PGD3 isozymes and shows a decrease of 25% activity during the heat treatment. The pgd1; pgd2 mutant only has plastidic PGD3 activity, which decreases by 50% in this heat treatment. Thus, enzyme activity is resistant to heat treatment only in pgd3 mutants showing PGD1 and PGD2 are heat resistant. Heat sensitivity is enhanced when only PGD3 activity is present in the pgd1; pgd2 double mutant.

Enhanced heat sensitivity is observed when only PGD3 activity is present in the pgd1; pgd2 double mutant and the heat sensitivity of PGD3 is even more apparent in embryo extracts (see FIG. 17C). FIG. 17C is a graph illustrating spectrophotometric measurements of total 6PGDH activity from embryo extracts during a time course of heat treatment. Spectrophotometric measurements were taken to determine the decrease of enzyme activity in the B73 and pgd1/pgd2, treated at 42° C. for 20 minutes. Error bars in this figure indicate ±SD of three biological replicates. The total activity from the three isozymes in the normal embryos decreases by 60% after heat treatment. In the pgd1, pgd2 mutant, the remaining PGD3 activity decreases by 80% during heat treatment. These results indicate that PGD3 activity is more sensitive to high temperatures, while PGD1 and PGD2 activity is unaffected by heat.

5. Post-Translational Differences Between Cytosolic and Plastid 6PGDH Isozymes

Figure 18:
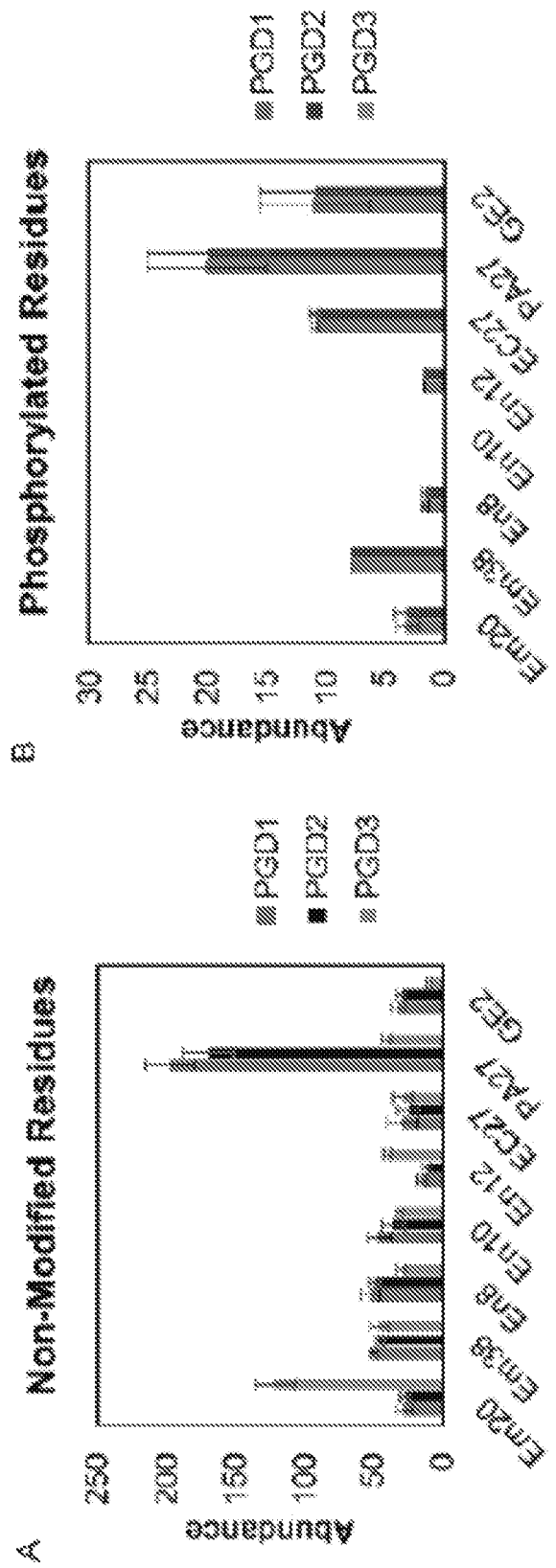
FIG. 18A and FIG. 18B are graphs showing the abundance of non-modified residues and phosphorylated residues from maize different tissues according to one embodiment of the present invention.

FIG. 18A and FIG. 18B are graphs showing the abundance of non-modified residues and phosphorylated residues from maize tissues according to one embodiment of the present invention. The X axis indicates the tissues sampled: Embryo 20 DAP (Em20), Embryo 38 DAP (Em38), Endosperm 8 DAP (En8), Endosperm 10 DAP (En10), Endosperm 12 DAP (En12), Endosperm Crown 27 DAP (EC27), Pericarp/Aleurone 27 DAP (PA27), and Germinated Embryo 2 DAG (GE2). The Y axis indicates the total protein abundance calculated for non-modified residues (FIG. 18A) for PGD1, PGD2 and PGD3. Phosphorylation abundance calculated for phosphorylated residues (FIG. 18B) for PGD1, PGD2 and PGD3. These graphs were adapted from the Atlas of maize proteotypes database (Walley et al., 2013; maizeproteome.ucsd.edu).

Public protein abundance data at the Maize Proteome database were analyzed to understand potential causes of heat stability differences, (maizeproteome.ucsd.edu; Walley et al., 2013). PGD3 is most abundant in 20 DAP embryo. In the endosperm, PGD3 protein was detected in all stages sampled (FIG. 18A). By contrast, PGD1 and PGD2 proteins are at their lowest levels in 12 DAP endosperm. PGD1 and PGD2 have evidence of phosphorylated residues that are not observed for PGD3. Two phosphopeptides were identified for PGD1 (TTSKVDETVQR (SEQ ID NO:88 and IFQGDYYSTGSPVDKAQLVEDVR (SEQ ID NO:89) that have a highly scored phosphorylated serine (S316). PGD2 had only TTSKVDETVQR (SEQ ID NO:90) classified as a phosphopeptide with T34, T35 and S36 having significant scores for phosphorylation. However, these residues were not consistently recovered as phosphopeptides for all tissues tested (see FIG. 18B).

FIG. 19 provides a sequence alignment illustrating post-translational regulatory differences of the cytosolic and plastid Zm6PGDH protein sequences between maize PGD1, PGD2 and PGD3. The observed phosphopeptides are in red, and the phosphorylated residue S316 is highlighted in green. The peptides identified with acetylated K residues are highlighted with yellow and interesting amino acids substitutions on PGD3 are shown in lowercase blue.

A multiple sequence alignment of the maize PGD1, PGD2, and PGD3 proteins shows multiple amino acid substitutions in PGD3 near the post-translationally modified residues. K and T in TTSKVDETVQR (SEQ ID NO:88) are conserved in all three proteins, but T and S are substituted with A, as well as, E is substituted with S (see FIG. 19). The S316 residue in PGD1 is not conserved in either PGD2 or PGD3 suggesting that this phosphorylation site is unlikely to be needed for activity.

Proteomics of acetylation sites in mature maize leaves identified two acetylated K residues shown in lower case: TTSkVDETVQR (SEQ ID NO:91) and FLSGLkDER (SEQ ID NO:92) for PGD1 and PGD2 on leaves (Walley et al., 2016). Interestingly one of the acetylated sites (FIG. 19 yellow highlight) is in close proximity to the phosphorylated T in KVDET (SEQ ID NO:93). The acetylation sites are highly conserved between PGD1, PGD2, and PGD3. The only amino difference noted is near the site FLSGLkDER (SEQ ID NO:94), where phenylalanine (F) is substituted by tyrosine (Y) in PGD3 (see FIG. 19). It is possible, however, that acetylation was not detected for PGD3 because the experiment was performed with mature leaves, in which PGD3 activity is absent.

Figure 20:
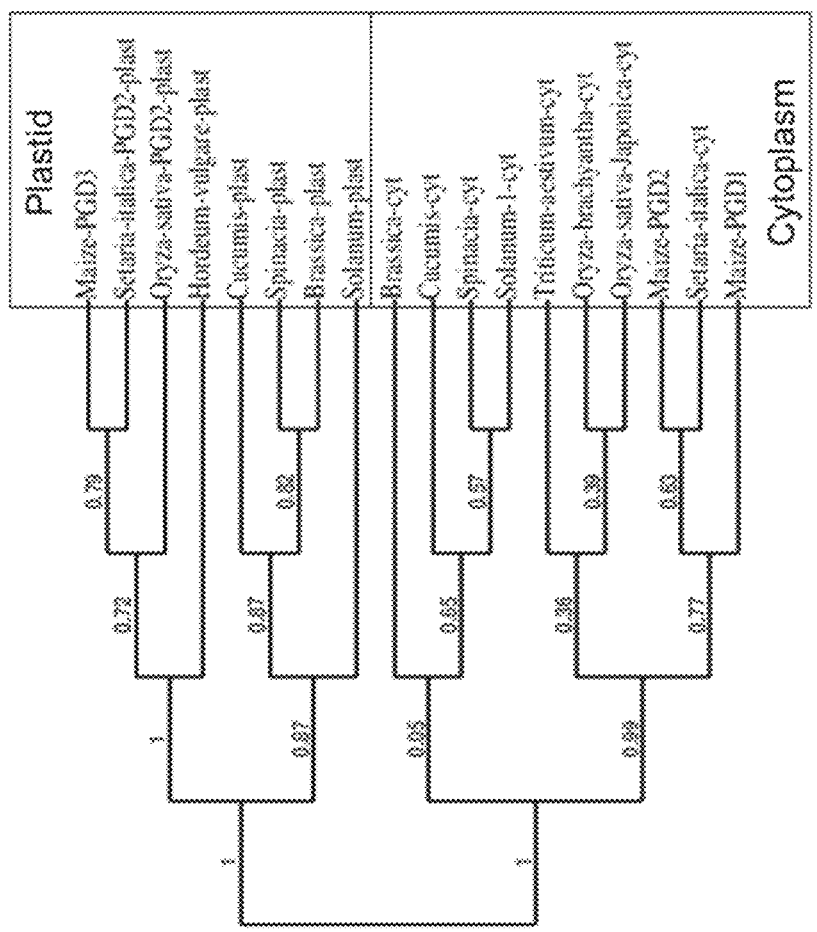
FIG. 20 is a similarity tree from closely related 6PGDH.

Prior phylogenetic analysis of plant 6PGDH isozymes has showed that the plastid and cytosolic genes derive from a duplication of a single ancestral cyanobacterial gene (Krepinsky et al., 2001). The divergence of plastid and cytosolic 6PGDH is examined to determine how likely heat-stable and heat-labile isozymes might be found in other species. FIG. 20 is a similarity tree of closely related 6PGDH. 6PGDH protein sequences were blasted to find closely related isozymes using Clustal™ Omega. Compartment localization prediction was performed using Target-P™. As shown in FIG. 20, plastid and cytosolic enzymes group into separate branches. Within each clade, the enzymes group following species phylogeny with a clear delineation of grasses and eudicot crops.

FIG. 21 is a protein sequence alignment between closely related 6PGDH in the indicated plants, including 6PGDH from *Hordeum vulgare* (barley), *Oryza sativa* (rice), *Oryza brachyantha*, Maize, *Setaria italica*, *Spinacia*, *Brassica*, *Cucumis*, *Solanumm*, and *Brassica*. In red are the predicted phosphopeptides. The predicted phosphorylated residue S316 is highlighted in green. The acetylated residues are highlighted in yellow, interesting amino acids substitutions are indicated in lowercase blue, and other conserved residues are indicated in red.

Comparing multiple sequence alignments of maize 6PGDH with other closely related species suggests that some of the cytosolic post-translational modifications in cytosolic isozymes may be conserved (see FIG. 21). The phosphopeptide KVDET (SEQ ID NO:93) is conserved within plastidic and cytosolic isozymes in eudicots, while the plastidic isozymes from grasses all have amino acid substitutions on T35 and S36. The phosphopeptide PVDKAQLVEDVR (SEQ ID NO:95) is conserved between the cytosolic versions of maize, wheat, setaria and rice. The phosphorylated residue GsPVDK (SEQ ID NO:96) with S316 is exclusive from PGD1 between the cytosolic 6PGDH versions. Surprisingly, S316 is also conserved in plastidic 6PGDH for *Solanum*, *Brassica* and *Cucumis*. This conservation suggests that the phosphorylated residue is not unique to the cytoplasmic clade of 6PGDH isozymes. The acetylated K residues are conserved in all isozymes analyzed. Combining all of these evolutionary data, there is no solid evidence for compartment-specific, post-translational modifications that could explain differences in heat sensitivity of the maize isozymes. Even though compartment specific enzymes are highly conserved, it still is necessary to determine differences in heat sensitivity experimentally.

C. Conclusions

In this example, functional differences between the three maize 6PGDH isozymes were identified. First, by sequencing the pgd1-null and pgd2-125 alleles, C-terminal polymorphisms that are consistent with the strong reductions in isozyme activity were identified. Introgression of the pgd1; pgd2 double mutant into W22 inbred line, militates against differences in inbred genetic background as the primary cause of the pgd3 seed phenotype. The lack of a pgd1; pgd2 seed phenotype in W22 confirms distinct biological functions for 6PGDH in the cytosol and plastid. Subcellular localization experiments indicate that PGD1 and PGD2 are exclusive to the cytosol. However, as discussed by (Hölscher et al., 2016), there are C-terminal peroxisomal targeting motifs that a C-terminal GFP would block.

The controlled temperature experiment showed that G6PDH and 6PGDH enzyme activities are responsive to heat stress during grain-fill. These two limiting oxPPP enzyme activities are expected to change the level of available reductant for catabolic metabolism. By analyzing 6PGDH isozyme enzyme activity, the plastidic isozyme was shown to be most strongly affected during heat treatment. Similar in vitro heat treatment experiments further showed that PGD3 is a heat sensitive enzyme, while PGD1 and PGD2 are more heat stable.

The plastid and cytosolic 6PGDH enzymes have diverged in protein sequence due to their differential evolutionary origin. As already shown for AGPase, amino acid substitutions and post-translational changes can influence protein stability, however comparisons of post-translational modifications in PGD1, PGD2, and PGD3 did not point to any conclusive differences underlying heat stability of cytosolic 6PGDH. Although there is clear evidence for distinct clades of cytosol and plastid isozymes in grasses, experimental evidence is needed to determine if similar differences in heat sensitivity exist in 6PGDH isozymes of closely related grasses such as barley, rice, and *Setaria*.

Example 2. Engineering a More Heat Stable Maize Amyloplast 6PGDH

A. Materials and Methods

1. General Comments

This example describes engineering a more heat stable maize amyloplast 6PGDH and a series of tests to determine if the Wpgd1 and Wpgd2 genes behaved as designed. First, in vitro chloroplast import assays showed that both fusion proteins could be targeted to the chloroplast. Second, transgenic kernels have higher levels of 6PGDH activity and the total activity was more resistant to in vitro heat treatments. Third, Wpgd1 and Wpgd2 were crossed into pgd3 mutant stocks and were able to rescue the mutant allele to give full grain-fill and normal kernel development in homozygous mutant pgd3 plants. Combined these results indicate that the WPGD1 and WPGD2 proteins are expressed, heat resistant, and localized in the amyloplast.

2. 6PGDH Constructs for Chloroplast Import

The ORFs for wild-type Pgd1, Pgd2 and Pgd3 were amplified from cDNA prepared from 14 DAP B73 kernel RNA using gene-specific primers and cloned into pGEM3Z. The Wx1 transit peptide translational fusions with Pgd1 and Pgd2 were synthesized by GenScript™ and named Wpgd1 and Wpgd2. A Kozak consensus sequence 5' of the Wx1 start codon was included to aid in eukaryotic translation. HindIII and BamHI cleavage sites were designed at the 5' and 3' end of the Wpgd1 and Wpgd2 fusions to facilitate cloning into diverse vectors. Both fusion genes were cloned in pGEM3Z (Promega™) for in vitro transcription/translation. See Table 2 and Table 3, which show fused sequences of the N-terminal transit peptide from the Waxy gene with Pgd1 and Pgd2. In blue are the HindIII and BamHI cleavage sites, in orange the Kozak consensus sequence, and highlighted in yellow are the Wx1 codons for the peptide cleavage site sequence before the Pgd1 and Pgd2 start codon.

3. Import Assay

Intact pea chloroplasts were isolated from 9 to 10-day-old pea (*Pisum sativum*) seedlings as described previously (Cline, 1986). Chloroplasts were re-suspended in import buffer (50 mM HEPES/KOH pH 8.0, 0.33 M sorbitol) at 1 mg/mL chlorophyll for in vitro import assays.

Transcripts for all five constructs (Pgd1, Pgd2, Pgd3, WPgd1, and WPgd2) were synthesized in vitro using SP6 polymerase (Promega™) and then translated using wheat germ extracts in the presence of [$^3$H]-leucine as described by (Cline, 1986). Translation products were diluted with one volume of 60 mM leucine in 2× import buffer prior to use. Diluted translation products were incubated with intact chloroplasts (0.33 mg chlorophyll/mL) and 5 mM Mg-ATP (Sigma) for 20 min in a 25° C. water bath under 120 µE/m$^2$/s light. After import, intact chloroplasts were purified again by centrifugation at 4,000 g for 8 min at 2° C. on a 35% Percoll import buffer cushion and washed twice with 1 mL import buffer on ice. Finally, chloroplasts were re-suspended in import buffer at 1 mg/mL of chlorophyll.

4. Protease Treatment in Purified Chloroplasts

From the purified chloroplasts, two thirds of the final extraction volume was pelleted at 1,000 g for 6 minutes and re-suspended in 2× import buffer. Thermolysin (SIGMA) was added (2 mg protein/mL in 2× import buffer, 10 mM $CaCl_2$) and incubated at 4° C. for 40 minutes. Protease digestion was stopped by adding 50 µL of 50 mM EDTA-import buffer, and chloroplasts were re-purified with a 35% Percoll cushion in import buffer with 5 mM EDTA. The chloroplasts were resuspended in 5 mM EDTA-import buffer, transferred to a new tube, pelleted, and resuspended in 20 mM EDTA.

5. Chloroplast Fractionation

Chloroplast pellets were lysed by re-suspending in 10 mM HEPES/KOH pH 8.0 at 2 mg/mL chlorophyll and incubated for 10 minutes, followed by addition of one volume of 2× import buffer. Plastid lysates were centrifuged at 150,000×g for 20 minutes at 4° C. to isolate soluble proteins (stroma) from membrane proteins (pellet). Stroma and membrane proteins were brought to a 50 µL volume in 2× import buffer. Precursor proteins, purified chloroplasts, thermolysin treated chloroplasts, stroma and membrane samples were separated on a 10% SDS-PAGE gel followed by fluorography analysis as described (Cline et al., 1989).

6. Transgenic Plant Generation

The Wpgd1 and Wpgd2 ORFs were sub-cloned in the binary vector pIPK-27-MCSBAR. This vector has a 27 kDa γ-zein promoter and a NOS terminator to drive endosperm specific expression of the Wpgd1 and Wpgd2 genes. The pIPK-27-MCSBAR vector expresses the herbicide resistance gene (Bar) as a selectable marker to glufosinate-ammonium. The Wpgd1 and Wpgd2 constructs were transformed by *Agrobacterium tumefaciens* into the Hill genotype at the Iowa State University Plant Transformation Facility (agron.iastate.edu/ptf/). To transformants were grown in a greenhouse at Iowa State University and self-pollinated. There were six independent events of Wpgd1 named Wpgd1-A to Wpgd1-F and seven independent Wpgd2 events named Wpgd2-A to Wpgd2-G. All the events were crossed to B73 or W22 inbred lines for introgression.

7. Genotyping

The presence of the transgene was determined by PCR. Primers were designed to amplify each construct specifically at the promoter-ORF junction and the ORF-terminator junction with the primers:

```
ZWPGD1F:
                                      (SEQ ID NO: 97)
AAATAGGCCGGAACAGGAC;

PGD1R:
                                      (SEQ ID NO: 98)
ACAGAGATGGGGAACCCTTT;

ZWPGD2F:
                                      (SEQ ID NO: 99)
AAACTGAGCCACGCAGAAGT;

PGD2R:
                                      (SEQ ID NO: 100)
CTTGGAGGTCGTCCTGTTGT;

WPGD1F:
                                      (SEQ ID NO: 101)
CAGGGCATGAACATCATCAA;

NostR1
                                      (SEQ ID NO: 102)
GTTTGCGCGCTATATTTTGTT;

WPGD2F:
                                      (SEQ ID NO: 103)
GGCATGAACATCATCAAGG;
and NostR2:
                                      (SEQ ID NO: 104)
ATCCTAGTTTGCGCGCTATATTT.
```

The pgd3 locus was genotyped with a codominant marker using the PGD3L, PGD3R, and Tir5 primers as described. PCR amplification was carried out in a volume of 20 µL containing 100 ng of template DNA, 4 µL of 5× Green GoTaq Reaction Buffer (Promega™) 1.0 µL of 2 mM each dNTP, 25 pmol of primer and 15 units Taq DNA Polymerase. Thermocycling conditions were set to 94° C. for 1 minute, 60° C. for 1 minute, 72° C. for 1 minute, for 40 cycles.

8. Enzyme Activity

Immature kernels for enzyme activity were harvested at 14, 22 and 26 DAP. Kernels were excised from cobs, frozen in liquid nitrogen, and stored at −80° C. until used for enzyme extraction. Prior to protein extraction, frozen kernels were quickly dissected, and embryos were used to genotype each endosperm sample.

9. Isozyme Activity

Isozyme activity between transgenic and non-transgenic siblings was determined by a native-PAGE activity assays as described in Example 1.

10. Total Enzyme Activity

Spectrophotometric determination of total 6PGDH activity between transgenic and non-transgenic siblings was performed by spectrophotometry as described in Example 1.

11. In Vitro Heat Stability Experiment

Protein extracts were separated in equal aliquots (10-20 µL) and placed in a 50° C. water bath. Control aliquots were kept in ice during the heat treatment. Heat-treated aliquots were placed in ice at 10-minute intervals during 30 minutes. 6PGDH enzyme activity was assayed from control and heat-treated protein extracts.

12. Complementation Test

Heterozygous pgd3-umu1/+ plants were crossed with Wpgd2/− and Wpgd1/− Hill $T_1$ plants. $F_1$ progeny from the crosses were evaluated for glufosinate resistance, self-pollinated, and genotyped for the transgenes and pgd3. $F_2$ kernels from each ear were separated according to visual phenotype. Segregation ratios were evaluated with χ2 tests for goodness of fit for ¼ expected mutants from pgd3/+ or pgd3/+; Wpgd/− self-pollinated ears. In addition, pgd3/+; Wpgd/− self-pollinated ears showed partially rescued kernels, which were tested for fit to 3/16 rescued kernels and 1/16 pgd3 mutant kernels. To determine quantitative effects of the Wpgd transgenes, individual kernel weights were collected with a microbalance, and the kernels were then genotyped for pgd3 and presence of the transgene.

13. Germination Test

Rescued pgd3 mutant kernels were germinated in greenhouse conditions to observe plant phenotypes. Greenhouse conditions were set for a 12-hour light cycle from 9 am to 9 pm, a maximum temperature of 32° C., and a minimum temperature of 18° C. Germination and plant phenotypes were scored on 15, 35 and 85 days after germination (DAG).

14. Mutant pgd3/pgd3 Seed Rescue

Mutant pgd3 embryos were rescued in tissue culture using Murashige and Skoog (MS) media with 3% sucrose and 0.2% asparagine monohydrates. Mutant seeds were harvested at 21 DAP from self-pollinated pgd3/+ ears. Kernels were sterilized with 70% ethanol for 2 minutes followed by 20% (v/v) bleach for 15 minutes. Next, the seeds were washed with sterilize water three times. The pericarp was carefully cut to excise the immature embryo, which then was incubated on the sterilized MS medium in a growth chamber at 30° C. during the day and 20° C. at night.

15. Seed Qualitative and Quantitative Composition

Individual kernel weight and composition was determined with a microbalance and single-kernel Near Infrared Reflectance (NIR) spectroscopy to predict density, volume, starch, protein and oil as described in Spielbauer et al., 2009 and Gustin et al., 2013.

16. Seed Phenotypic Analysis

Mature kernel sagittal sections were cut by hand with a utility knife and imaged on a flatbed scanner.

B. Experimental Results

1. Engineering Heat Stable Amyloplastic 6PGDH Isozymes

To be able to target the cytosolic heat stable versions of 6PGDH to the plastid, the N-terminal WX1 transit peptide was translationally fused to both Pgd1 and Pgd2 by gene synthesis. Protein sequencing of the mature WX1 protein identified the transit peptide processing site as VVC, which was used as C-terminal end of the recombinant transit peptide for PGD1 and PGD2. The rationale was to produce native PGD1 and PGD2 protein and enzymatic activity after targeting to the amyloplast with the goal of allowing native folding in the new compartment. These fusion proteins were named WPGD1 and WPGD2. Table 1, above, shows WX1 N-terminal transit peptide, i.e., WPGD1 and WPGD2 predicted N-terminal protein sequence, according to one embodiment of the present invention. The WX1 N-terminal transit peptide is shown with the red highlighted amino acids (VVC) indicating the required processing site for cleavage after import into plastids. The N-terminal M for both PGD1 and PGD2 was directly fused to the C-terminal WX1 processing site.

2. WPGD1 and WPGD2 Import into Plastids In Vitro

Figure 22:
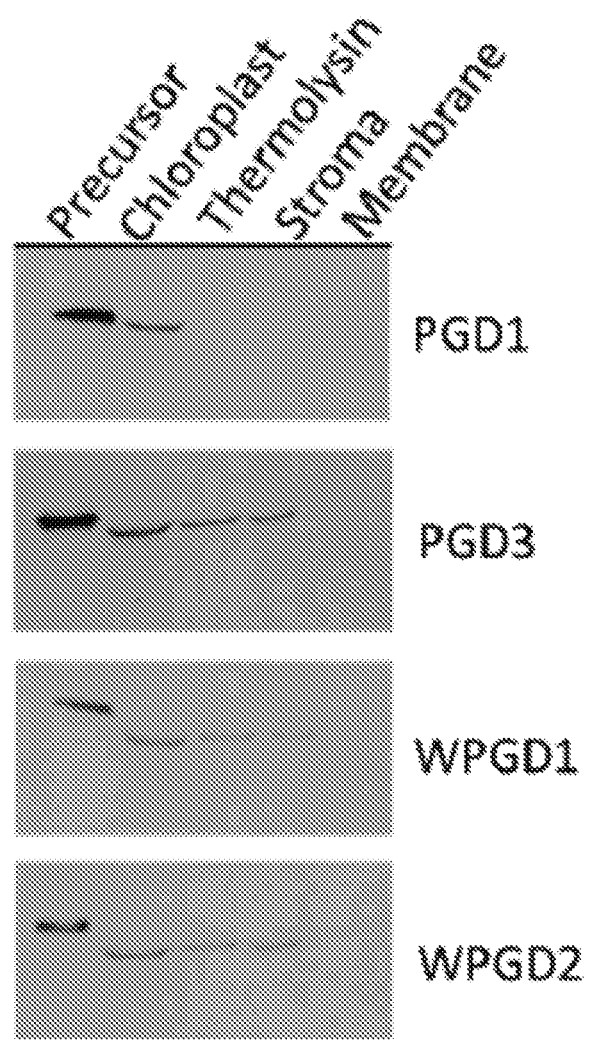
FIG. 22 is a set of images illustrating 6PGDH amyloplastic engineered versions are imported into plastids according to one embodiment of the present invention.

The engineered proteins were imported to purified pea plastids in an in vitro import assay. See FIG. 22. FIG. 22 is a set of images of gels illustrating that 6PGDH amyloplastic engineered versions are imported into plastids according to one embodiment of the present invention. The proteins used for the experiment were: PGD1– native cytosolic, PGD3– native plastidic, and WPGD1 and WPGD2, engineered plastidic proteins. Precursor proteins, chloroplasts after the import assay only purified by a Percoll™ gradient, thermolysin treated chloroplasts, and disrupted plastids separated by stroma (soluble) and membrane.

In vitro chloroplast import assays tested the WPGD1 and WPGD2 proteins for targeting and cleavage of the transit peptide (see FIG. 22). Purified pea chloroplasts were incubated with radiolabeled in vitro transcribed and translated precursor proteins. The chloroplasts were re-purified after import using Percoll™ cushions. To remove radiolabeled protein stuck on the outer chloroplast membrane, the chloroplasts were treated with thermolysin and re-purified. Thermolysin-treated chloroplasts were disrupted with hypotonic lysis and centrifuged to separate soluble (stroma) and membrane fractions.

FIG. 22 shows that although wild-type PGD1 associates with chloroplasts, the protein is outside of the outer envelope, as thermolysin digests the radiolabeled protein. By contrast, PGD3 is resistant to thermolysin treatment and fractionates as a soluble protein, which demonstrates the expected pattern for a soluble, plastid-localized enzyme. The WPGD1 and WPGD2 signals follow the pattern of PGD3, indicating the engineered proteins are imported into plastids. The smaller size of the WPGD1 and WPGD2 proteins indicate that the WX1 transit peptide is cleaved after import.

3. WPGD1 and WPGD2 Increase 6PGDH Activity and Heat Stability in Developing Kernels The Wpgd1 and Wpgd2 genes were cloned into the pIPK27-MCSBAR binary transformation vector with a γ-zein 27 kDa endosperm-specific promoter. FIG. 3 and FIG. 4 show the schematic of the expression constructs in which the maize endosperm-specific promoter drives expression and the nopaline synthase terminator (nosT) from *Agrobacterium tumefaciens* is used to terminate transcription. These T-DNA constructs were transformed into the inbred line Hill (Armstrong et al., 1991) at the Iowa State University Transformation facility. $T_0$ plants were self-pollinated and $T_1$ plants were crossed into the B73 and W22 inbred lines.

Kernels from $T_0$ plants were characterized for 6PGDH enzyme activity. Embryos were genotyped for the transgene, and endosperms were assayed for enzyme activity. FIG. 23A. FIG. 23B, FIG. 23C, and FIG. 23D are graphs and images showing that total enzyme activity is enhanced in the presence of the transgene on $T_0$ endosperm according to one embodiment of the present invention. Spectrophotometric measurements comparing the activity of a normal Hill endosperm with WPGD1 (FIG. 23A) and WPGD2 (FIG. 23C) on $T_0$ on Hill background. Error bars indicate ±SD of three biological replicates T-test comparing averages between Normal and Transgenic siblings. WPGD1 p-value: 0.0007 and WPGD2 p-value:0.0366. FIG. 23B is an image of a native PAGE gel stained for the activity of 6PGDH comparing Normal Samples and WPGD1-C. FIG. 23D is an image of a native PAGE gel stained for the activity of 6PGDH comparing Normal Samples and WPGD2-B samples.

Figure 23:
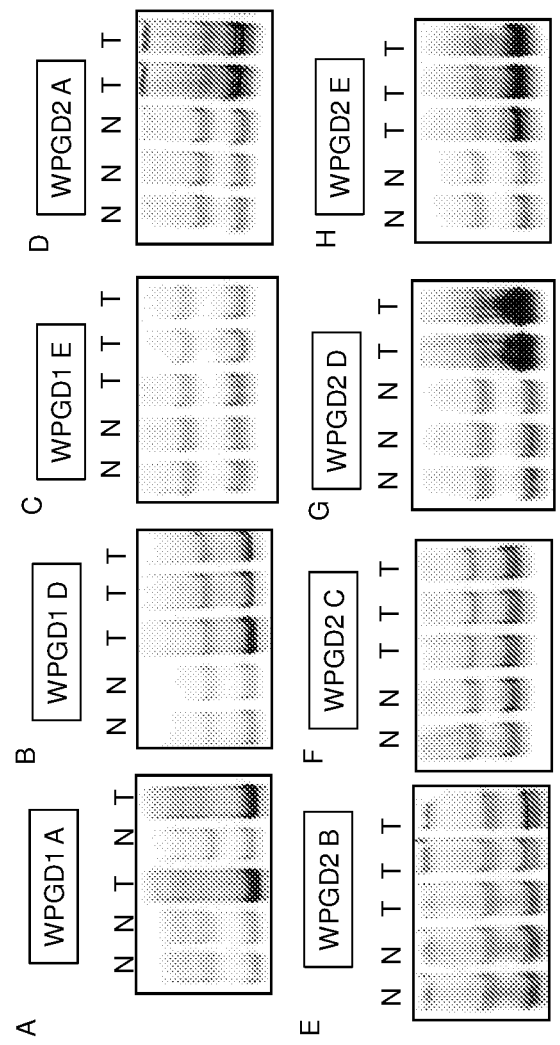
FIG. 23A, FIG. 23B, FIG. 23C, FIG. 23D, FIG. 23E, FIG. 23F, FIG. 23G, and FIG. 23H are images showing that total enzyme activity is enhanced in the presence of the transgene on $T_0$ endosperm according to one embodiment of the present invention.

As shown in FIG. 23 A trough D, 6PGDH enzyme activity was increased when either transgene was present. Qualitative isozyme activity using native PAGE showed increased activity in the faster migrating PGD1/PGD2 band (see FIG. 23B and FIG. 23C).

Heat stability of 6PGDH activity was tested in two independent events for each construct of WPGD1 and WPGD2 as well as two combinations of WPGD1 and WPGD2 events. FIG. 23A, FIG. 23B, FIG. 23C, FIG. 23D, FIG. 24E, and FIG. 24F are a set of gels showing enzyme activity heat stability test according to one embodiment of the present invention. Crude extracts of normal (blue) and transgenic (orange) sibling endosperm tissue were treated at 50° C. in 10-minute intervals according to one embodiment of the present invention. Total 6PGDH activity was measured spectrophotometrically at room temperature. Transgene constructs shown are: WPGD1-C (FIG. 23A), WPGD1-B (FIG. 23B), WPGD2-A (FIG. 23C), WPGD2-B (FIG. 23D), WPGD1-F and WPGD2-E (FIG. 23E), and WPGD1-A and WPGD2-A (FIG. 23F). Error bars indicate ±SD of three biological replicates.

Figure 24:
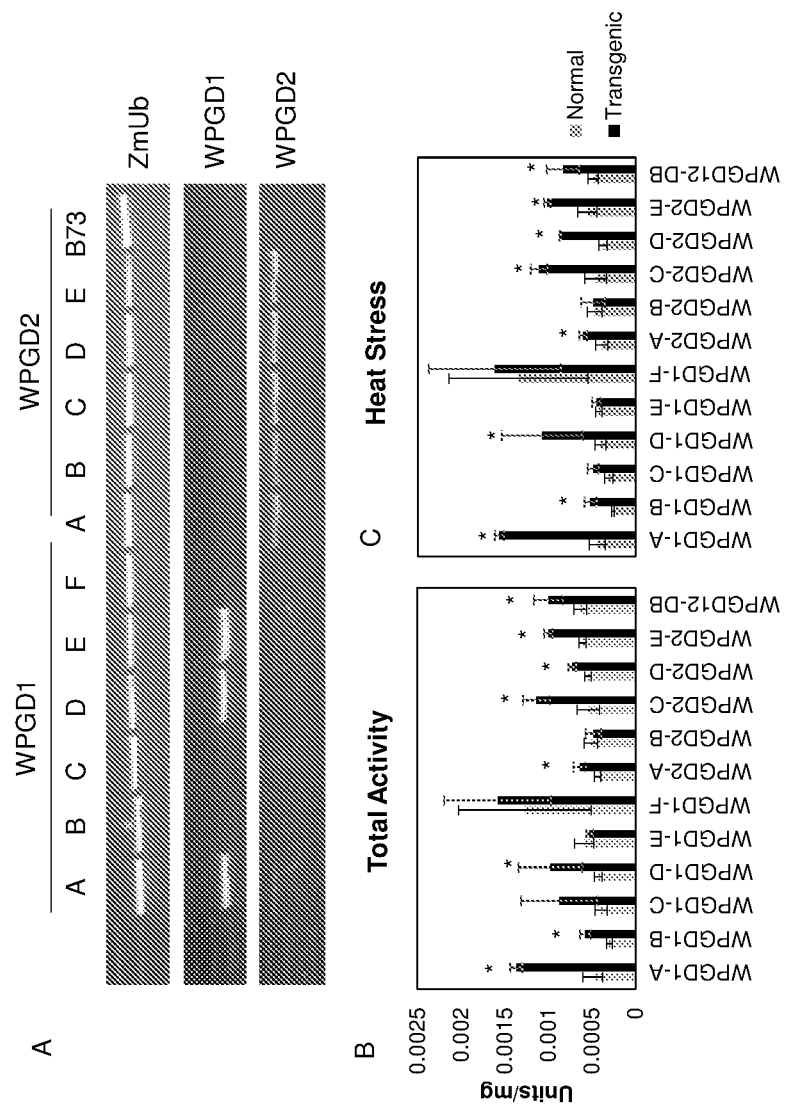
FIG. 24A, is a set of agarose gels showing transgenic gene expression different events obtained post transformation.
FIG. 24B, and FIG. 24C are graphs showing total enzyme activity heat stability test according to one embodiment of the present invention.

As shown in FIG. 24, the presence of one or more transgene loci showed a significant enhancement of enzyme activity heat stability at 50° C. in all genotypes tested. The events that showed best mitigation of heat sensitivity were WPGD1-C (FIG. 24A) and WPGD2-A (FIG. 24C) with near 100% of untreated enzyme activity, while heat-treated normal sibling extractions only had 40%-60% of the activity found in untreated controls. Other events tested such as WPGD1-A (FIG. 24B) had about 10% of mitigation and WPGD2-B had around 20%. Combinations between WPGD1 and WPGD2 also showed enhanced heat stability of 6PGDH activity (FIG. 24E and FIG. 24F). Increased heat stable 6PGDH activity and increased PGD1/PGD2 isozyme activity in the transgenic events indicate that the transgenic lines produce additional PGD1 and PGD2 at higher levels than in non-transgenic controls.

4. Wpgd1 and Wpgd2 Rescue the Endosperm Defective Phenotype of Pgd3

Based on the GND1 protein structure, WPGD1 and WPGD2 pre-proteins should be processed to a mature form to condition higher levels of 6PGDH activity. In addition, in vitro chloroplast import assays indicate that the pre-proteins are targeted to plastids. Most likely, the transgenic WPGD1 and WPGD2 are targeted to the amyloplast. Consequently, the engineered proteins are expected to rescue the defective endosperm phenotype of pgd3 mutants. The single hemizygous transgenics, Wpgd1/− and Wpgd2/−, as well as the double transgenic, Wpgd1/−; Wpgd2/−, were crossed with pgd3/+ plants. The $F_1$ progeny were self-pollinated and F2 kernels are expected to be 25% pgd3 mutant.

Figure 25:
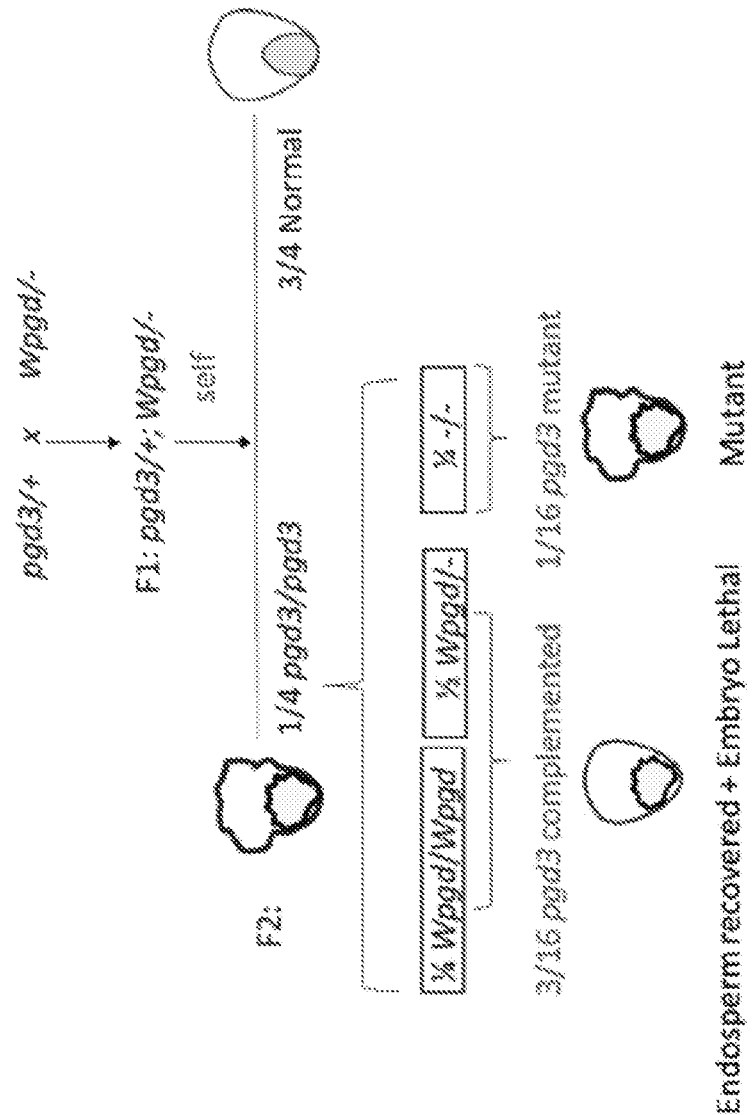
FIG. 25 is a flow diagram showing complementation test crosses and expected phenotypes according to an embodiment of the invention. Heterozygous pgd3/+ plants were crossed with hemizygous Wpgd/− transgenics according to one embodiment of the present invention.

FIG. 25 shows complementation test crosses and expected phenotypes according to one embodiment of the present invention. Heterozygous pgd3/+ plants were crossed with hemizygous Wpgd/− transgenics according to one embodiment of the present invention. The F1 progeny were selfed on the following generation. On the F2 progeny 3/16 were expected to be complemented with an endosperm recovered and embryo lethal phenotype. 1/16 of F2 progeny were expected to remain pgd3/pgd3 mutant. Among the 1/4 pgd3/pgd3 mutants, a single transgene locus is expected to segregate with 1/4 being homozygous, 1/2 being hemizygous, and 1/4 being non-transgenic. Thus, the transgene is expected to rescue 3/16 kernels from the total population, and pgd3 mutant kernels should be reduced to 1/16 of the total kernels.

Although pgd3 has severe endosperm and embryo phenotypes, we only expect the Wpgd1 and Wpgd2 transgenes to rescue the endosperm phenotype. Non-concordant kernels from B-A translocation uncovering crosses of pgd3 mutants indicated that the endosperm and embryo phenotypes are independent. Both Wpgd1 and Wpgd2 are expressed from an endosperm-specific promoter, which would not be expected to rescue the embryo lethal phenotype.

Table 5, below, shows frequencies of reduced grain-fill phenotypes from the self-pollinated progeny of pgd3/+; transgene $F_1$ plants. Control self-pollinations of pgd3/+ plants segregate mutant kernels at 1/4 frequency, while all crosses with Wpgd1 or Wpgd2 transgenes show a significantly reduced frequency of mutant kernels. These data suggest that 3-4% of the kernels are fully rescued homozygous pgd3 mutants.

TABLE 5

Phenotypic classification of self-pollinated progeny from crosses of pgd3 with Wpgd1 or Wpgd2. P-value ($\chi^2$) calculated for 1/4 of expected mutant kernels on the F1 population.

| Genotype | Normal | Mutant | p-value 1/4 Mutant |
|---|---|---|---|
| pgd3/+ | 2095 | 639 | 0.088734 |
| pgd3/WPGD1-E | 1980 | 547 | 0.000747* |
| pgd3/WPGD1-F | 2973 | 863 | <0.00001* |
| pgd3/WPGD2-F | 506 | 119 | 0.002882* |
| pgd3/WPGD2-G | 913 | 216 | 0.00008* |
| pgd3/WPGD1-C/WPGD2-B | 1978 | 378 | <0.00001* |
| pgd3/WPGD1-D/WPGD2-B | 3395 | 818 | <0.00001* |

*indicates significantly different than the expected population value p < 0.05.

Figure 26:
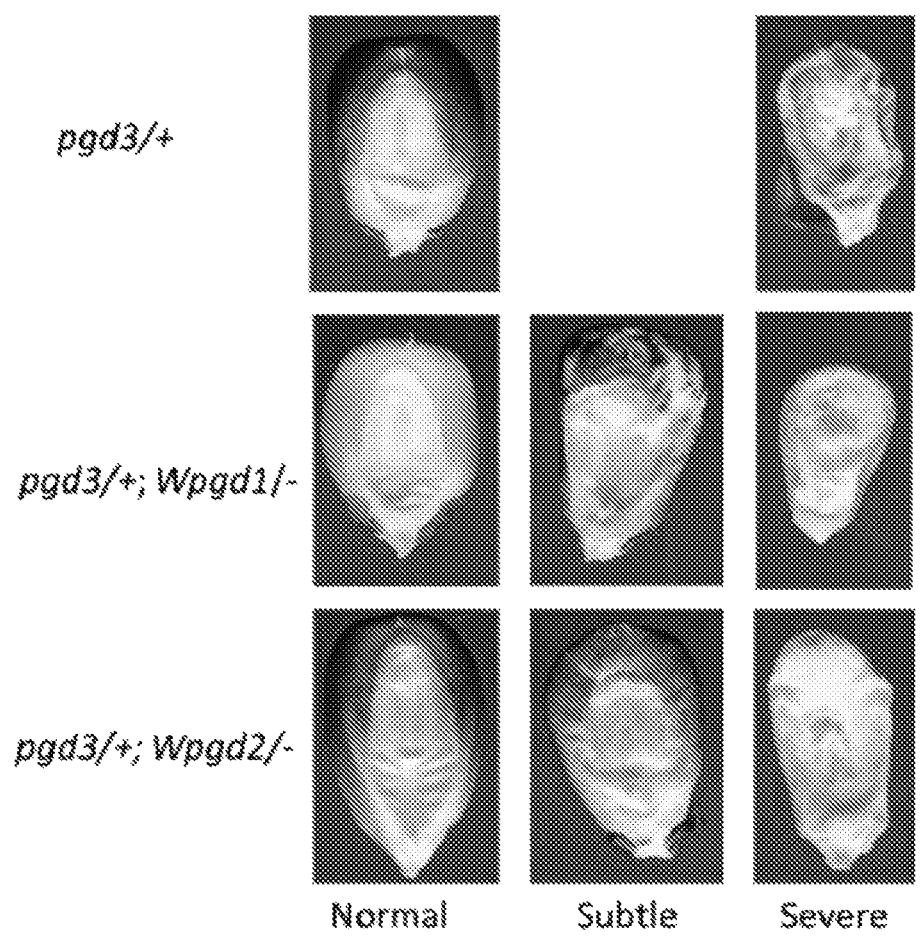
FIG. 26 is a set of images showing populations of crosses between pgd3 and Wpgd transgenics according to one embodiment of the present invention.

The mutant kernels from pgd3/+; transgenic plants had two classes of reduced grain-fill kernels. There were severe mutants similar to control pgd3/pgd3 kernels as well as subtle mutants with intermediate grain-fill (FIG. 26). FIG. 26 is a set of images showing populations of crosses between pgd3 and Wpgd transgenics according to one embodiment of the present invention. Kernels were divided into normal and two classes of mutant. Subtle mutants had more grain-fill and embryo development than severe mutants that were identical to standard pgd3 mutants. The subtle mutants likely represent the rescued endosperm phenotype.

However, this phenotype does not fit the expected complemented pgd3 kernel class as there are fewer subtle kernels than expected for a 3/16 ratio (Table 6). There also were more than 1/16 severe mutant kernels in most of the $F_1$ progeny from these crosses. For the data presented in Table 6, P-value ($\chi^2$) was calculated for subtle phenotype observed ratios to 3/16 of expected complemented kernels. P-value ($\chi^2$) calculated for severe phenotype observed ration to 1/16 expected mutant kernels on the F1 population.

TABLE 6

Phenotypic designation and P-value ratio from the subtle and severe looking kernels

| F1 Genotype | Total | Normal | Mutant | Fraction Mutant | p($\chi^2$) 1/4 Mutant |
|---|---|---|---|---|---|
| pgd3/+ | 2734 | 2095 | 639 | 0.233 | 0.0887 |
| pgd3/+; Wpdg1-E/− | 2527 | 1980 | 547 | 0.216 | 0.0007* |
| pgd3/+; Wpdg1-F/− | 3836 | 2973 | 863 | 0.224 | <0.0000* |
| pgd3/+; Wpdg2-F/− | 625 | 506 | 119 | 0.190 | 0.0028 |
| pgd3/+; Wpdg2-G/− | 1129 | 913 | 216 | 0.191 | 0.0000* |
| pgd3/+; Wpdg1-C/−; Wpdg2-B/− | 2356 | 1978 | 378 | 0.160 | <0.000* |
| pgd3/+; Wpdg1-d/−; Wpdg2-B/− | 4213 | 3395 | 818 | 0.194 | <0.000* |

*indicates significantly different than the expected population value p < 0.05.

The statistics in Table 6 indicate that there are fully rescued kernels with a normal kernel phenotype. All mutant kernels along with 48 normal kernels are weighted and genotyped individually for both the pgd3 locus and the presence of the transgene. This identified pgd3/pgd3 mutants with at least one copy of the Wpgd transgene in the normal kernels.

Whether the subtle mutant seeds produced viable pgd3 mutant embryos was tested using germination tests (Table 7). As shown in the table, the pgd3 mutant cannot be germinated as a seed; it can only be in vitro embryo rescued with <5% of pgd3 embryos able to develop as a seedling. By contrast, pgd3 mutants with the transgene germinate. The Wpgd1 events tested had 20 to 30% of the rescued kernels germinate, and a higher rate was observed for pgd3; Wpgd2 kernels with 50 to 70% germination.

TABLE 7

Germination rate of mature pgd3 kernels.

| Genotype | Average of Germination (%) from 20 Seeds Planted |
|---|---|
| pgd3/pgd3 | 0 |
| pgd3/+; Wpgd1-E/− | 19 |
| pgd3/+; Wpgd1-F/− | 33 |
| pgd3/+; Wpgd2-F/− | 50 |
| pgd3/+; Wpgd2-G/− | 71 |

Figure 27:
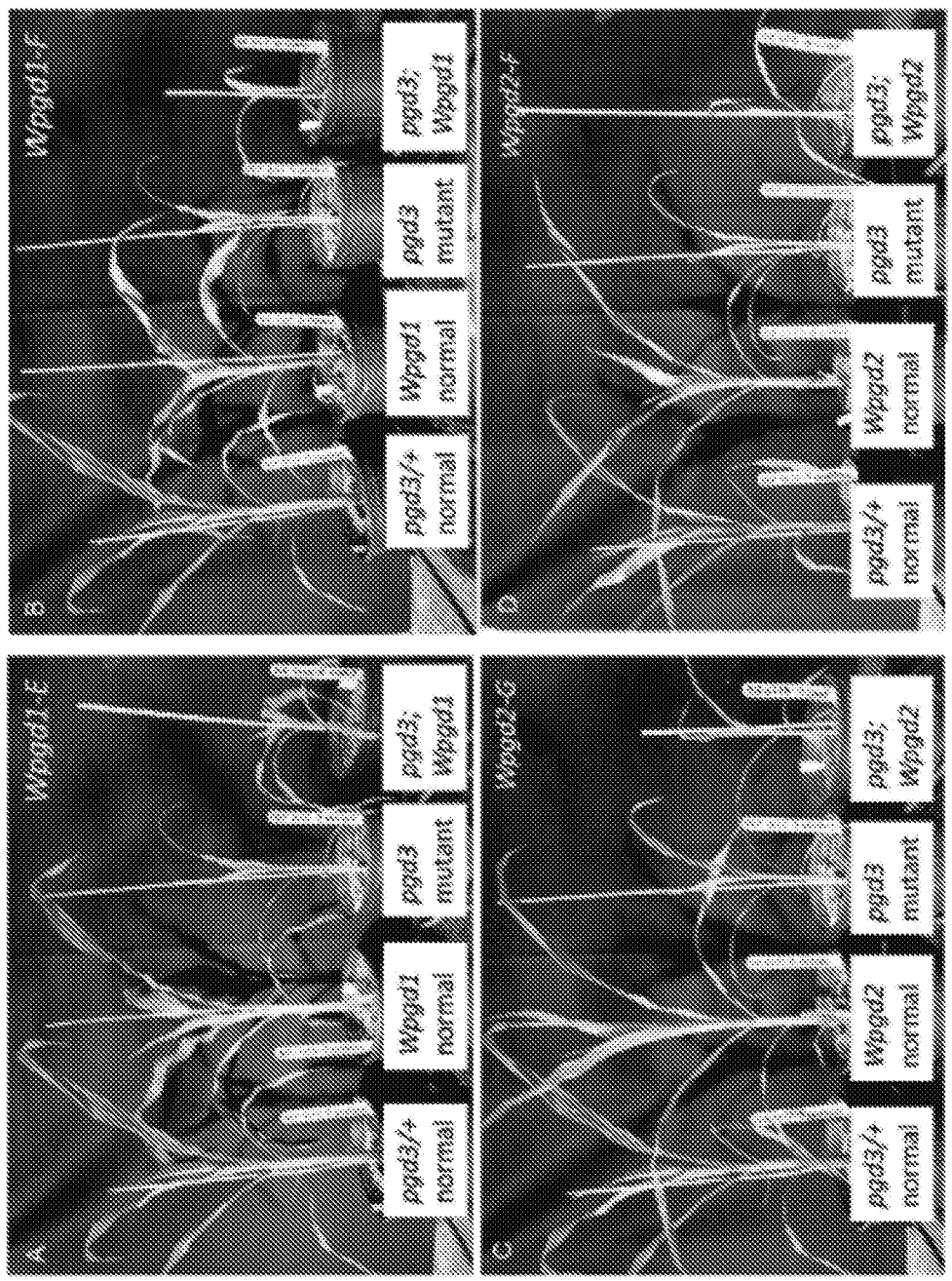
FIG. 27A, FIG. 27B, FIG. 27C, and FIG. 27D are images showing seedlings phenotypes at 35 days after germination (DAG) according to one embodiment of the present invention.

As shown in FIG. 27, plant development was compared between embryo rescued pgd3/pgd3 versus pgd3/pgd3; Wpgd1/− and pgd3/pgd3; Wpgd2/− transgenic plants. Heterozygous pgd3, Wpgd1, and Wpgd2 transgenic siblings were grown as normal controls. All three classes of homozygous pgd3 plants: pgd3/pgd3, pgd3/pgd3; Wpgd1/– and pgd3/pgd3; Wpgd2/–, show very similar phenotypes throughout development. At 35 DAG, the mutants grow slower, stunted, and are slow to green in comparison with normal plants. FIG. 27A, FIG. 27B, FIG. 27C, and FIG. 27D are images showing seedlings phenotypes at 35 DAG according to one embodiment of the present invention. Comparing normal looking plants pgd3/+ and transgenic normal with Mutant looking phenotypes of pgd3/pgd3 and pgd3/pgd3; Wpgd/–. A) Wpgd1-E, B) Wpgd1-F, C) Wpgd2-G and D) Wpgd2-F.

Figure 28:
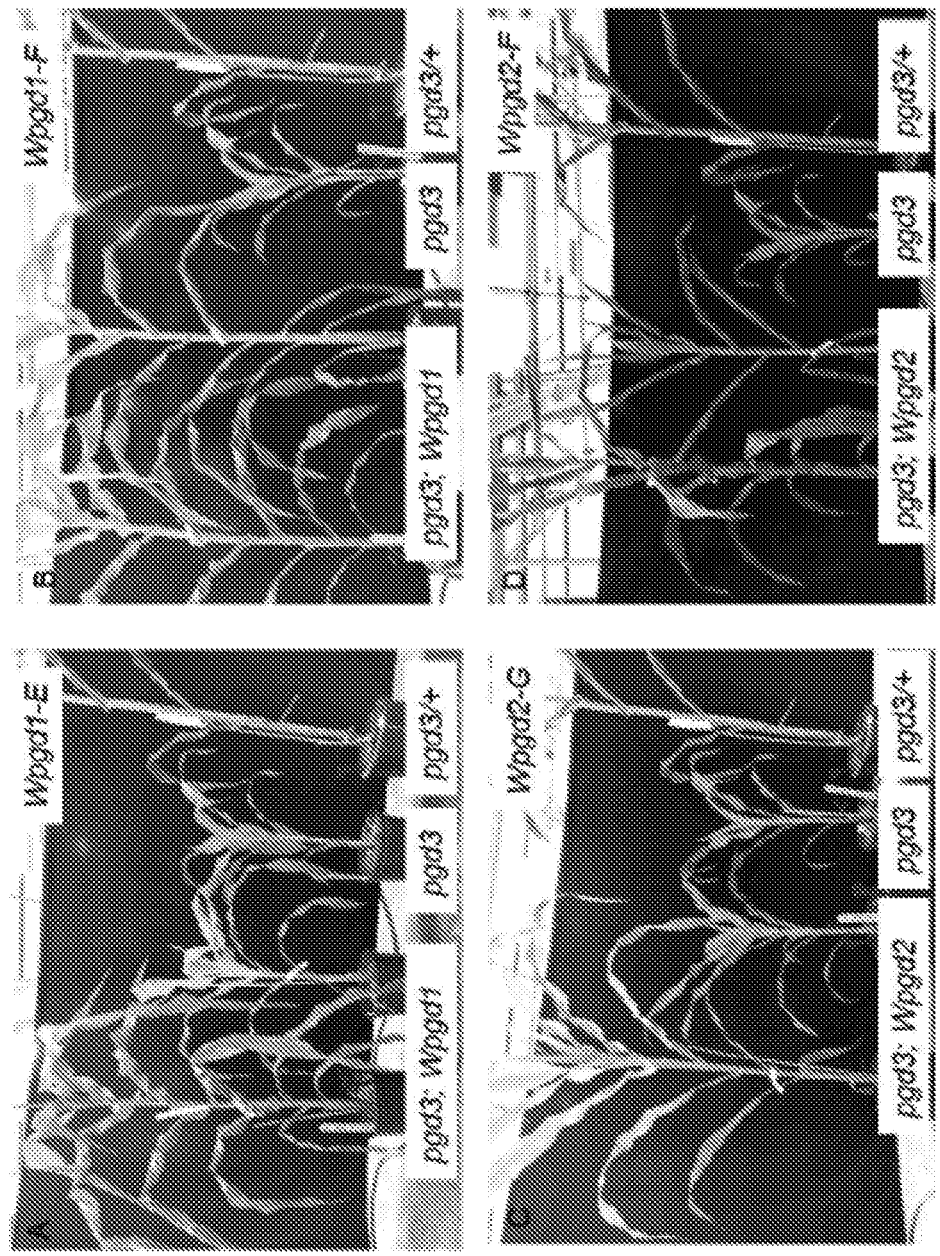
FIG. 28A, FIG. 28B, FIG. 28C, and FIG. 28D are images illustrating plant phenotypes at 85 DAG according to one embodiment of the present invention.

FIG. 28A, FIG. 28B, FIG. 28C, and FIG. 28D are images illustrating plant phenotypes at 85 DAG according to one embodiment of the present invention. Comparing normal looking plants pgd3/+ with phenotypes of pgd3/pgd3 and pgd3/pgd3; Wpgd/. FIG. 28A: Wpgd1-E; FIG. 28B: Wpgd1-F; FIG. 28C: Wpgd2-G; and FIG. 28D: Wpgd2-F. As shown in FIG. 28, at 85 DAG, the plant phenotype of pgd3/pgd3; Wpgd1/– and pgd3/pgd3; Wpgd2/– were still stunted in comparison with normal plants. However, transgenic rescued plants can be taller than tissue culture rescued pgd3/pgd3 plants. This may be related to an early growth advantage with a larger endosperm and more developed embryo in the transgenic kernels compared to pgd3 mutants rescued in tissue culture.

FIG. 29A, FIG. 29B, FIG. 29C, FIG. 29D, FIG. 29E, and FIG. 29F are images illustrating self-pollinated ears showing transgenic rescue of the pgd3 mutant according to one embodiment of the present invention. Comparisons of ears phenotypes between FIG. 29A: pgd3/pgd3; FIG. 29B: pgd3/+; FIG. 29C: pgd3/pgd3, Wpgd1-E/Wpgd1-E; FIG. 29D: pgd3/pgd3; Wpgd1-E/–; FIG. 29E: pgd3/pgd3, Wpgd2-G/Wpgd2-G; FIG. 29F: pgd3/pgd3; Wpgd2-G/– are shown. Self-pollinations of embryo rescued pgd3/pgd3 are fertile and develop all homozygous mutants with the severe pgd3 grain-fill phenotype (see FIG. 29A). By contrast, self-pollination of either pgd3/pgd3; Wpgd1/– or pgd3/pgd3; Wpgd2/– plants develop kernels with mostly normal grain-fill (see FIG. 29C. FIG. 29D, FIG. 29E, and FIG. 29F).

FIG. 30A, FIG. 30B, FIG. 30C, FIG. 30D, FIG. 30E, FIG. 30F, FIG. 30G, and FIG. 30H illustrate genotyping of pgd3/pgd3; Wpgd2 ears from the same event and population according to one embodiment of the present invention (FIG. 30A: Ear pgd3/pgd3; Wpgd2-F/Wpgd2-F with full kernel phenotype rescue; FIG. 30B: Genotyping gel with the WPGD2L and NosTR markers to determine the presence of the transgene; FIG. 30C: Genotyping gel with the flanking co-dominant markers PGD3L, PGD3R and Tir5 to determine the presence of the Mu transposon insertion in the pgd3/pgd3 mutant; FIG. 30D: Ear pgd3/pgd3; Wpgd2-F/– with segregation of kernel phenotype; FIG. 30E: Mutant kernels genotyping gel with the WPGD2L and NosTR markers; FIG. 30F: Mutant kernels genotyping gel with the flanking co-dominant markers PGD3L, PGD3R and Tir5; FIG. 30G: Normal kernels genotyping gel with the WPGD2L and NosTR markers; FIG. 30H: Normal kernels genotyping gel with the flanking co-dominant markers PGD3L, PGD3R and Tir5).

Figure 30:
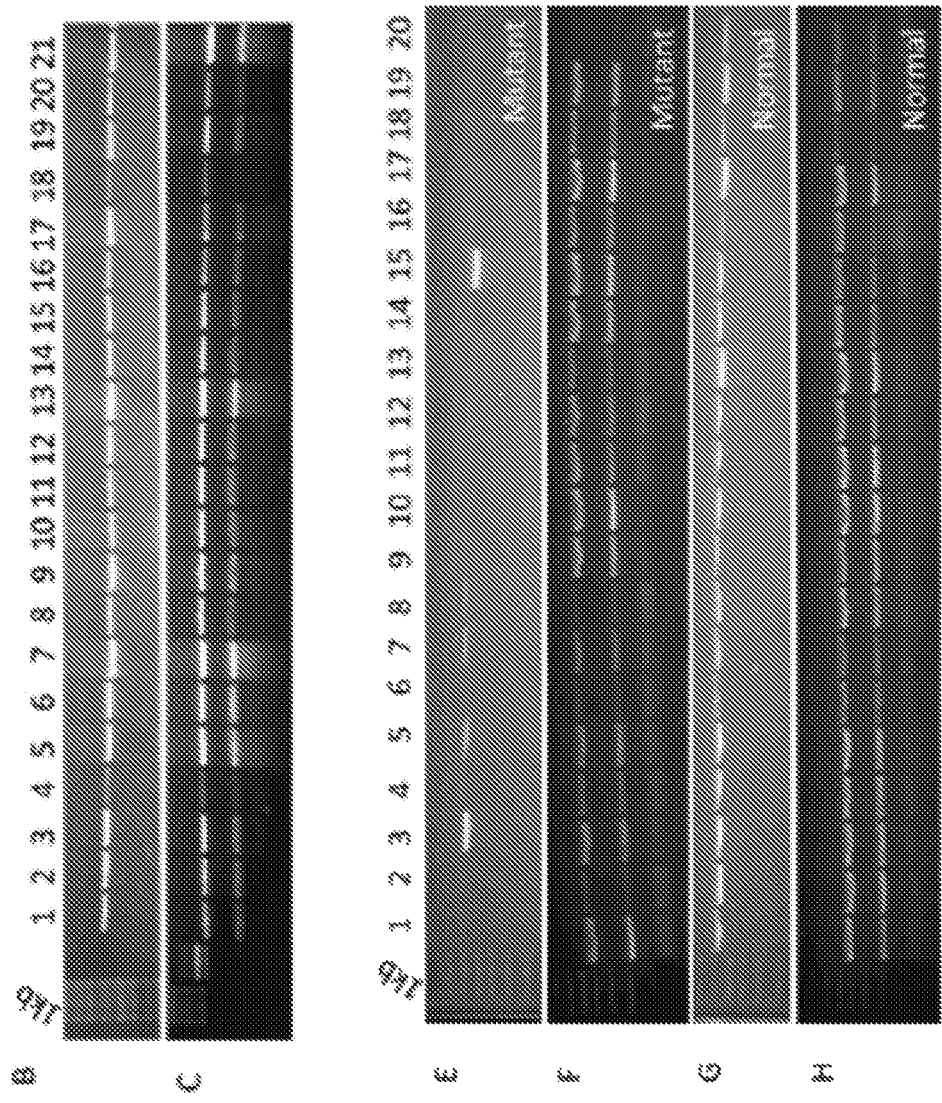
FIG. 30A, FIG. 30B, FIG. 30C, FIG. 30D, FIG. 30E, FIG. 30F, FIG. 30G, and FIG. 30H illustrate genotyping of pgd3/pgd3; Wpgd2 ears from the same event and population according to one embodiment of the present invention.

As shown in FIG. 30, co-segregation analysis was completed for one pgd3/pgd3; Wpgd2/Wpgd2 homozygous ear that showed all normal kernels and one pgd3/pgd3; Wpgd2/– heterozygous ear that segregated for severe defective kernels. Using a co-dominant marker for pgd3, both ears showed all homozygous mutant genotypes. In FIG. 30A, all kernels appear normal, and all kernels tested also contain the transgene (see FIG. 30B and FIG. 30C). In FIG. 30D, there is segregation for a mutant phenotype, and 20 mutants (see FIG. 30E and FIG. 30F) and 20 normal (see FIG. 30G and FIG. 30H) kernels are genotyped. Only two of the mutant looking kernels amplified the transgene above maternal DNA contamination levels, while all 20 normal kernels contained the transgene. These results suggest that a homozygous transgene locus can completely complement the pgd3 kernel phenotype.

C. Conclusions

In this example, successful genetic engineering to deliver heat stable 6PGDH enzyme activity to the amyloplast during endosperm development is demonstrated. A translational fusion of the WX1 chloroplast transit peptide with each of the heat-stable, cytosolic isozymes, was able to be imported into isolated pea chloroplasts and processed indicating that the targeting sequence is functional. Transgenic maize plants were generated to express Wpgd1 and Wpgd2 from the 27 kDa γ-zein promoter to confer endosperm specific expression. The transformants have increased 6PGDH enzyme activity in the endosperm and isozyme activity assays suggest the increase is due to higher levels of PGD1 and PGD2. Transgenic endosperm also shows enhanced heat stability in vitro. Finally, the Wpgd1 and Wpgd2 transgenes rescue the pgd3 defective kernel phenotype indicating that the fusion proteins are targeted to the amyloplast and fold into active enzymes.

Figure 29:
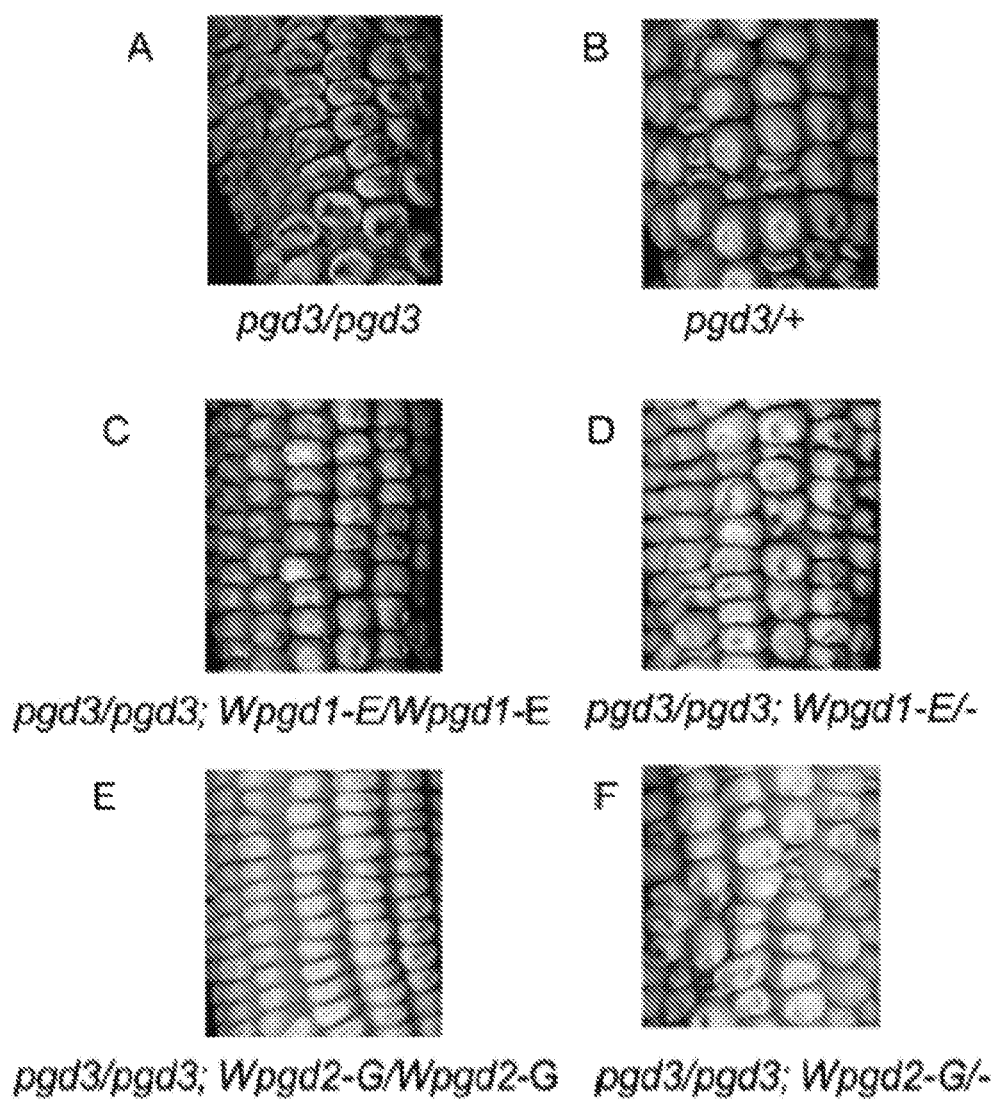
FIG. 29A, FIG. 29B, FIG. 29C, FIG. 29D, FIG. 29E, and FIG. 29F are images illustrating self-pollinated ears showing transgenic rescue by Wpgd1 and Wpgd2 of the pgd3 mutant according to one embodiment of the present invention.

The Wpgd1 and Wpgd2 transgenes also appear to rescue the embryo development defects of pgd3. Prior analysis of genetically non-concordant kernels generated with B-A translocation crosses showed that complementation of the pgd3 endosperm does not improve pgd3 mutant embryo development. We predicted that the Wpgd1 and Wpgd2 transgenes would only rescue the endosperm phenotype, but as FIG. 29 shows, pgd3/pgd3; Wpgd2/Wpgd2 plants can develop all normal progeny when self-pollinated. These data argue strongly for the endosperm expression of PGD3 being essential for both endosperm and embryo development.

However, most of the transgenic rescued kernels only showed partial rescue with an intermediate kernel weight at maturity. Potentially, the partial endosperm rescue might be related to the endosperm-specific promoter. The 27-kDa γ-zein has strong endosperm expression during grain filling stages from 10 to 25 DAP. Native PGD3 isozyme activity is associated with all sink tissues. It is possible that the transgenic promoter is not active enough early in seed development to supply sufficient plastidic 6PGDH to fully complement pgd3 mutants. Alternatively, the full rescue of the pgd3 kernel may be event-specific, and all transgenic events would need to be crossed to pgd3 to identify the most robust events for heat stress mitigation. Regardless, the data show that heat stable isoforms have been successfully engineered in the amyloplast and can be tested for mitigation of heat-induced yield losses.

Example 3. The Amyloplastic Engineered Version of 6PGDH can Maintain Grain Yield Under Heat Stresses A. Materials and Methods 1. General Comments Climate change caused by the rise of atmospheric $CO_2$ concentration threatens future food production due to the direct effects of changes in environmental conditions. The expected environmental changes will increase the frequency of extreme weather episodes leading to heat stress and drought. In addition, reduced winter freezing events are projected to enhance pest damage to crops. Many climate scientists believe if major action is not undertaken very soon a number of consequences will become irreversible. Impacts that have already occurred and risks for future impact has been detailed by the Intergovernmental Panel on Climate Change (IPCC), including melting of snow and ice that are altering heat-loading of the hydrological systems, species migrations from their original geographic locations, and crop yield losses (IPCC, 2014).

The United States Environmental Protection Agency has affirmed that since 1901 the average temperature across the United States has increased at an average rate of 0.077° C. per decade. However, since 1979 the rate of temperature rise has increased dramatically from 0.16 to 0.25° C. per decade. Eight of the ten warmest years registered happened from 1998 with 2012; 2015 was the warmest years ever recorded (NOAA, 2016). The projected average US temperature in 2100 is anticipated to increase by a range of 1.66 to 6.66° C., depending on atmospheric carbon levels.

Temperature is a critical factor affecting plant development and crop yield. Vegetative production (node and leaf emergence rate) generally increases as temperatures approach an optimum level. However, it is important to highlight that heat stress affects each developmental stage in different ways. In most plant species, vegetative growth usually has a higher optimum temperature than for reproductive development. A faster development of non-perennial crops will result in a shorter life cycle, causing stunted growth, shorter reproductive duration, and lower yield potential. During the maize vegetative stage, the highest temperature on a non-stressed condition is of 37° C., and lowest temperature is 8° C. with ideal being 34° C. Whereas in the reproductive stage, the minimum temperature remains 8° C., but the optimal temperature decreases to 22° C.

Pollen viability in maize has been shown to decrease at temperatures above 35° C. This temperature effect is increased under vapor pressure deficits. Pollen viability is strongly dependent on pollen moisture with reduced viability affecting final seed set. During kernel development, a brief exposure of plants to 35° C. temperatures just after pollination reduced kernel growth rate along with final kernel size, even after plants were returned to 30° C. Exposure to temperatures above 30° C. inhibited cell division and amyloplast replication in maize kernels, which reduced the size of the grain and ultimately yield.

Heat stress during early grain formation stage from 1-15 DAP affected the physicochemical properties of waxy starch, by decreasing the swelling power, enhancing the gelatinization temperature and retrogradation percentage. Field grown maize composition was also shown to be affected by heat stresses during grain filling with impacts on protein content and starch. Finally, there are negative correlations of higher temperature and drought to final yield. Interestingly, yield was shown to be more responsive to each 2° C. increase above 30° C. compared to each decrease of 20% of seasonal rainfall.

In Florida and Georgia, planting date can be critical for final grain yield. Planting in Mid-February and March was shown to yield more than planting in early April through mid-May. Decreases in later plantings were as large as 50% of early plantings correlating higher temperatures with reduced yield.

High night temperatures, can cause wasteful respiration and was reported to decrease final biomass in rice, wheat and corn. Respiration rate increases with temperature. Therefore, sugars produced during the day are consumed at a greater rate. Consequently, high night temperatures will decrease available nutrients for developing kernels causing reduced grain fill. Thus, high temperatures have combined effects on the plant and kernel. Earlier plant maturation gives less time to accumulate biomass. High night temperatures also reduce seed set and grain-fill.

Controlled temperature experiments more specifically address how the grain filling stage is affected by heat stresses. High temperature treatments from 18 DAP to maturity of 35° C. during the day and 25° C. at night caused decreases of up to 45% on seed weight in maize. Later, another experiment applied treatments from 15 DAP with a day/night cycle of 33.5/25° C. in comparison to a control of 25/20° C., in which heat treated samples showed a decrease of 7% on kernel dry weight. Recently, in a growth chamber controlled environment experiment, such as discussed in Example 1, above, with three environmental conditions normal day/normal night (28/17° C.), hot day/normal night. (38/17° C.), and hot day/hot night (38/28° C.), from 12 DAP until maturity, mature kernel weight analysis showed that kernel weight was reduced by 22% in the hot day/hot night condition. These experiments illustrate the importance of night temperatures on total seed weight.

The process of breeding, delivery, and adoption of a new maize line can take up to 30 years. Yield losses due to increased temperatures could be avoided by generating lines that mitigate the effects of high temperature stress and incorporating these adapted traits throughout the breeding cycle. Traditional plant breeding has made important achievements in developing heat-adapted varieties by germplasm selection. Breeding thermotolerant lines can be a difficult goal to achieve, as heat sensitivity is volatile throughout developmental stages. When heat stressed, plants activate response that switch the activities of thousands of many genes and proteins.

Usually breeding selections are carried out in hot regions and thermotolerance traits would be selected by through local adaptation. Some examples on enhanced heat tolerance attained by recurrent selections were reported in wheat and potato. In maize, there is potential to use the diversity of available germplasm for recurrent selection. Even though traditional plant breeding has made advances in developing heat-tolerant lines and has the potential to generate new heat resistant lines, there is still much to unravel about the genetic basis of heat tolerance in plants.

Molecular breeding is an approach that uses the understanding of genetics as well as transcriptional and biochemical networks that influence traits to make selections that positively impact crop performance, for example, engineering a heat-stable version of the cereal AGPase enhances grain yield under heat stress in multiple cereal crops. Similarly, expression of a gene encoding a rice threhalose-6-phosphate in developing maize ears enhances yield under non-drought, mild and severe drought conditions. Molecular breeding requires a detailed understanding of the gene and biochemical system that impacts a trait. However, it is an attractive alternative to traditional breeding approaches to generate heat-stable germplasm without requiring extensive selection for local adaptation.

This example describes an engineered 6PGDH amyloplastic transgene and its ability to maintain grain fill under high temperatures. 6PGDH is an enzyme that is critical for starch accumulation during grain filling stages in maize as shown in Example 1. Introducing a heat-stable cytosolic 6PGDH enzyme activity to the amyloplasts would help to mitigate grain yield loss by stabilizing kernel starch accumulation under high temperatures. This tool can be utilized in elite maize lines to counterbalance against yield loss in the face of increasing global temperatures.

A. Materials and Methods

Florida provides a unique environment to field test heat stress effects on corn. Summer temperatures expose corn to heat stress that cause severe yield reductions. However, early season plantings can complete a life cycle with relatively little heat stress. We took advantage of these differences in temperature to compare yield in four transgenic events of Wpgd1 and four events of Wpgd2 genetically modified (GM) corn. Early planting was Mar. 15, 2017 and a heat stress planting was on Apr. 12, 2017. Each planting had a randomized complete block design with three replicates of transgenic and isogenic non-transgenic siblings (normal) from segregating ears. Transgenics and normal siblings were planted in separate blocks to minimize cross-pollination of the transgene.

B. Experimental Results

Figure 31:
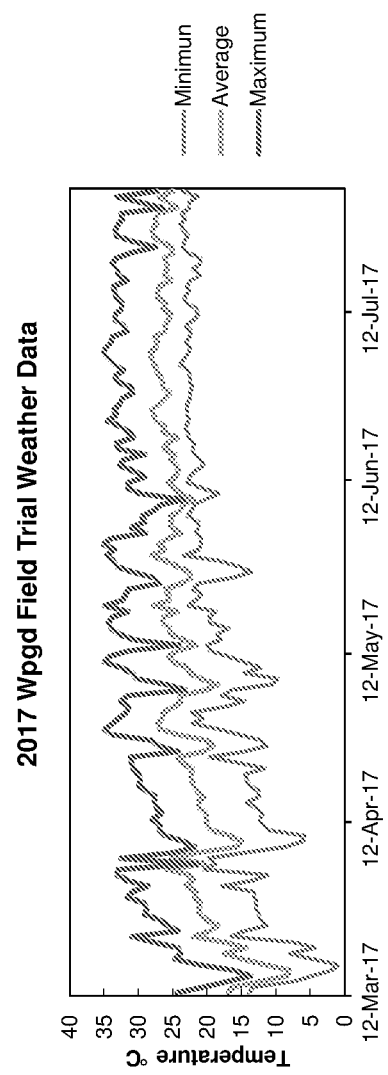
FIG. 31 is a plot illustrating air temperature readings plotted for at 15-minute intervals according to one embodiment of the present invention. The 30 DAP grain-fill periods are indicated by blue (Planting 1) and orange (Planting 2) lines. Critical temperatures for corn growth and development are based on the scientific literature with temperatures above 29° C. considered heat stress (red line), 25° C. considered optimal (black line), and temperatures below 10° C. considered cold stress (light blue line).
Figure 32:
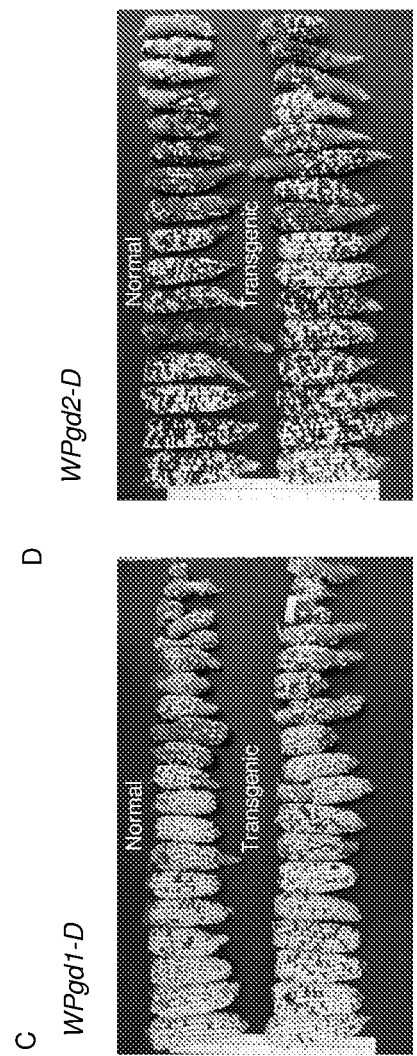
FIG. 32A, FIG. 32B, FIG. 32C, and FIG. 32D are images illustrating population phenotypic comparisons according to one embodiment of the present invention.

FIG. 31 shows the 60 cm air temperature at the field site throughout the trial. Each data point is a temperature reading in 15 minute intervals. According to Schlenker and Roberts (2009), plants would be considered exposed to heat stress when temperatures are above 29° C. (red line) and to cold stress when below 10° C. (blue line). The bulk of grain-fill occurs through 30 days after pollination (DAP). By 30 DAP, the late planting experienced 5.8 days more cumulative exposure to temperatures above 29° C. compared to the 30 DAP time point in the early planting.

The 30 DAP grain-fill periods are indicated by blue (Planting 1) and orange (Planting 2) lines. Critical temperatures for corn growth and development are based on the scientific literature with temperatures above 29° C. considered heat stress (red line), 25° C. considered optimal (gray line), and temperatures below 10° C. considered cold stress (blue line).

FIG. 32A, FIG. 32B, FIG. 32C and FIG. 32D are photographs of corn ears illustrating population phenotypic comparisons according to one embodiment of the present invention. Early (planting 1), and Late (planting 4) for Wpgd1-C, and Wpgd2-B. FIG. 32 compares plantings 3 and 4. While the temperatures were not drastically different between the early and late plantings, there was a visible reduction in ear size and seed set in the later plantings. These results suggest that the moderately higher temperatures in planting 4 induced a heat stress on the plants.

Figure 33:
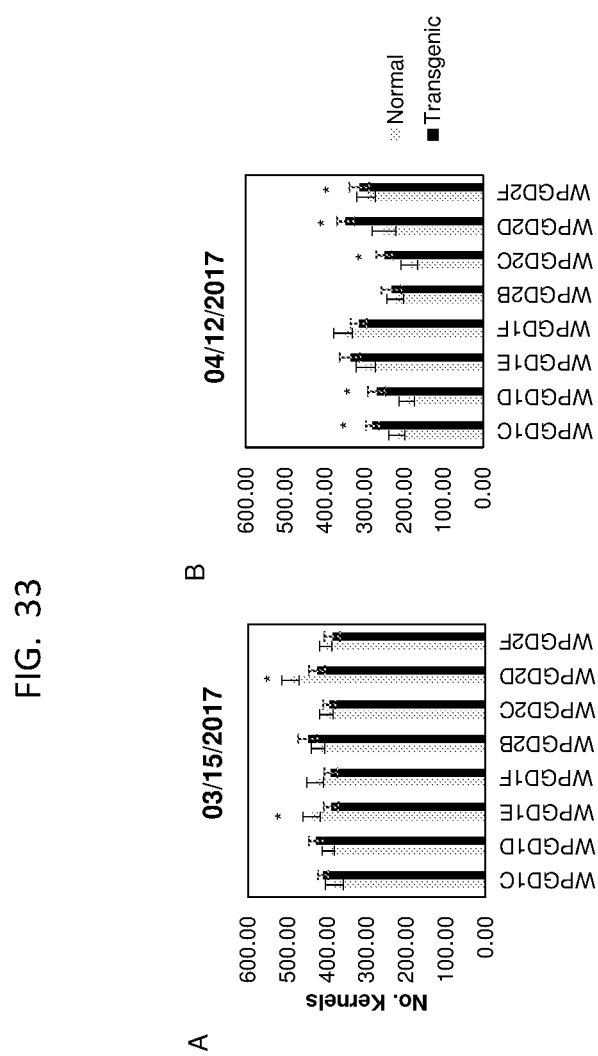
FIG. 33A and FIG. 33B are graphs showing kernel number averages comparisons between normal (grey) and transgenic (black) ears planted on 15 Mar. 2017 and 12 Apr. 2017.

FIG. 33A and FIG. 33B are graphs illustrating the number of kernels yield from 2017 Wpgd field trial according to one embodiment of the present invention. From all the attributes analyzed kernel number was in which most yield enhancements was observed. Five events had significant increased kernel number under height temperatures in the transgenic line in comparison to normal siblings, no negative decreases were observed in the transgenic lines under high temperatures FIG. 33B. Bar charts plot mean and standard error, a T-test paired one-tailed distribution was performed to determine statistical significance.

Figure 34:
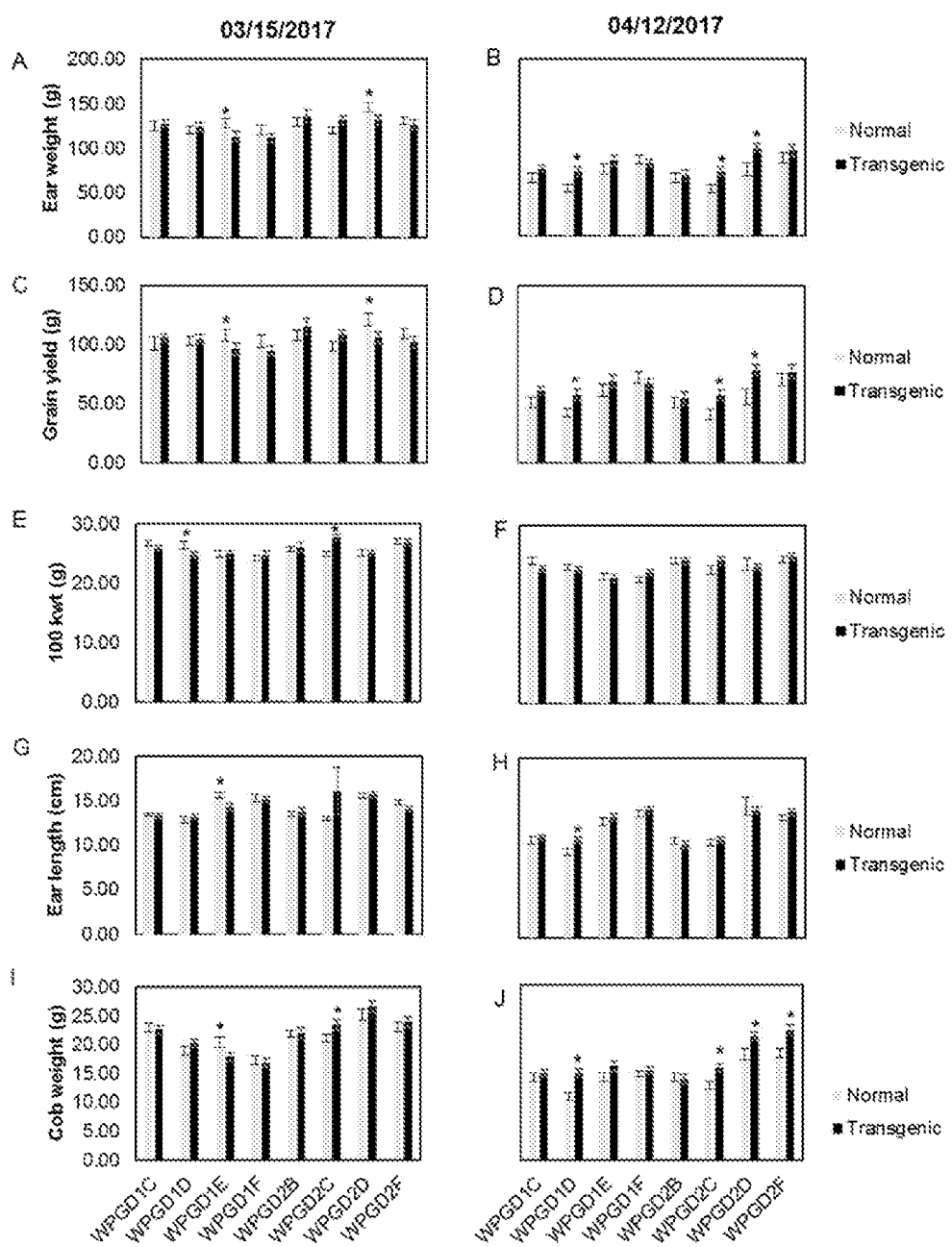
FIG. 34 shows comparisons between averages from normal (grey) and transgenics (black) from early planting 15 Mar. 2017 and late planting 12 Apr. 2017.

As shown in FIG. 34A and FIG. 34B, average ear weights of non-GMO genotypes were 133 g in the March 15 planting and 80 g in the April 12 planting. This is a 40% reduction of yield in the late planting, which is consistent with a threshold effect of high temperature on corn yields. There was no statistical difference in normal and transgenic ear weights from the early season planting with average transgenic ear weight of 130 g (FIG. 34A). These data suggest that the Wpgd1 and Wpgd2 have no negative effect on corn production in more ideal temperature conditions. Similar results were observed in grain yield, by dividing the total ear weight by the cob weight FIGS. 34C and 34D.

Under heat stress conditions, transgenic plants produced much heavier ears in the late season with an average 18% increase in ear weight relative normal siblings (FIG. 34B). Transgene events are known to vary in expression and events Wpgd1-F and Wpgd2-B had little to no difference between transgene and normal sibling yield. It is typical for seed companies to screen >50 events per transgene to identify the best insertion sites for commercialization.

In addition, potential genetic background effects were noticed. Seed sources for three of the transgenic events derived from segregating F2 populations from crosses of the Hill $T_1$ plant by the W22 inbred line. These F2 plants are segregating for three haplotypes throughout the genome and variation in levels of heterozygosity between siblings is likely to mask the specific effect of the transgenes. By contrast 4 out of 5 transgenic events deriving from self-pollinations of backcross generation 1 (BC1S1) individuals showed strong yield gains from 16-35% above normal siblings. In other attributes analyzed, such as, 100 kernels weight FIG. 34E and FIG. 34F, and ear length FIG. 34G there were no significant differences observed between transgenics and normal under the conditions observed. In cob weight FIG. 34I and FIG. 34J, there were significant increases on four transgenic events, under high temperatures, with no negative effects under those conditions. The events that showed yield maintenance in four of the attributes evaluated (kernel number, grain yield, ear weight and cob weight) were Wpgd1-E, Wpgd2C and WPGD2 E with about 40% increased yield.

TABLE 8

Final Field Trial Statistics.

TABLE 8 - PART I

Mar. 15, 2017

| Event pValue (T-Test) | Normal Ear length (cm) | GMO Ear length (cm) | Normal Ear weight (g) | GMO Ear weight (g) | Normal Grain yield (g) | GMO Grain yield (g) | Normal Cob weight (g) | GMO Cob weight (g) |
|---|---|---|---|---|---|---|---|---|
| WPGD1C | | 0.480 | | 0.191 | | 0.189 | | 0.291 |
| Average | 13.465 | 13.285 | 124.712 | 127.895 | 101.013 | 105.739 | 23.050 | 22.599 |
| Stdev | 0.821 | 1.590 | 24.109 | 27.031 | 26.109 | 23.673 | 3.433 | 5.390 |
| StdError | 0.171 | 0.232 | 5.027 | 3.943 | 5.444 | 3.453 | 0.716 | 0.786 |
| WPGD1D | | 0.268 | | 0.359 | | 0.496 | | 0.152 |
| Average | 12.810 | 13.126 | 120.508 | 123.919 | 103.331 | 104.256 | 18.907 | 20.215 |
| Stdev | 2.613 | 1.858 | 28.368 | 31.896 | 26.409 | 28.892 | 5.208 | 5.080 |
| StdError | 0.381 | 0.258 | 4.138 | 4.423 | 3.852 | 4.007 | 0.760 | 0.704 |
| WPGD1E | 0.002* | | | 0.008* | | 0.021* | | 0.019* |

TABLE 8-continued

Final Field Trial Statistics.

| | | | | | | | | |
|---|---|---|---|---|---|---|---|---|
| Average | 15.622 | 14.275 | 128.503 | 113.244 | 107.816 | 96.174 | 20.387 | 17.898 |
| Stdev | 2.284 | 2.845 | 35.799 | 41.361 | 34.085 | 37.964 | 6.028 | 5.354 |
| StdError | 0.340 | 0.380 | 5.337 | 5.527 | 5.081 | 5.073 | 0.899 | 0.715 |
| WPGD1F | | 0.422 | | 0.113 | | 0.136 | | 0.364 |
| Average | 15.296 | 15.124 | 120.525 | 111.211 | 102.831 | 95.030 | 17.290 | 16.772 |
| Stdev | 2.851 | 2.647 | 40.278 | 33.185 | 37.511 | 29.875 | 5.043 | 5.801 |
| StdError | 0.384 | 0.351 | 5.431 | 4.395 | 5.058 | 3.957 | 0.680 | 0.768 |
| WPGD2B | | 0.305 | | 0.302 | | 0.261 | | 0.467 |
| Average | 13.491 | 13.761 | 129.600 | 136.114 | 107.523 | 114.834 | 21.874 | 22.026 |
| Stdev | 1.875 | 2.592 | 29.456 | 41.882 | 28.301 | 38.073 | 3.496 | 5.809 |
| StdError | 0.276 | 0.458 | 4.343 | 7.404 | 4.173 | 6.730 | 0.515 | 1.027 |
| WPGD2C | | 0.119 | | 0.071 | | 0.099 | *0.022 | |
| Average | 12.942 | 16.083 | 120.125 | 131.258 | 98.713 | 108.304 | 21.165 | 23.413 |
| Stdev | 1.713 | 18.345 | 30.265 | 33.488 | 29.109 | 29.874 | 4.855 | 5.957 |
| StdError | 0.229 | 2.621 | 4.044 | 4.784 | 3.890 | 4.268 | 0.649 | 0.851 |
| WPGD2D | | 0.398 | *0.0329 | | *0.0140 | | | 0.117 |
| Average | 15.566 | 15.669 | 146.292 | 131.946 | 121.135 | 105.694 | 25.195 | 26.638 |
| Stdev | 2.087 | 2.273 | 38.584 | 40.853 | 35.867 | 38.380 | 7.009 | 7.512 |
| StdError | 0.295 | 0.304 | 5.457 | 5.459 | 5.072 | 5.129 | 0.991 | 1.004 |
| WPGD2F | | 0.036 | | 0.155 | | 0.084 | | 0.446 |
| Average | 14.820 | 14.077 | 130.985 | 126.517 | 109.005 | 102.142 | 23.053 | 23.931 |
| Stdev | 1.841 | 2.591 | 35.467 | 39.747 | 33.828 | 37.913 | 6.186 | 6.764 |
| StdError | 0.234 | 0.356 | 4.504 | 5.460 | 4.296 | 4.815 | 0.786 | 0.929 |
| WPGD1C; WPGD2B | | 0.109 | *0.015 | | *0.012 | | | 0.349 |
| Average | 15.442 | 14.834 | 149.895 | 134.001 | 124.672 | 109.654 | 24.717 | 25.116 |
| Stdev | 2.376 | 2.551 | 41.287 | 39.144 | 36.535 | 34.942 | 6.952 | 7.522 |
| StdError | 0.315 | 0.327 | 5.469 | 5.012 | 4.839 | 4.474 | 0.921 | 0.963 |
| WPGD1D; WPGD2B | | 0.330 | | 0.241 | | 0.213 | | 0.441 |
| Average | 15.700 | 15.700 | 154.419 | 159.730 | 128.630 | 134.360 | 26.235 | 26.168 |
| Stdev | 2.146 | 2.954 | 37.865 | 45.534 | 36.519 | 42.077 | 5.000 | 6.394 |
| StdError | 0.298 | 0.378 | 5.251 | 5.830 | 5.064 | 5.387 | 0.693 | 0.819 |

| | Mar. 15, 2017 | | | | | |
|---|---|---|---|---|---|---|
| Event pValue (T-Test) | Normal 100 kwt (g) | GMO 100 kwt (g) | Normal No. Kernels | GMO No. Kernels | Normal No. ears | GMO No. ears |
| WPGD1C | | | 0.189 | | 0.161 | |
| Average | 26.839 | 25.962 | 381.300 | 409.725 | 23.000 | 47.000 |
| Stdev | 2.361 | 2.711 | 111.124 | 87.294 | | |
| StdError | 0.492 | 0.395 | 23.171 | 12.733 | | |
| WPGD1D | 0.014* | | | 0.130 | | |
| Average | 26.487 | 24.796 | 396.570 | 428.081 | 47.000 | 52.000 |
| Stdev | 4.160 | 3.619 | 105.283 | 128.120 | | |
| StdError | 0.607 | 0.502 | 15.357 | 17.767 | | |
| WPGD1E | | 0.475 | *0.012 | | | |
| Average | 24.991 | 24.930 | 438.565 | 389.376 | 45.000 | 56.000 |
| Stdev | 3.726 | 4.333 | 144.524 | 142.892 | | |
| StdError | 0.555 | 0.579 | 21.544 | 19.095 | | |
| WPGD1F | | 0.172 | | 0.080 | | |
| Average | 24.210 | 24.869 | 429.086 | 390.204 | 55.000 | 57.000 |
| Stdev | 3.818 | 4.382 | 154.877 | 121.113 | | |
| StdError | 0.515 | 0.580 | 20.884 | 16.042 | | |
| WPGD2B | | 0.418 | | 0.188 | | |
| Average | 25.694 | 26.115 | 422.492 | 448.293 | 46.000 | 32.000 |
| Stdev | 2.582 | 4.517 | 116.328 | 139.620 | | |
| StdError | 0.381 | 0.799 | 17.152 | 24.682 | | |
| WPGD2C | *0.000025 | | | 0.147 | | |
| Average | 24.952 | 27.772 | 401.187 | 394.133 | 56.000 | 49.000 |
| Stdev | 2.915 | 3.629 | 123.128 | 108.114 | | |
| StdError | 0.390 | 0.518 | 16.454 | 15.445 | | |
| WPGD2D | | 0.258 | *0.007 | | | |
| Average | 25.068 | 25.151 | 492.449 | 424.684 | 50.000 | 56.000 |
| Stdev | 3.918 | 3.452 | 153.414 | 153.211 | | |
| StdError | 0.554 | 0.461 | 21.696 | 20.474 | | |
| WPGD2F | | 0.274 | | 0.183 | | |
| Average | 27.168 | 26.848 | 402.897 | 386.708 | 62.000 | 53.000 |
| Stdev | 3.690 | 4.284 | 119.561 | 144.108 | | |
| StdError | 0.469 | 0.588 | 15.184 | 19.795 | | |
| WPGD1C; WPGD2B | *0.004 | | | 0.233 | | |
| Average | 25.356 | 23.160 | 499.095 | 477.733 | 57.000 | 61.000 |
| Stdev | 4.243 | 3.856 | 143.774 | 144.042 | | |
| StdError | 0.562 | 0.494 | 19.043 | 18.443 | | |

TABLE 8-continued

Final Field Trial Statistics.

| | | | | | | | | |
|---|---|---|---|---|---|---|---|---|
| | WPGD1D; WPGD2B | | 0.155 | | 0.486 | | | |
| | Average | 27.207 | 39.690 | 475.487 | 483.009 | 52.000 | 61.000 | |
| | Stdev | 2.873 | 97.110 | 138.306 | 142.739 | | | |
| | StdError | 0.398 | 12.434 | 19.180 | 18.276 | | | |

TABLE 8 - PART II

Apr. 12, 2017

| Event pValue (T-Test) | Normal Ear length (cm) | GMO Ear length (cm) | Normal Ear weight (g) | GMO Ear weight (g) | Normal Grain yield (g) | GMO Grain yield (g) | Normal Cob weight (g) | GMO Cob weight (g) |
|---|---|---|---|---|---|---|---|---|
| WPGD1C | | 0.496 | | 0.102 | | 0.081 | | 0.353 |
| Average | 10.877 | 11.198 | 65.141 | 75.793 | 51.096 | 61.156 | 14.116 | 14.840 |
| Stdev | 2.761 | 2.124 | 33.775 | 28.031 | 30.027 | 24.445 | 4.851 | 4.377 |
| StdError | 0.412 | 0.295 | 5.035 | 3.887 | 4.476 | 3.390 | 0.723 | 0.607 |
| WPGD1D | *0.002 | | *0.0004 | | *0.0014 | | *0.000018 | |
| Average | 9.535 | 10.891 | 53.435 | 72.196 | 42.562 | 57.586 | 10.823 | 14.845 |
| Stdev | 2.921 | 2.537 | 32.245 | 34.694 | 29.010 | 31.012 | 4.493 | 5.220 |
| StdError | 0.387 | 0.362 | 4.271 | 4.956 | 3.842 | 4.430 | 0.595 | 0.746 |
| WPGD1E | | 0.478 | | 0.319 | | 0.354 | | 0.177 |
| Average | 12.958 | 13.411 | 75.375 | 84.757 | 61.414 | 69.040 | 14.180 | 16.025 |
| Stdev | 2.837 | 2.808 | 41.103 | 38.338 | 37.189 | 34.425 | 5.467 | 5.439 |
| StdError | 0.383 | 0.433 | 5.542 | 5.916 | 5.015 | 5.312 | 0.737 | 0.839 |
| WPGD1F | | 0.242 | | 0.239 | | 0.226 | | 0.171 |
| Average | 13.898 | 14.245 | 86.510 | 81.828 | 72.088 | 66.764 | 14.662 | 15.334 |
| Stdev | 2.830 | 2.551 | 37.235 | 33.420 | 35.543 | 31.777 | 3.721 | 4.300 |
| StdError | 0.368 | 0.338 | 4.848 | 4.427 | 4.627 | 4.209 | 0.484 | 0.570 |
| WPGD2B | | 0.145 | | 0.435 | | 0.478 | | 0.252 |
| Average | 10.809 | 10.383 | 65.228 | 67.988 | 51.225 | 54.356 | 14.101 | 13.822 |
| Stdev | 2.655 | 2.354 | 33.821 | 35.704 | 30.849 | 32.322 | 4.533 | 4.546 |
| StdError | 0.400 | 0.423 | 5.099 | 6.413 | 4.651 | 5.805 | 0.683 | 0.816 |
| WPGD2C | | 0.179 | | *0.010 | | *0.017 | | *0.001 |
| Average | 10.628 | 10.920 | 53.299 | 72.643 | 40.807 | 57.173 | 12.730 | 15.687 |
| Stdev | 2.220 | 2.321 | 29.680 | 32.648 | 27.684 | 29.514 | 3.833 | 4.290 |
| StdError | 0.356 | 0.342 | 4.753 | 4.814 | 4.433 | 4.352 | 0.614 | 0.633 |
| WPGD2D | | 0.332 | | *0.007 | | *0.007 | | *0.025 |
| Average | 14.669 | 14.202 | 74.728 | 99.366 | 56.368 | 78.594 | 18.104 | 21.121 |
| Stdev | 6.716 | 2.873 | 48.909 | 36.013 | 45.456 | 34.018 | 6.560 | 5.213 |
| StdError | 1.001 | 0.391 | 7.291 | 4.901 | 6.776 | 4.629 | 0.978 | 0.709 |
| WPGD2F | | 0.086 | | 0.081 | | 0.152 | *0.0005 | |
| Average | 13.429 | 14.023 | 87.964 | 96.271 | 70.256 | 76.931 | 18.228 | 22.252 |
| Stdev | 2.424 | 3.042 | 44.787 | 53.801 | 41.319 | 46.802 | 5.618 | 7.551 |
| StdError | 0.324 | 0.386 | 5.985 | 6.833 | 5.522 | 5.944 | 0.751 | 0.959 |
| WPGD1C; WPGD2B | | 0.451 | | 0.292 | | 0.300 | | 0.113 |
| Average | 14.095 | 13.975 | 106.597 | 109.805 | 86.729 | 89.496 | 19.785 | 20.980 |
| Stdev | 2.462 | 2.513 | 47.229 | 40.361 | 43.280 | 36.440 | 5.900 | 6.291 |
| StdError | 0.321 | 0.324 | 6.149 | 5.211 | 5.635 | 4.704 | 0.768 | 0.812 |
| WPGD1D; WPGD2B | | 0.233 | | 0.162 | | 0.100 | | 0.141 |
| Average | 14.657 | 15.103 | 116.096 | 124.267 | 93.684 | 103.248 | 22.519 | 21.453 |
| Stdev | 2.493 | 2.282 | 44.694 | 39.689 | 42.398 | 36.664 | 7.815 | 4.727 |
| StdError | 0.339 | 0.297 | 6.082 | 5.167 | 5.770 | 4.773 | 1.063 | 0.615 |

TABLE 8 - PART II

Apr. 12, 2017

| Event pValue (T-Test) | Normal 100 kwt (g) | GMO 100 kwt (g) | Normal No. Kernels | GMO No. Kernels | Normal No. ears | GMO No. ears |
|---|---|---|---|---|---|---|
| WPGD1C | | 0.056 | *0.0294 | | | |
| Average | 24.076 | 22.689 | 217.248 | 279.202 | 45.000 | 52.000 |
| Stdev | 4.019 | 3.382 | 133.181 | 120.823 | | |
| StdError | 0.599 | 0.469 | 19.853 | 16.755 | | |
| WPGD1D | | 0.304 | *0.0007 | | | |
| Average | 22.923 | 22.580 | 192.385 | 268.729 | 57.000 | 49.000 |
| Stdev | 4.125 | 3.488 | 141.785 | 156.788 | | |
| StdError | 0.546 | 0.498 | 18.780 | 22.398 | | |
| WPGD1E | | 0.421 | | 0.276 | | |
| Average | 21.455 | 21.082 | 296.447 | 335.361 | 55.000 | 42.000 |
| Stdev | 3.951 | 3.792 | 183.415 | 169.495 | | |
| StdError | 0.533 | 0.585 | 24.732 | 26.154 | | |

TABLE 8-continued

Final Field Trial Statistics.

| | | | | | | |
|---|---|---|---|---|---|---|
| WPGD1F | | 0.065 | | 0.150 | | |
| Average | 20.903 | 22.082 | 353.324 | 313.908 | 59.000 | 57.000 |
| Stdev | 3.884 | 3.625 | 184.566 | 158.781 | | |
| StdError | 0.506 | 0.480 | 24.028 | 21.031 | | |
| WPGD2B | | 0.323 | | 0.496 | | |
| Average | 24.052 | 24.084 | 221.402 | 231.564 | 44.000 | 31.000 |
| Stdev | 3.593 | 3.028 | 141.666 | 139.884 | | |
| StdError | 0.542 | 0.544 | 21.357 | 25.124 | | |
| WPGD2C | | 0.126 | *0.032 | | | |
| Average | 22.521 | 24.077 | 185.518 | 249.388 | 39.000 | 46.000 |
| Stdev | 4.093 | 4.986 | 129.220 | 138.731 | | |
| StdError | 0.655 | 0.735 | 20.692 | 20.455 | | |
| WPGD2D | | 0.187 | *0.004 | | | |
| Average | 23.540 | 22.983 | 250.014 | 347.120 | 45.000 | 54.000 |
| Stdev | 6.827 | 3.294 | 202.779 | 151.896 | | |
| StdError | 1.018 | 0.448 | 30.228 | 20.670 | | |
| WPGD2F | | 0.336 | | 0.231 | | |
| Average | 24.277 | 24.754 | 295.047 | 312.186 | 56.000 | 62.000 |
| Stdev | 4.669 | 4.694 | 175.345 | 197.862 | | |
| StdError | 0.624 | 0.596 | 23.431 | 25.129 | | |
| WPGD1C; WPGD2B | | 0.321 | | 0.159 | | |
| Average | 21.742 | 21.403 | 403.949 | 433.219 | 59.000 | 60.000 |
| Stdev | 3.955 | 4.047 | 203.952 | 182.041 | | |
| StdError | 0.515 | 0.522 | 26.552 | 23.501 | | |
| WPGD1D; WPGD2B | | 0.369 | *0.033 | | | |
| Average | 23.012 | 22.610 | 407.543 | 470.630 | 54.000 | 59.000 |
| Stdev | 3.295 | 4.231 | 183.358 | 171.226 | | |
| StdError | 0.448 | 0.551 | 24.952 | 22.292 | | |

C. Conclusions

These data suggest that the transgenes have strong effects to mitigate yield losses as plants are exposed to heat stress. Thus, expression of Wpgd1 or Wpgd2 provides an abiotic stress tolerance that does not have any apparent cost for growth under more optimal conditions.

REFERENCES

All documents, patents, journal articles and other materials cited in the present application are hereby incorporated by reference in their entirety.

1. Abramoff M D, Magalhaes P., Ram S J (2004) Image Processing with ImageJ. Biophotonics Int 11: 36-42.
2. Alonso A P, Val D L, Shachar-Hill Y (2010) Central metabolic fluxes in the endosperm of developing maize seeds and their implications for metabolic engineering. Metab Eng 13: 96-107.
3. Andorf C M, Cannon E K, Portwood J L, Gardiner J M, Harper L C, Schaeffer M L, Braun B L, Campbell D A, Vinnakota A G, Sribalusu V, et al (2016) MaizeGDB update: new tools, data and interface for the maize model organism database. Nucleic Acids Res 44: 1195-1201.
4. Armstrong, C. L., C. E. Green and R. L. Phillips (1991). Development and availability of germplasm with high Type I I culture formation response. Maize Genetics Coop Newsletter 65: 92-93.
5. Aoki N, Hirose T, Takahashi S, Ono K, Ishimaru K, Ohsugi R (1999) Molecular cloning and expression analysis of a gene for a sucrose transporter in maize (*Zea mays* L.). Plant Cell Physiol 40: 1072-1078.
6. Archibald J M (2015) Endosymbiosis and Eukaryotic Cell Evolution. Curr Biol 25: R911-R921.
7. Averill R H, Bailey-Serres J, Kruger N J (1998) Co-operation between cytosolic and plastidic oxidative pentose phosphate pathways revealed by 6-phosphogluconate dehydrogenase-deficient genotypes of maize. Plant J 14: 449-457.
8. Backlund P, Janetos A, Schimel D (2008) The Effects of Climate Change on Agriculture, Land Resources, Water Resources, and Biodiversity in the United States. Program 240.
9. Badu-Aprakut B, Hunter R B, Tollenaar M (1983) Effect of temperature during grain filling on whole plant and grain yield in maize (*Zea mays* L.). Can J Plant Sci 357-363.
10. Bahaji A, Li J, María Sánchez-López Á, Baroja-Fernindez E, Muñoz F J, Ovecka M, Almagro G, Montero M, Ezquer I, Etxeberria E, et al (2014) Starch biosynthesis, its regulation and biotechnological approaches to improve crop yields. Biotechnol Adv 32:87-106.
11. Bahaji A, Sanchez-Lopez A M, De Diego N, Munoz F J, Baroja-Fernandez E, Li J, Ricarte-Bermejo A, Baslam M, Aranjuelo I, Almagro G, et al (2015) Plastidic Phosphoglucose Isomerase Is an Important Determinant of Starch Accumulation in Mesophyll Cells, Growth, Photosynthetic Capacity, and Biosynthesis of Plastidic Cytokinins in *Arabidopsis*. PLoS One 10: 1/35.
12. Bailey-Serres J, Nguyen M T (1992) Purification and characterization of cytosolic 6-phosphogluconate dehydrogenase isozymes from maize. Plant Physiol 100: 1580-1583.
13. Bailey-Serres J, Tom J, Freeling M (1992) Expression and Distribution of Cytosolic 6-Phosphogluconate Dehydrogenase Isozymes in Maize. Biochem Genet 306: 233-246.
14. Benites G R F, Pinto A B P C (2011) Genetic gains for heat tolerance in potato in three cycles of Genetic gains for heat tolerance in potato in three cycles of recurrent selection. Crop Breed Appl Biotechnol 11: 133-140.
15. Bita C E, Gerats T (2013) Plant tolerance to high temperature in a changing environment: scientific fundamentals and production of heat stress-tolerant crops. Front Plant Sci 4: 273.

16. Boehlein S K, Shaw J R, Georgelis N, Curtis Hannah L (2014a) Enhanced heat stability and kinetic parameters of maize endosperm ADPglucose pyrophosphorylase by alteration of phylogenetically identified amino acids. Arch Biochem Biophys 543: 1-9.
17. Boehlein S K, Shaw J R, Georgelis N, Hannah L C (2014b) Enhanced heat stability and kinetic parameters of maize endosperm ADPglucose pyrophosphorylase by alteration of phylogenetically identified amino acids. Arch Biochem Biophys 543: 1-9.
18. Boehlein S K, Shaw J R, Hannah L C, Stewart J D (2010) Probing Allosteric Binding Sites of the Maize Endosperm ADP-Glucose Pyrophosphorylase. Plant Physiol 152: 85-95.
19. Boehlein S K, Shaw J R, Hwang S K, Stewart J D, Curtis Hannah L (2013) Deciphering the kinetic mechanisms controlling selected plant ADP-glucose pyrophosphorylases. Arch Biochem Biophys 535: 215-226.
20. Boehlein S K, Shaw J R, Stewart J D, Hannah L C (2008) Heat stability and allosteric properties of the maize endosperm ADP-glucose pyrophosphorylase are intimately intertwined.
Plant Physiol 146: 289-99.
21. Boehlein S K, Shaw J R, Stewart J D, Hannah L C (2009a) Studies of the Kinetic Mechanism of Maize Endosperm ADP-Glucose Pyrophosphorylase Uncovered Complex Regulatory Properties 1[W][OA]. Plant Physiol 152: 1056-1064.
22. Boehlein S K, Shaw J R, Stewart J D, Hannah L C (2009b) Characterization of an autonomously activated plant ADP-glucose pyrophosphorylase. Plant Physiol 149: 318-26
23. Boehlein S K, Shaw J R, Stewart J D, Sullivan B, Hannah L C (2015) Enhancing the heat stability and kinetic parameters of the maize endosperm ADP-glucose pyrophosphorylase using iterative saturation mutagenesis. Arch Biochem Biophys 568: 28-37.
24. Bowers J E, Chapman B A, Rong J, Paterson A H (2003) Unravelling angiosperm genome evolution by phylogenetic analysis of chromosomal duplication events. Nature 422: 433-437.
25. Boyer C D, Preiss J (1981) Evidence for Independent Genetic Control of the Multiple Forms of Maize Endosperm Branching Enzymes and Starch Synthases1 2. Plant Physiol 67: 1141-1145.
26. Brandner K, Sambade A, Boutant E, Didier P, Mély Y, Ritzenthaler C, Heinlein M (2008) Tobacco mosaic virus movement protein interacts with green fluorescent protein-tagged microtubule end-binding protein 1. Plant Physiol 147: 611-23.
27. Bryce W H, Nelson O E (1979) Starch-synthesizing Enzymes in the Endosperm and Pollen of Maize. Plant Physiol 63: 312-317.
28. Buchanan B B (1991) Regulation of C O, Assimilation in Oxygenic Photosynthesis: The Ferredoxin/Thioredoxin System Perspective on Its Discovery, Present Status, and Future Development. Arch Biochem Biophys 288: 1-9.
29. Bussell J D, Keech O, Fenske R, Smith S M (2013a) Requirement for the plastidial oxidative pentose phosphate pathway for nitrate assimilation in *Arabidopsis*. Plant J 75: 578-591.
30. Bussell J D, Keech O, Fenske R, Smith S M (2013b) Requirement for the plastidial oxidative pentose phosphate pathway for nitrate assimilation in *Arabidopsis*. Plant J 75: 578-591.
31. Campolina Machado J, Alves De Souza M, Melo De Oliveira D, Cargnin A, Júnior A, Pimentel B, Cristina De Assis J (2010) Recurrent selection as breeding strategy for heat tolerance in wheat. Crop Breed Appl Biotechnol 10: 9-15.
32. Cantarero M G, Cirilo A G, Andrade F H (1999) Night temperature at silking affects kernel set in maize. Crop Sci 39: 703-710.
33. Challinor A J, Koehler A-K, Ramirez-Villegas J, Whitfield S, Das B (2016) Current warming will reduce yields unless maize breeding and seed systems adapt immediately. Nat Clima 6: 954-960.
34. Cheng Z, Dong K, Ge P, Bian Y, Dong L, Deng X, Li X, Yan Y (2015) Identification of leaf proteins differentially accumulated between wheat cultivars distinct in their levels of drought tolerance. PLoS One 10: 1-20.
35. Cline K (1986) Import of Proteins into Chloroplasts. J Biol Chem 261: 14804-14810.
36. Cline K, Fulsom D R, Viitanen P V. (1989) An imported thylakoid protein accumulates in the stroma when insertion into thylakoids is inhibited. J Biol Chem 264: 14225-14232.
37. Colot V, Robert 'L S, Kavanagh T A, Bevan M W, Thompson R D, Schell J (1987) Localization of sequences in wheat endosperm protein genes which confer tissue-specific expression in tobacco. EMBO J 6: 3559-3564.
38. Commuri P D, Jones R J (2001) High Temperatures during Endosperm Cell Division in Maize. Crop Sci 41: 1122-1130.
39. Corpas F J, Barroso J B, Sandalio L M, Distefano S, Palma M, Lupia A, Del Ri L A (1998) A dehydrogenase-mediated recycling system of NADPH in plant peroxisomes. Biochem J 330: 777-784.
40. Cossani C M, Reynolds M P (2012) Update on Improving Heat Tolerance in Wheat Physiological Traits for Improving Heat Tolerance in Wheat. Plant Physiol 160: 1710-1718.
41. Debnam P M, Emes M J (1999) Subcellular distribution of enzymes of the oxidative pentose phosphate pathway in root and leaf tissues. J Exp Bot 50: 1653-1661.
42. Denyer K, Dunlap F, Thorbjsrnsen T, Keeling P, Smith A M (1996) The major form of ADP-glucose pyrophosphorylase in maize endosperm is extra-plastidial. Plant Physiol 112: 779-85.
43. Dereeper A, Guignon V, Blanc G, Audic S, Buffet S, Chevenet F, Dufayard J-F, Guindon S, Lefort V, Lescot M, et al (2008) Phylogeny.fr: robust phylogenetic analysis for the non-specialist. Nucleic Acids Res Web Serv 36: 465-469.
44. Dieuaide-Noubhani M, Raffard G, Canioni P, Pradet A, Raymond P (1995) Quantification of compartmented metabolic fluxes in maize root tips using isotope distribution from 13C- or 14C-labeled glucose. J Biol Chem 270: 13147-59.
45. Donald J E, Kulp D W, Degrado W F (2011) Salt Bridges: Geometrically Specific, Designable Interactions. Proteins 79: 898-915.
46. Driedonks N, Rieu I, Vriezen W H (2016) Breeding for plant heat tolerance at vegetative and reproductive stages. Plant Reprod. doi: 10.1007/s00497-016-0275-9.
47. Dutt M, Dhekney S A, Soriano L, Kandel R, Grosser J W (2014) Temporal and spatial control of gene expression in horticultural crops. Hortic Res. doi: 10.1038/hortres.2014.47.
48. Eicks M, Nica Maurino V, Knappe S, Flü U-I, Fischer K (2002) The Plastidic Pentose Phosphate Translocator Represents a Link between the Cytosolic and the Plastidic Pentose Phosphate Pathways in Plants 1. Plant Physiol 128: 512-522.

49. Emanuelsson O, Brunak S, von Heijne G, Nielsen H (2007) Locating proteins in the cell using TargetP, SignalP and related tools. Nat Protoc 2: 953-971.
50. Ettenhuber C, Spielbauer G, Margl L, Hannah L C, Gierl A, Bacher A, Genschel U, Eisenreich W (2005) Changes in flux pattern of the central carbohydrate metabolism during kernel development in maize. Phytochemistry 66: 2632-2642.
51. Eyshi Rezaei E, Webber H, Gaiser T, Naab J, Ewert F (2015) Heat stress in cereals: Mechanisms and modelling. Eur J Agron 64: 98-113.
52. Felker F C, Shannon J C (1980) Movement of 14C-labeled Assimilates into Kernels of Zea mays L. Plant Physiol 65: 864-870.
53. Feller U (2016) Drought stress and carbon assimilation in a warming climate: Reversible and irreversible impacts. J Plant Physiol 203: 84-94.
54. Filatov D A (2009) Processing and population genetic analysis of multigenic datasets with ProSeq3 software. Bioinforma Appl NOTE 25: 3189-3190.
55. Flint-Garcia S A (2013) Genetics and Consequences of Crop Domestication. J Agric Food Chem 61: 8277-8286.
56. Fonseca A E, Westgate M E (2005) Relationship between desiccation and viability of maize pollen. F Crop Res 114-125.
57. Gagat P, Bodyl A, Mackiewicz P (2013) How protein targeting to primary plastids via the endomembrane system could have evolved? A new hypothesis based on phylogenetic studies. Biol Direct 8:18.
58. Garcia G A, Dreccer M F, Miralles D J, Serrago R A (2015) High night temperatures during grain number determination reduce wheat and barley grain yield: A field study. Glob Chang Biol 21:4153-4164.
59. Gasteiger E, Gattiker A, Hoogland C, Ivanyi I, Appel R D, Bairoch A (2003) ExPASy: The proteomics server for in-depth protein knowledge and analysis. Nucleic Acids Res 31: 3784-3788.
60. Gault C M, Martin F, Mei W, Bai F, Black J B, Barbazuk W B, Settles A M (2017) Aberrant splicing in maize rough endosperm3 reveals a conserved role for U12 splicing in eukaryotic multicellular development. PNAS 114: E2195-E2204.
61. Georgelis N, Hannah L C (2008) Isolation of a heat-stable maize endosperm ADP-glucose pyrophosphorylase variant. Plant Sci 175: 247-254.
62. Giroux M J, Shaw J, Barryt G, Cobb B G, Greene T, Okita T, Hannah A L C, Phillips R L (1996a) A single gene mutation that increases maize seed weight. Genetics 93: 5824-5829.
63. Giroux M J, Shaw J, Barryt G, Cobb B G, Greene T, Okita T, Hannah A L C, Phillips R L (1996b) A single gene mutation that increases maize seed weight. Genetics 93: 5824-5829.
64. Glawischnig E, Gierl A, Tomas A, Bacher A, Eisenreich W (2001) Retrobiosynthetic nuclear magnetic resonance analysis of amino acid biosynthesis and intermediary metabolism. Metabolic flux in developing maize kernels. Plant Physiol 125: 1178-86.
65. Glawischnig E, Gierl A, Tomas A, Bacher A, Eisenreich W (2002) Starch biosynthesis and intermediary metabolism in maize kernels. Quantitative analysis of metabolite flux by nuclear magnetic resonance. Plant Physiol 130: 1717-27.
66. Gong F, Wu X, Zhang H, Chen Y, Wang W (2015) Making better maize plants for sustainable grain production in a changing climate. Front Plant Sci 6: 835.
67. Gong H, Chen G, Li F, Wang X, Hu Y, Bi Y (2012) Involvement of G6PDH in heat stress tolerance in the calli from *Przewalskia tangutica* and *Nicotiana tabacum*. Biol Plant 56: 422-430.
68. Gordon-Kamm W J, Spencer T M, Mangano M Lou, Adams T R, Daines R J, Start W G, O 'brien J V, Chambers S A, Adams W R, Willetts N G, et al (1990) Transformation of Maize Cells and Regeneration of Fertile Transgenic Plants. Plant Cell 2: 603-618.
69. Gororo N N, Eagles H A, Eastwood R F, Nicolas M E, Flood R G (2002) Use of *Triticum tauschii* to improve yield of wheat in low-yielding environments. Euphytica 123: 241-254.
70. Gottlieb L D (1982) Conservation and duplication of isozymes in plants. Science 216: 373-380.
71. Gottlieb L D, Weeden N F (1981) Correlation Between Subcellular Location and Phosphoglucose Isomerase Variability. Source Evol 35: 1019-1022.
72. Greene T W, Hannah L C (1998) Enhanced stability of maize endosperm ADP-glucose pyrophosphorylase is gained through mutants that alter subunit interactions. Plant Biol 95: 13342-13347.
73. Greene T W, Kavakli I H, Kahn M L, Okita T W, Nelson O E (1998) Generation of up-regulated allosteric variants of potato ADP-glucose pyrophosphorylase by reversion genetics. Plant Biol 95: 10322-10327.
74. Gustin J L, Jackson S, Williams C, Patel A, Armstrong P, Peter G F, Settles A M (2013) Analysis of Maize (*Zea mays*) Kernel Density and Volume Using Microcomputed Tomography and Single-Kernel Near-Infrared Spectroscopy. J Agric Food Chem 61: 10872-10880.
75. Hageman J, Baecke C, Ebskamp M, Pilon R, Smeekens S, Weisbeek P (1990) Protein Import into and Sorting inside the Chloroplast Are Independent Processes. Source Plant Cell 2: 479-494.
76. Hannah L. (2005) Starch synthesis in the maize endsoperm. Maydica 5: 497-506.
77. Hannah L C, Tuschall D M, Mans R J (1980) Multiple forms of maize endosperm adp-glucose pyrophosphorylase and their control by shrunken-2 and brittle-2. Genetics 95: 961-70.
78. Hannah W L C, Futch B, Bing J, Shaw J R, Boehlein S, Stewart J D, Beiriger R, Georgelis N, Greene T (2012) A shrunken-2 Transgene Increases Maize Yield by Acting in Maternal Tissues to Increase the Frequency of Seed Development. Plant Cell. doi: 10.1105/tpc.112.100602.
79. Hatfield J L, Prueger J H (2015) Temperature extremes: Effect on plant growth and development. Weather Clim Extrem 10: 4-10.
80. Hatfield J L, Singer J W (2010) Chapter 21: Climate Change: What to Expect and How Will It Affect Feedstock Production Options? Climate Change: What To Expect and How Will It Affect Feedstock Production Options? Sustain Altern Fuel Feed Oppor Challenges Roadmaps Six US Reg 349-360.
81. Hatzfeld W-D, Dancer J, Stitt M (1990) Fructose-2,6-bisphosphate, metabolites and coarse control of pyrophosphate: fructose-6-phosphate phosphotransferase during triose-phosphate cycling in heterotrophic cell-suspension cultures of *Chenopodium rubrum*. Planta 180: 205-211.
82. He W, Wang Y, Liu W, Zhou C-Z (2007) Crystal structure of *Saccharomyces cerevisiae* 6-phosphogluconate dehydrogenase Gnd1. BMC Struct Biol 7:38.
83. Herrero M P, Johnson R R (1980) High temperature stress and pollen viability in maize. Crop Sci 20: 796-800.
84. Hölscher C, Lutterbey M-C, Lansing H, Meyer T, Fischer K, von Schaewen A (2016). Defects in Peroxisomal 6-Phosphogluconate Dehydrogenase Isoform PGD2 Prevent Gametophytic Interaction in *Arabidopsis thaliana*. Plant Physiol 171: 192-205.
85. Hölscher C, Meyer T, von Schaewen A (2014) Dual-Targeting of *Arabidopsis* 6-Phosphogluconolactonase 3 (PGL3) to Chloroplasts and Peroxisomes Involves Interaction with Trx m2 in the Cytosol. Mol Plant @BULLET 7: 252-255.
86. Hong Z Q, Copeland L (1990) Pentose phosphate pathway enzymes in nitrogen-fixing leguminous root nodules. Phytochemistry 29: 2437-2440.
87. Hsiang S, Kopp R, Jina A, Rising J, Delgado M, Mohan S, Rasmussen D J, Muir-Wood R, Wilson P, Oppenheimer M, et al (2017) Estimating economic damage from climate change in the United States. Science (80-) 356: 1362-1369.
88. IPCC (2014) Climate Change 2014: Impacts, Adaptation, and Vulnerability.
89. James K D, Hughes M A, Williams P A (2000) Cloning and expression of ntnD, encoding a novel NAD(P)(+)-independent 4-nitrobenzyl alcohol dehydrogenase from *Pseudomonas* sp. Strain TW3. J Bacteriol 182: 3136-41.
90. John Sunoj V, Shroyer K J, Krishna Jagadish S, Vara Prasad P (2016) Diurnal temperature amplitude alters physiological and growth response of maize (*Zea mays* L.) during the vegetative stage. Environ Exp Bot 130: 113-121.
91. Jones R J, Ouattar S, Crookston R K (1985) Thermal Environment During Endosperm Cell Division and Grain Filling in Maize: Effects on Kernel Growth and Development in Vitro. Crop Sci 24: 133-137.
92. Jonik C, Sonnewald U, Hajirezaei M-R, Flugge U-I, Ludewig F (2012) Simultaneous boosting of source and sink capacities doubles tuber starch yield of potato plants. Plant Biotechnol J 10: 1088-1098.
93. Joshi J B, Geetha S, Singh B, Kumar K K, Kokiladevi E, Arul L, Balasubramanian P, Sudhakar D (2014) A maize α-zein promoter drives an endosperm-specific expression of transgene in rice. Physiol Mol Biol Plants 21: 35-42.
94. Journet E-P, Douce R (1985) Enzymic Capacities of Purified Cauliflower Bud Plastids for Lipid Synthesis and Carbohydrate Metabolism'. Plant Physiol 79: 458-467.
95. Katzen F (2007) Gateway® recombinational cloning: a biological operating system. Expert Opin Drug Discov 2: 571-589.
96. Klösgen R B, Gierl A, Schwarz-Sommer Z, Saedler H (1986) Molecular analysis of the waxy locus of *Zea mays*. Mol Gen Genet 203: 237-244.
97. Klösgen R B, Saedler H, Weil J H (1989) The amyloplast-targeting transit peptide of the waxy protein of maize also mediates protein transport in vitro into chloroplasts. Mol Gen Genet 217:155-161.
98. Klösgen R B, Weil J H (1991) Subcellular location and expression level of a chimeric protein consisting of the maize waxy transit peptide and the beta-glucuronidase of *Escherichia coli* in transgenic potato plants. Mol Gen Genet 225: 297-304.
99. Krepinsky K, Plaumann M, Martin W, Schnarrenberger C (2001) Purification and cloning of chloroplast 6-phosphogluconate dehydrogenase from spinach. Eur J Biochem 268: 2678-2686.
100. Kruger N J, von Schaewen A (2003) The oxidative pentose phosphate pathway: structure and organisation. Curr Opin Plant Biol 6: 236-246.
101. Kulcinskaja E, Rosengren A, Ibrahim R, Kolenovi K, Stilbrand H (2013) Expression and characterization of a *Bifidobacterium adolescentis* beta-mannanase carrying mannan-binding and cell association motifs. Appl Environ Microbiol 79: 133-40.
102. Kumar S, Tsai C-J, Nussinov R (2000) Factors enhancing protein thermostability. Protein Eng 13: 179-191.
103. Kuntz M, Simons A, Schell J, Schreier P H (1986) MGG Targeting of protein to chloroplasts in transgenic tobacco by fusion to mutated transit peptide. Mol Gen Genet 205: 454-460.
104. Lertrat K, Pulam T (2007) International Journal of Plant Breeding©2007 Global Science Books Breeding for Increased Sweetness in Sweet Corn. Int J Plant Breed 27-30.
105. Li H min, Teng Y S (2013) Transit peptide design and plastid import regulation. Trends Plant Sci 18: 360-366.
106. Linebarger C R, Boehlein S K, Sewell A K, Shaw J, Hannah L C (2005) Heat stability of maize endosperm ADP-glucose pyrophosphorylase is enhanced by insertion of a cysteine in the N terminus of the small subunit. Plant Physiol 139: 1625-1634.
107. Lobell D B, Hammer G L, McLean G, Messina C, Roberts M J, Schlenker W (2013) The critical role of extreme heat for maize production in the United States. Nat Clim Chang 3: 497-501.
108. Lu D, Shen X, Cai X, Yan F, Lu W, Shi Y C (2014) Effects of heat stress during grain filling on the structure and thermal properties of waxy maize starch. Food Chem 143: 313-318.
109. Lu D, Sun X, Yan F, Wang X, Xu R, Lu W (2013) Effects of high temperature during grain filling under control conditions on the physicochemical properties of waxy maize flour. Carbohydr Polym 98: 302-310.
110. Maheshwari A S, Archunan G (2012) Distribution of amino acids in functional sites of proteins with high melting temperature. Bioinformation 8: 1176-81.
111. Maier U G, Brown J W., Toloczyki C, Feix G (1987) Binding of a nuclear factor to a consensus sequence in the 5' flanking region of zein genes from maize. EMBO J 6: 17-22.
112. Marie-Christin Lutterbey A von S, To (2017) Analysis of homo- and hetero-dimerization among the three 6-phosphogluconate dehydrogenase isoforms of *Arabidopsis*. doi: 10.1080/15592324.2016.1207034.
113. Mayer L I, Savin R, Maddonni G A (2016) Heat stress during grain filling modifies kernel protein composition in field-grown maize. Crop Sci 56: 1890-1903.
114. Melillo, Jerry M., Terese (T.C.) Richmond, and Gary W. Yohe, Eds., (2014): Climate Change Impacts in the United States: The Third National Climate Assessment. U.S. Global Change Research Program, 841 pp. doi:10.7930/JOZ31WJ2.
115. Meyer T, Hölscher C, Schw6ppe C, Von Schaewen A (2011) Alternative targeting of *Arabidopsis* plastidic glucose-6-phosphate dehydrogenase G6PD1 involves cysteine-dependent interaction with G6PD4 in the cytosol. Plant J 66: 745-758.
116. Mezulis S, Yates C M, Wass M N, E Sternberg M J, Kelley L A (2015) The Phyre2 web portal for protein modeling, prediction and analysis. Nat Protoc 10: 845-858.
117. Mickelbart M V., Hasegawa P M, Bailey-Serres J (2015) Genetic mechanisms of abiotic stress tolerance that translate to crop yield stability. Nat Rev Genet 16: 237-251.

118. Miller M E, Chourey P S (1992) The Maize Invertase-Deficient miniature-1 Seed Mutation Is Associated with Aberrant Pedicel and Endosperm Development. Plant Cell 4: 297-305.
119. Millet E J, Welcker C, Kruijer W, et al. Genome-Wide Analysis of Yield in Europe: Allelic Effects Vary with Drought and Heat Scenarios. Plant Physiology. 2016; 172(2):749-764. doi:10.1104/pp. 16.00621.
120. Murray et al., (1989) Nucl. Acids Res. 17:477-498.
121. Neuhaus H E, Emes M J (2000) Non Phototosynthetic Metabolism in Plastids. Annu Rev Plant Physiol Plant Mol Biol 51: 111-40.
122. Nishimura M, Beevers H (1979) Subcellular distribution of gluconeogenetic enzymes in germinating castor bean endosperm. Plant Physiol 64: 31-7.
123. NOAA (2016) National Centers for Environmental Information, State of the Climate: Global Climate Report for Annual 2016, published online January 2017, retrieved on Jul. 20, 2017 from https://www.ncdc.noaa.gov/sotc/global/201613.
124. Nuccio M L, Wu J, Mowers R, Zhou H-P, Meghji M, Primavesi L F, Paul M J, Chen X, Gao Y, Haque E, et al (2015) Expression of trehalose-6-phosphate phosphatase in maize ears improves yield in well-watered and drought conditions. Nat Biotechnol 33: 862-869.
125. OECD/FAO (2016) "Cereals", in OECD-FAO Agricultural Outlook 2016-2025. OECD Publ Paris 7: 98-123.
126. Van de Peer Y, Mizrachi E, Marchal K (2017) The evolutionary significance of polyploidy. Nat Publ Gr. doi: 10.1038/nrg.2017.26.
127. Peng S, Huang J, Sheehy J E, Laza R C, Visperas R M, Zhong X, Centeno G S, Khush G S, Cassman K G (2004) Rice yields decline with higher night temperature from global warming.
128. Peraudeau S, Lafarge T, Roques S, Quiñones C O, Clement-Vidal A, Ouwerkerk P B F, Rie J Van, Fabre D, Jagadish K S V, Dingkuhn M (2015) Effect of carbohydrates and night temperature on night respiration in rice. J Exp Bot 66: 3931-3944.
129. Piperno D R, Ranere A J, Holst I, Iriarte J, Dickau R (2009) Starch grain and phytolith evidence for early ninth millennium B.P. maize from the Central Balsas River Valley, Mexico. PNAS 106: 5019-5204.
130. Platenius H (1942) Effect of temperature on the respiration rate and the respiratory quotient of some vegetables. Plant Physiol 17: 179-197.
131. Porter G A, Knievel D P, Shannon J C (1985) Sugar Efflux from Maize (Zea mays L.) Pedicel Tissue. Plant Physiol 77: 524-31.
132. Prasanna B (2012) Diversity in global maize germplasm: Characterization and utilization. J Biosci 37: 843-855.
133. Preiss J, Danner S, Summers P S, Morell M, Barton C R, Yang L, Nieder M (1990) Molecular Characterization of the Brittle-2 Gene Effect on Maize Endosperm ADP-glucose Pyrophosphorylase Subunits. Plant Physiol 92: 881-5.
134. Quayle T, Feix G (1992) Functional analysis of the −300 region of maize zein genes. Mol Gen Genet 231: 369-74.
135. Reed C J, Lewis H, Trejo E, Winston V, Evilia C (2013) Protein adaptations in archaeal extremophiles. Archaea 2013: 373275.
136. Reumann S, Ma C, Lemke S, Babujee L (2004) AraPerox. A Database of Putative Arabidopsis Proteins from Plant Peroxisomes. Plant Physiol 136: 2587-2608.
137. Ribeiro, C. (2017) Engineering 6-phosphogluconate dehydrogenase to improve heat stability of starch accumulation in maize seed development (Doctoral dissertation). Attached to disclosure submission.
138. Ruan Y-L, Jin Y, Yang Y-J, Li G-J, Boyer J S (2010) Sugar Input, Metabolism, and Signaling Mediated by Invertase: Roles in Development, Yield Potential, and Response to Drought and Heat. Mol Plant 3: 942-955.
139. Sadeghi M, Naderi-Manesh H, Zarrabi M, Ranjbar B (2005) Effective factors in thermostability of thermophilic proteins. 119: 256-270.
140. Sage R F (2004) The evolution of C 4 photosynthesis. New Phytol 161: 341-370.
141. Sakulsingharoj C, Choi S-B, Hwang S-K, Edwards G E, Bork J, Meyer C R, Preiss J, Okita T W (2004) Engineering starch biosynthesis for increasing rice seed weight: the role of the cytoplasmic ADP-glucose pyrophosphorylase. Plant Sci 167: 1333.
142. Sánchez B, Rasmussen A, Porter J R (2014) Temperatures and the growth and development of maize and rice: A review. Glob Chang Biol 20: 408-417.
143. Saripalli G, Gupta P K (2015) AGPase: its role in crop productivity with emphasis on heat tolerance in cereals. Theor Appl Genet 128: 1893-1916.
144. Scheibe R (1991) Redox-Modulation of Chloroplast Enzymes1 A Common Principle for Individual Control. Plant Physiol 96: 1-3.
145. Schnarrenberger C, Flechner A, Martin W (1995) Enzymatic Evidence for a Complete Oxidative Pentose Phosphate Pathway in Chloroplasts and an Incomplete Pathway in the Cytosol of Spinach Leaves'. Plant Physiol 108: 609-61.
146. Schlenker W, Roberts M J. Nonlinear temperature effects indicate severe damages to U.S. crop yields under climate change. Proceedings of the National Academy of Sciences of the United States of America. 2009; 106(37): 15594-15598. doi:10.1073/pnas.0906865106.
147. Schoper J B, Lambert R J, Vasilas B L, Westgate M E (1987) Plant factors controlling seed set in maize: the influence of silk, pollen, and ear-leaf water status and tassel heat treatment at pollination. Plant Physiol 83: 121-5.
148. Settles A M, Holding D R, Tan B C, Latshaw S P, Liu J, Suzuki M, Li L, O'brien B A, Fajardo D S, Wroclawska E, et al (2007) Sequence-indexed mutations in maize using the UniformMu transposon-tagging population. BMC Genomics 8: 1-12.
149. Shannon J C, Pien F M, Cao H, Liu K C (1998) Brittle-1, an adenylate translocator, facilitates transfer of extraplastidial synthesized ADP-glucose into amyloplasts of maize endosperms. Plant Physiol 117: 1235-1252.
150. Shi J, Lai J (2015) Patterns of genomic changes with crop domestication and breeding. Curr Opin Plant Biol 24: 47-53.
151. Shotwell M A, Boyer S K, Chesnutg R S, Larkin B A (1990) Analysis of Seed Storage Protein Genes of Oats. J Biol Chem 265: 9652-9658.
152. Sievers F, Wilm A, Dineen D, Gibson T J, Karplus K, Li W, Lopez R, Mcwilliam H, Remmert M, SÖ Ding J, et al (2011) Fast, scalable generation of high-quality protein multiple sequence alignments using Clustal Omega. Mol Syst Biol 7: 1-6.
153. Silva-Filho M C (2003) One ticket for multiple destinations: dual targeting of proteins to distinct subcellular locations. Curr Opin Plant Biol 6: 589-595.

154. Singletary G W, Banisadr R, Keelingac P L (1994) Heat Stress During Grain Filling in Maize: Effects on Carbohydrate Storage and Metabolism. Aust J Plant Physiol 21: 829-41.

155. Shaw R H (1983) Estimates of yield reductions in corn caused by water and temperature stress. In C D Ruper, Jr, P J Kramer, eds, Crop Relations to Water and Temperature Stress in Humid Tem-perate Climates. Westview Press, Boulder, Colo., pp 49-66.

156. Smidansky E D, Clancy M, Meyer F D, Lanning S P, Blake N K, Talbert L E, Giroux M J (2002a) Enhanced ADP-glucose pyrophosphorylase activity in wheat endosperm increases seed yield. Proc Natl Acad Sci USA 99: 1724-1729.

157. Smidansky E D, Clancy M, Meyer F D, Lanning S P, Blake N K, Talbert L E, Giroux M J, Nelson O E (2002b) Enhanced ADP-glucose pyrophosphorylase activity in wheat endosperm increases seed yield. PNAS 99: 1724-1729.

158. Smidansky E D, Martin J M, Hannah C L, Fischer A M, Giroux M J (2003) Seed yield and plant biomass increases in rice are conferred by deregulation of endosperm ADP-glucose pyrophosphorylase. Planta 216: 656-664.

159. Smidansky E D, Meyer F D, Blakeslee B, Weglarz T E, Greene T W, Giroux M J (2007) Expression of a modified ADP-glucose pyrophosphorylase large subunit in wheat seeds stimulates photosynthesis and carbon metabolism. Planta 225: 965-976.

160. Solomon S, Plattner G-K, Knutti R, Friedlingstein P (2008) Irreversible climate change due to carbon dioxide emissions. PNAS 106: 1704-1709.

161. Soltis P S, Liu X, Marchant D B, Visger C J, Soltis D E (2014) Polyploidy and novelty: Gottlieb's legacy. Phil Trans R Soc B 396: 1-12.

162. Song R, Messing J, Larkins B A (2003) Gene expression of a gene family in maize based on noncollinear haplotypes. PNAS 100: 9055-9060.

163. Spielbauer G, Armstrong P, Baier J W, Allen W B, Richardson K, Shen B, Settles A M (2009) High-Throughput Near-Infrared Reflectance Spectroscopy for Predicting Quantitative and Qualitative Composition Phenotypes of Individual Maize Kernels. Cereal Chem 86: 556-564.

164. Spielbauer G, Li L, R6misch-Margl L, Do P T, Fouquet R, Fernie A R, Eisenreich W, Gierl A, Settles A M (2013) Chloroplast-localized 6-phosphogluconate dehydrogenase is critical for maize endosperm starch accumulation. J Exp Bot 64: 2231-2242.

165. Spielbauer G, Margl L, Hannah L C, R6 Misch W, Ettenhuber C, Bacher A, Gierl A, Eisenreich W, Genschel U (2006) Robustness of central carbohydrate metabolism in developing maize kernels. Phytochemistry 67: 1460-1475.

166. Stark D M, Timmerman K P, Barry G F, Preiss J, Kishore G M (1992) Regulation of the Amount of Starch in Plant Tissues by ADP Glucose Pyrophosphorylase. Science (80) 258.

167. Stuber C W, Goodman M M (1983) Inheritance, intracellular localization, and genetic variation of phosphoglucomutase isozymes in maize (Zea mays L.). Biochem Genet 21: 667-89.

168. Suwa R, Hakata H, Hara H, El-Shemy H A, Adu-Gyamfi J J, Nguyen N T, Kanai S, Lightfoot D A, Mohapatra P K, Fujita K (2010) High temperature effects on photosynthate partitioning and sugar metabolism during ear expansion in maize (Zea mays L.) genotypes. Plant Physiol Biochem 48: 124-130.

169. Sweetlove L J, Nielsen J, Fernie A R (2017) Engineering central metabolism—a grand challenge for plant biologists. Plant J 90: 749-763.

170. Tello-Ruiz M K, Stein J, Wei S, Preece J, Olson A, Naithani S, Amarasinghe V, Dharmawardhana P, Jiao Y, Mulvaney J, et al (2016) Gramene 2016: comparative plant genomics and pathway resources. Nucleic Acids Res 44: D1133-D1140.

171. Tetaud E, Hanau S, Wells J M, LePage R W F, Adams M J, Arkison S, Barrett M P (1999) 6-Phosphogluconate dehydrogenase from Lactococcus lactis: a role for arginine residues in binding substrate and coenzyme. Biochem J 338: 55-60.

172. Thomas P A, Felker F C, Crawford2 C G (1992) Sugar Uptake and Metabolism in the Developing Endosperm of Tassel-seed Tunicate (Ts-5 Tu) Maize. Plant Physiol 99: 1540-1545.

173. Thompson G A, Larkins B A (1989) Structural elements regulating zein gene expression. BioEssays 10: 108-113.

174. Ueda T, Messing J (1991) A homologous expression system for cloned zein genes. Theor Appl Genet 82: 93-100.

175. Ueda T, Wang Z, Pham N, Messing J (1994) Identification of a Transcriptional Activator-Binding Element in the 27-Kilodalton Zein Promoter, the −300 Element. Mol Cell Biol 14:4350-4359.

176. Uribelarrea M, Below F E, Moose S P (2004) Grain composition and productivity of maize hybrids derived from the Illinois protein strains in response to variable nitrogen supply. Crop Sci 44:1593-1600.

177. Vieille C, Zeikus G J, Vieille C (2001) Hyperthermophilic Enzymes: Sources, Uses, and Molecular Mechanisms for Thermostability Hyperthermophilic Enzymes: Sources, Uses, and Molecular Mechanisms for Thermostability. Microbiol Mol Biol Rev 65: 1-43.

178. Viola R, Davies H V, Chudeck A R (1991) Pathways of starch and sucrose biosynthesis in developing tubers of potato (Solanum tuberosum L.) and seeds of faba bean (Vicia faba L.). Planta 183: 202-208.

179. Wahid A, Gelani S, Ashraf M, Foolad M R (2007) Heat tolerance in plants: An overview. Environ Exp Bot 61: 199-223.

180. Walley J W, Shen Z, McReynolds M R, Briggs S P (2016) Fungal Induced Protein Hyperacetylation Identified by Acetylome Profiling. bioRxiv.

181. Walley J W, Shen Z, Sartor R, Wu K J, Osborn J, Smith L G, Briggs S P (2013) Reconstruction of protein networks from an atlas of maize seed proteotypes. Proc Natl Acad Sci USA 110: E4808-17.

182. Wang Z, Chen X, Wang J, Liu T, Liu Y, Zhao L, Wang G (2007) Increasing maize seed weight by enhancing the cytoplasmic ADP-glucose pyrophosphorylase activity in transgenic maize plants. Plant Cell Tissue Organ Cult 88: 83-92.

183. Wheeler D L, Church D M, Federhen S, Lash A E, Madden T L, Pontius J U, Schuler G D, Schriml L M, Sequeira E, Tatusova T A, et al (2003) Database resources of the national center for biotechnology. Nucleic Acids Res 31: 28-33.

184. Wilhelm E P, Mullen R E, Keeling P L, Singletary G W (1999) Heat stress during filling in maize: effects on kernal growth and metabolism. Crop Sci 39: 1733-1741.

185. Woo Y M, Hu D W, Larkins B A, Jung R (2001) Genomics analysis of genes expressed in maize endosperm identifies novel seed proteins and clarifies patterns of zein gene expression. Plant Cell 13: 2297-317.

186. Wright D, Marois J, Rowland D (2014) Field Corn Production Guide. Agron Dep UF/IFAS Ext 1-12.
187. Xiong Y, DeFraia C, Williams D, Zhang X, Mou Z (2009b) Characterization of *Arabidopsis* 6-Phosphogluconolactonase T-DNA Insertion Mutants Reveals an Essential Role for the Oxidative Section of the Plastidic Pentose Phosphate Pathway in Plant Growth and Development. Plant Cell Physiol 50: 1277-129110.
188. Xiong Y, DeFraia C, Williams D, Zhang X, Mou Z (2009a) Deficiency in a cytosolic ribose-5-phosphate isomerase causes chloroplast dysfunction, late flowering and premature cell death in *Arabidopsis*. Physiol Plant 137: 249-263.
189. Zhao C, Liu B, Piao S, Wang X, Lobell D B, Huang Y, Huang M, Yao Y, Bassu S, Ciais P, Durand J L, Elliott J, Ewert F, Janssens I A, Li T, Lin E, Liu Q, Martre P, Müller C, Peng S, Penuelas J, Ruane A C, Wallach D, Wang T, Wu D, Liu Z, Zhu Y, Zhu Z, Asseng S. Temperature increase reduces global yields of major crops in four independent estimates. Proc Natl Acad Sci USA. 2017 Aug. 29; 114(35):9326-9331.

The invention claimed is:

1. An expression cassette comprising a regulatory region operably linked to a nucleic acid sequence encoding a fusion protein comprising a plastid targeting sequence, wherein the plastid targeting sequence comprises a N-terminal chloroplast targeting sequence of starch synthase Waxy1 fused in frame with cytosolic 6-phosphogluconate dehydrogenase (6PGDH), wherein the regulatory region is a plant promoter.

2. A nucleic acid sequence encoding a fusion protein, wherein the fusion protein comprises a plastid targeting sequence, wherein the plastid targeting sequence comprises a N-terminal chloroplast targeting sequence of starch synthase Waxy1 fused in frame with cytosolic 6-phosphogluconate dehydrogenase (6PGDH), wherein the fusion protein is able to import into a plastid of a plant cell.

3. A transgenic plant comprising a nucleic acid sequence encoding a fusion protein, wherein the fusion protein comprises a plastid targeting sequence, wherein the plastid targeting sequence comprises a N-terminal chloroplast targeting sequence of starch synthase Waxy1jused in frame with cytosolic 6-phosphogluconate dehydrogenase (6PGDH), wherein the fusion protein is able to import into a plastid of a plant cell.

4. A method for developing a transgenic plant that has increased heat resistance and yield during heat stress, comprising introducing an expression cassette comprising a regulatory region operably linked to a nucleic acid sequence encoding a fusion protein comprising a plastid targeting sequence fused in frame with cytosolic 6-phosphogluconate dehydrogenase (6PGDH), wherein the plastid targeting sequence comprises N-terminal chloroplast targeting sequence of starch synthase Waxy1 or VVC.

5. The expression cassette of claim 1, wherein the plastid targeting sequence comprises VVC.

6. The expression cassette of claim 2, wherein the plastid targeting sequence comprises VVC.

7. The transgenic plant of claim 3, wherein the plastid targeting sequence comprises VVC.

8. The expression cassette of claim 1, wherein the regulatory region is a promoter region of a zein.

9. The expression cassette of claim 8, wherein the zein is alpha-zein or gamma-zein.

\* \* \* \* \*